US006498163B1

(12) United States Patent
Boschelli et al.

(10) Patent No.: US 6,498,163 B1
(45) Date of Patent: *Dec. 24, 2002

(54) PYRIDO[2,3-D]PYRIMIDINES AND 4-AMINOPYRIMIDINES AS INHIBITORS OF CELLULAR PROLIFERATION

(75) Inventors: Diane Harris Boschelli, New City, NY (US); Annette Marian Doherty, Paris (FR); Ali Fattaey, San Francisco, CA (US); David William Fry, Ypsilanti, MI (US); Susanne Andrea Trumpp-Kallmeyer, Ann Arbor, MI (US); Zhipei Wu, Saline, MI (US); Ellen Myra Dobrusin, Ann Arbor, MI (US); Mark Robert Barvian, Ann Arbor, MI (US)

(73) Assignee: Warner-Lambert Company, Morris Plains, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/355,681
(22) PCT Filed: Jan. 26, 1998
(86) PCT No.: PCT/US98/01343
§ 371 (c)(1), (2), (4) Date: Aug. 2, 1999
(87) PCT Pub. No.: WO98/33798
PCT Pub. Date: Aug. 6, 1998

Related U.S. Application Data
(60) Provisional application No. 60/037,220, filed on Feb. 5, 1997.

(51) Int. Cl.$^7$ .............. A61K 31/519; A01N 43/90; C07D 487/00
(52) U.S. Cl. .............. 514/264.1; 514/258.1; 514/264.1; 544/279
(58) Field of Search .............. 514/258.1, 264.1; 544/279

(56) References Cited

U.S. PATENT DOCUMENTS

| | | | | |
|---|---|---|---|---|
| 5,620,981 A | * | 4/1997 | Blankley et al. | 514/210.21 |
| 5,733,914 A | * | 3/1998 | Blankley et al. | 514/210.21 |

FOREIGN PATENT DOCUMENTS

| | | |
|---|---|---|
| EP | 0021292 | 1/1981 |
| EP | 0278686 | 8/1988 |
| WO | 9220642 | 11/1992 |
| WO | 9509845 | 4/1995 |
| WO | 9515952 | 6/1995 |
| WO | 9615128 | 5/1996 |
| WO | 9634867 | 11/1996 |
| WO | 9738992 | 10/1997 |

OTHER PUBLICATIONS

J.I. Borrel et al; "An Unequivocal Synthesis of 4–amino–1,5,6,8–tetra–hydropyrido"2,3–d!pyrimidine–2,7–diones and . . . ; 1996; Coll. Czech. Chem. Commun.; vol. 61, No. 6, pp. 901–909.

(List continued on next page.)

Primary Examiner—Mukund J. Shah
Assistant Examiner—Tamthom N. Truong
(74) Attorney, Agent, or Firm—Charles W. Ashbrook; Rosanne Goodman

(57) ABSTRACT

This invention provides pyridopyrimidines and 4-aminopyrimidines that are useful for treating cell proliferative disorders, such as cancer and restenosis. We have now discovered a group of 7,8-dihydro-2-(amino and thio) pyrido[2,3-d]pyrimidines and 2,4-diaminopyrimidines that are potent inhibitors of cyclin-dependent kinases (cdks) and growth factor-mediated kinases. The compounds are readily synthesized and can be administered by a variety of routes, including orally, and have sufficient bioavailability. This invention provides compounds of Formula I:

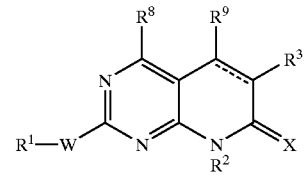

I and Formula II:

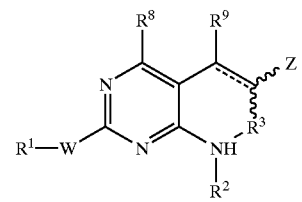

II where
  W is NH, S, SO, or SO$_2$,
  R$^1$ includes phenyl and substituted phenyl,
  R$^2$ includes alkyl and cycloalkyl,
  R$^3$ includes alkyl and hydrogen,
  R$^8$ and R$^9$ include hydrogen and alkyl, and
  Z is carboxy.

This invention also provides pharmaceutical formulations comprising a compound of Formula I or II together with a pharmaceutically acceptable carrier, diluent, or excipient therefor.

44 Claims, No Drawings

OTHER PUBLICATIONS

B.S. Hurlbert et al; "Studies on Condensed Pyrimidine Systems. XXIII, Synthesis of 2,4–Diaminopyrido'2,3–d!pyrimidiines"...; 1968, J. Med. Chem.; vol. 11, pp. 703–707.

B.R. Baker et al; "Analogs of Tetrahydrofolic acid. XIX. On the Mode of Binding of the Pyrimidyl Moiety . . . "; 1964; J. Heterocyclic Chem.; vol. 1; pp. 263–270.

Anderson et al; "Pyridopyrimidines 6. Nucleophilic Substitutions in the Pyrido'2,3–d!pyrimidine Series"; 1977; J. Org. Chem.; vol. 42, p. 993.

A.M. Schoffstall et al; "Synthesis of 5,6–Dihydropyrido'2, 3–d!pyrimidine Derivatives Directly from Acyclic Precursors" 1971; J. Org. Chem.; vol. 36, No. 16, pp. 2385–2387.

P. Victory et al; "New Synthesis of pyrido'2,3–d49 pyrimidines. 1. Reaction of 6–alkoxy–5–cyano–3,4–dihydro–2–pyridones with Guanidine and Cyanamide"; 1985; Heterocycles; vol. 23, No. 5, pp. 1135–1141.

P. Victory et al; "Cyclisation of Dinitriles by hydrogen halides. 1. Hydrogen bromide"; Heterocycles; vol. 23, No. 8, pp. 1947–1950.

P. Victory; "Nueva sintesis de prirdo'2,3–d!pirimidinas. V.Deshidrogenacion del anillo dihidropiridonico . . . "; 3/89; Afinidad; vo. 46, pp. 107–113.

G.W. Rewcastle et al; Tyrosine Kinase Inhibitors. 10. Isomeric 4–(3–Bromophenyl)Aminopyrido D–Pyrimidines are Potent ATP Binding Site Inhibitors of the Tyrosine Kinase Function of the Epidermal Growth Factor Receptor; 1996; Journal of Medicinal Chemistry; vol. 39, No. 9.

* cited by examiner

PYRIDO[2,3-D]PYRIMIDINES AND 4-AMINOPYRIMIDINES AS INHIBITORS OF CELLULAR PROLIFERATION

This application claims the benefit of Provisional Application No. 60/037,220 filed Feb. 5, 1997.

FIELD OF THE INVENTION

This invention relates to pyridopyrimidines and 4-aminopyrimidines that inhibit cyclin-dependent kinase and growth factor-mediated kinase enzymes, and as such are usefull to treat cell proliferative disorders such as atherosclerosis, restenosis, and cancer.

SUMMARY OF THE RELATED ART

Cell cycle kinases are naturally occurring enzymes involved in regulation of the cell cycle (Meijer L., "Chemical Inhibitors of Cyclin-Dependent Kinases", *Progress in Cell Cycle Research*, 1995;1:351–363). Typical enzymes include the cyclin-dependent kinases (cdk) cdk1, cdk2, cdk4, cdk5, cdk6, and wee-1 kinase. Increased activity or temporally abnormal activation of these kinases has been shown to result in development of human tumors and other proliferative disorders such as restenosis. Compounds that inhibit cdks, either by blocking the interaction between a cyclin and its kinase partner, or by binding to and inactivating the kinase, cause inhibition of cell proliferation, and are thus useful for treating tumors or other abnormally proliferating cells.

Several compounds that inhibit cdks have demonstrated both preclinical and clinical anti-tumor activity. For example, flavopiridol is a flavonoid that has been shown to be a potent inhibitor of several types of breast and lung cancer cells (Kaur, et al., *J. Natl. Cancer Inst.*, 1992;84:1736–1740; *Int. J. Oncol.*, 1996;9:1143–1168). The compound has been shown to inhibit cdk2 and cdk4. Olomoucine [2-hydroxyethylamine)-6-benzylamine-9-methylpurine] is a potent inhibitor of cdk2 and cdk5 (Vesely, et al., *Eur. J. Biochem.*, 1994;224:771–786), and has been shown to inhibit proliferation of approximately 60 different human tumor cell lines used by the National Cancer Institute (NCI) to screen for new cancer therapies (Abraham, et al., *Biology of the Cell*, 1995;83:105–120).

Despite the progress that has been made, the search continues for small molecular weight compounds that are orally bioavailable and useful for treating a wide variety of human tumors and other proliferative disorders such as restenosis and atherosclerosis.

SUMMARY OF THE INVENTION

This invention provides pyridopyrimidines and 4-aminopyrimidines that are useful for treating cell proliferative disorders, such as cancer, atherosclerosis, restenosis, psoriasis, and endometriosis. We have discovered a group of 7,8-dihydro-2-(amino and thio)-7-(oxo, thio, or imino)-pyrido[2,3-d]pyrimidines and 4-aminopyrimidines that are potent inhibitors of cyclin-dependent kinases (cdks). The compounds are readily synthesized and can be administered by a variety of routes, including orally and parenterally, and have little or no toxicity. The compounds of the invention are members of the class of compounds of Formula I:

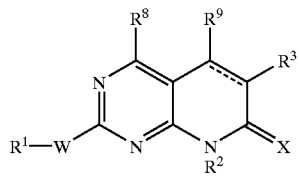

and Formula II:

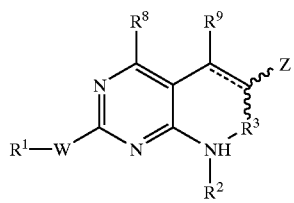

wherein:
 W is NH, S, SO, or $SO_2$;
 $R^1$ and $R^2$ include alkyl, cycloalkyl, substituted alkyl, and substituted cycloalkyl;
 $R^3$ includes hydrogen, alkyl, and halogen;
 X is O, S, or NH;
 $R^8$ and $R^9$ independently are hydrogen, alkyl, alkoxy, halo, amino, and the like;
and pharmaceutically acceptable salts thereof.

This invention also provides pharmaceutical formulations comprising a compound of Formula I or II together with a pharmaceutically acceptable carrier, diluent, or excipient therefor.

Compounds within the scope of the present invention are inhibitors of the cyclin-dependent kinases such as cdk2, cdc2, and cdk4. Some of the compounds of the present invention also inhibit growth factor mediated tyrosine kinases including platelet-derived growth factor (PDGF), fibroblast growth factor (FGF), and epidermal growth factor (EGF). As inhibitors of cyclin-dependent, as well as growth factor-mediated, tyrosine kinases, the compounds of the instant invention are useful in controlling proliferative disorders such as cancer, psoriasis, vascular smooth muscle cell proliferation associated with atherosclerosis, and postsurgical vascular stenosis and restenosis in mammals.

A further embodiment of this invention is a method of treating subjects suffering from diseases caused by cellular proliferation. The method entails inhibiting proliferation of tumorigenic cells of epithelial origin and vascular smooth muscle proliferation, and/or cellular migration by administering a therapeutically effective amount of a compound of Formula I and/or II to a subject in need of treatment.

A further embodiment of this invention is a method of treating subjects suffering from diseases caused by DNA tumor viruses such as herpes viruses.

DETAILED DESCRIPTION OF THE INVENTION

We have discovered a new class of compounds that are potent inhibitors of cyclin-dependent kinases (cdks) and are useful agents for treating subjects suffering from diseases caused by abnormal cell proliferation. Compounds within the scope of the present invention are inhibitors of the cyclin-dependent kinases such as cdc2, cdk2, and cdk4. As inhibitors of cyclin-dependent kinases, the compounds of the instant invention are useful in controlling proliferative disorders such as cancer, psoriasis, vascular smooth muscle proliferation associated with atherosclerosis, postsurgical vascular stenosis, and restenosis in mammals.

The compounds of the invention comprise those of Formula I:

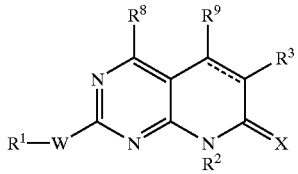

and the pharmaceutically acceptable salts thereof, wherein:

the dotted line represents an optional double bond;

W is NH, S, SO, or $SO_2$;

X is either O, S, or NH;

$R^1$ and $R^2$ are independently selected from the group consisting of H, $(CH_2)_n Ar$, $(CH_2)_n$heteroaryl, $(CH_2)_n$ heterocyclyl, $C_1$–$C_{10}$ alkyl, $C_3$–$C_{10}$ cycloalkyl, $C_2$–$C_{10}$ alkenyl, and $C_2$–$C_{10}$ alkynyl, wherein n is 0, 1, 2, or 3, and the $(CH_2)_n Ar$, $(CH_2)_n$heteroaryl, alkyl, cycloalkyl, alkenyl, and alkynyl groups are optionally substituted by up to 5 groups selected from $NR^4R^5$, $N(O)R^4R^5$, $NR^4R^5R^6Y$, alkyl, phenyl, substituted phenyl, $(CH_2)_n$ heteroaryl, hydroxy, alkoxy, phenoxy, thiol, thioalkyl, halo, $COR^4$, $CO_2R^4$, $CONR^4R^5$, $SO_2NR^4R^5$, $SO_3R^4$, $PO_3R^4$, aldehyde, nitrile heteroaryloxy, $T(CH_2)_m QR^4$,

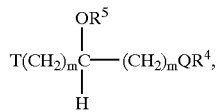

$C(O)T(CH_2)_m QR^4$, $NHC(O)T(CH_2)_m QR^4$, $T(CH_2)_m C(O) NR^4NR^5$, or $T(CH_2)_m CO_2R^4$ wherein each m is independently 1–6, T is O, S, $NR^4$, $N(O)R^4$, $NR^4R^6Y$, or $CR^4R^5$, and Q is O, S, NR5, $N(O)R^5$, or $NR^5R^6Y$;

$R^3$ is H, alkyl, halogen, $NO_2$, $NR^4R^5$, $COOR^4$, $OR^4$, CN, or $CONR^4R^5$;

$R^4$ and $R^5$ are each independently selected from the group consisting of hydrogen, $C_1$–$C_6$ alkyl, substituted alkyl, $C_2$–$C_6$ alkenyl, $C_2$–$C_6$ alkynyl, $(CH_2)_n Ar$, $C_3$–$C_{10}$ cycloalkyl, heterocyclyl, and heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

$R^4$ and $R^5$ are independently selected from the group consisting of hydrogen, $C_1$–$C_6$ alkyl, substituted alkyl, $C_3$–$C_{10}$ cycloalkyl, $C_2$–$C_6$ heterocyclyl, and $C_2$–$C_6$ heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur; optionally substituted with alkyl, $T(CH_2)_m QR^{4'}$, $C(O)T(CH_2)_m QR^{4'}$, $T(CH_2)_m CO_2R^{4'}$, $(CH_2)_m QR^{4'}$, $T(CH_2)_m CONR^{4'}R^{5'}$ wherein m is 1–6, T is O, S, $NR^{4'}$, $N(O)R^{4'}$, or $CR^{4'}R^{5'}$, and Q is O, S, $NR^{5'}$, or $N(O)R^{5'}$;

$R^{4'}$ and $R^{5'}$ are independently selected from the group consisting of hydrogen, $C_1$–$C_6$ alkyl, substituted alkyl, $C_3$–$C_{10}$ cycloalkyl, $C_2$–$C_6$ heterocyclyl, and $C_2$–$C_6$ heteroaryl;

$R^6$ is alkyl;

$R^8$ and $R^9$ independently are H, $C_1$–$C_3$alkyl, $NR^4R^5$, $N(O)R^4R^5$, $NR^4R^5R^6Y$, hydroxy, alkoxy, thiol, thioalkyl, halo, $COR^4$, $CO_2R^4$, $CONR^4R^5$, $SO_2NR^4R^5$, $SO_3R^4$, $PO_3R^4$, CHO, CN, or $NO_2$; and Y is a halo counter-ion.

An especially preferred group of compounds of Formula I have the above formula wherein X is O.

Another preferred group of compounds are those wherein W is NH.

A preferred group of compounds of Formula I have the above formula wherein X is O, and $R^3$ is $CH_3$ or H. In an especially preferred group of compounds, X is O, and $R^3$ is H.

Also preferred are compounds of Formula I wherein $R^8$ and $R^9$ both are hydrogen.

Another preferred group of compounds of Formula I have the above formula wherein X is O, and $R^2$ is Et, Pr, i-Pr, i-Bu, i-pentyl, or cycloalkyl. In an especially preferred group of compounds, X is O and $R^2$ is i-Pr or i-pentyl.

In yet another preferred group of compounds of Formula I, X is O, and $R^1$ is phenyl. Another preferred group of compounds of Formula I have one or more of the following structural features: X is O, and there is a double bond between $C_5$ and $C_6$, $R^1$ is phenyl, optionally substituted with 4-piperidinyl (with or without substitution), 4-(2-diethylaminoethoxy) or 4-(4-methyl piperazin-1-yl); and $R^2$ is a branched alkyl or cycloalkyl, including but not limited to isopropyl, cyclopentyl, cyclohexyl, or norbornyl. In an especially preferred group of compounds, X is O, and $R^1$ is phenyl substituted with hydroxy, alkoxy, $NR^4R^5$, or $T(CH_2)_m QR^4$, where $R^4$ and $R^5$, T, m, and Q all are as defined above. In an even more preferred group of compounds, X is O, and $R^1$ is phenyl substituted with $NR^4R^5$ or $T(CH_2)_m QR^4$, where $R^4$ and $R^5$, T, m, and Q all are as defined above.

Another preferred group of compounds of Formula I are those wherein X is NH.

The most preferred compounds of the present invention have the formula:

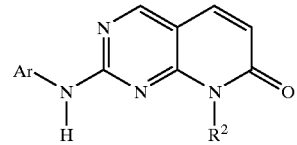

where $R^2$ is as defined above, and Ar is phenyl, substituted phenyl, or heteroaryl. Ideally, $R^2$ is alkyl such as ethyl, isopropyl, propyl, butyl, or isopentyl, or cycloalkyl such as norbornyl, cyclohexyl, or adamantyl. A most preferred Ar group is phenyl, preferably substituted with 1, 2, or 3 groups selected from phenyl, chloro, bromo, methyl, methoxy, hydroxy, hydroxymethyl, 2-diethylaminoethoxy, methoxycarbonylmethyl, carboxy, carboxymethyl, ethoxycarbonyl, 2-carboxyethyl, 2-ethoxycarbonylethyl, $NR^4R^5$, and $O(CH_2)_{0-6}NR^4R^5$, wherein $R^4$ and $R^5$ are as defined above. Another preferred Ar group is thiazolyl, for example, 2-thiazolyl, optionally substituted by phenyl, hydroxyphenyl, or alkoxyphenyl.

Additional preferred embodiments of the present invention include those in Examples 38, 41, 43, 51, 52, 53, 55, 74, 79, 84, and 85, infra. Even more preferred compounds are those displayed in Examples 59, 60, 77, 217, and 259 infra.

Compounds of Formula I wherein W is S, SO, or $SO_2$ are especially useful as intermediates leading to compounds where W is NH, but such compounds also display inhibitory activity against cyclin-dependent kinases.

The compounds of the invention further comprise those of Formula II:

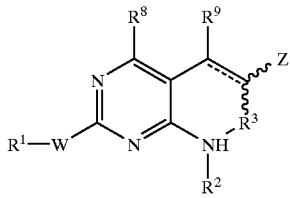

wherein:
the dotted line represents an optional double bond of either trans or cis-stereochemistry;

W is NH, S, SO, or $SO_2$;

Z is $COOR^7$, CN, CHO, $CH_2QR^7$, $CH_2NHR^7$, $CONHR^7$, or $COR^7$;

$R^1$ and $R^2$ are independently selected from the group consisting of H, $(CH_2)_n$Ph, $(CH_2)_n$heteroaryl, $(CH_2)_n$ heterocycle, $C_1$–$C_{10}$ alkyl, $C_3$–$C_{10}$ cycloalkyl, $C_2$–$C_{10}$ alkenyl, and $C_2$–$C_{10}$ alkynyl, wherein n is 0, 1, 2, or 3 and the $(CH_2)_n$Ph, $(CH_2)_n$heteroaryl, alkyl, cycloalkyl, alkenyl, and alkynyl groups are optionally substituted by groups of $NR^4R^5$, $N(O)R^4R^5$, $NR^4R^5R^6Y$, phenyl, substituted phenyl, hydroxy, alkoxy, phenoxy, thiol, thioalkyl, halo, $COR^4$, $CO_2R^4$, $CONR^4R^5$, $SO_2NR^4R^5$, $SO_3R^4$, $PO_3R^4$, aldehyde, nitrile, nitro, heteroaryloxy, $T(CH_2)_mQR^4$, $C(O)T(CH_2)_mQR^4$, $NHC(O)T(CH_2)_m$ $QR^4$, or $T(CH_2)_mCO_2R^4$ wherein m is 1–6, T is O, S, $NR^4$, $N(O)R^4$, $NR^4R^6Y$, or $CR^4R^5$, and Q is O, S, $NR^5$, $N(O)R^5$, or $NR^5R^6Y$;

$R^3$ is H or alkyl;

$R^4$ and $R^5$ are independently selected from the group consisting of hydrogen, $C_1$–$C_6$ alkyl, substituted alkyl, $C_2$–$C_6$ alkenyl, $C_2$–$C_6$ alkynyl, $(CH_2)_n$Ph, $C_3$–$C_{10}$ cycloalkyl, and heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

$R^6$ is alkyl;

Y is a halo counter-ion;

$R^7$ is one of H, lower alkyl, or phenyl.

$R^8$ and $R^9$ independently are H, $C_1$–$C_3$alkyl, $NR^4R^5$, $N(O)R^4R^5$, $NR^4R^5R^68$, hydroxy, alkoxy, thiol, thioalkyl, halo, $COR^4$, $CO_2R^4$, $CONR^4R^5$, $SO_2NR^4R^5$, $SO_3R^4$, $PO_3R^4$, CHO, CN, or $NO_2$;

and the pharmaceutically acceptable salts thereof.

Preferably, compounds of Formula II have a trans double bond between $C_5$ and $C_6$, more preferably with $R^1$ being phenyl, and even more preferably with both $R^1$ being phenyl and $R^2$ being alkyl or cycloalkyl.

Also preferred are compounds of Formula II wherein $R^8$ and $R^9$ both are hydrogen.

Examples of $NR^4R^5$ groups include amino, methylamino, di-isopropylamino, acetyl amino, propionyl amino, 3-aminopropyl amino, 3-ethylaminobutyl amino, 3-di-n-propylamino-propyl amino, 4-diethylaminobutyl amino, and 3-carboxypropionyl amino. $R^4$ and $R^5$ can be taken together with the nitrogen to which they are attached to form a ring having 3 to 7 carbon atoms and 1, 2, or 3 heteroatoms selected from the group consisting of nitrogen, substituted nitrogen, oxygen, and sulfur. Examples of such cyclic $NR^4R^5$ groups include pyrrolidinyl, piperazinyl, 4-methylpiperazinyl, 4-benzylpiperazinyl, pyridinyl, piperidinyl, pyrazinal, morpholinyl, and the like.

Unless otherwise expressly stated, the following definitions are adhered to throughout this disclosure.

"Alkyl" means a straight or branched hydrocarbon radical having from 1 to 10 carbon atoms (unless stated otherwise) and includes, for example, methyl, ethyl, n-propyl, isopropyl, n-butyl, sec-butyl, isobutyl, tert-butyl, n-pentyl, iso-pentyl, n-hexyl, and the like.

"Halo" includes fluoro, chloro, bromo, and iodo.

"Alkenyl" means straight and branched hydrocarbon radicals having from 2 to 6 carbon atoms and one double bond and includes ethenyl, 3-buten-1-yl, 2-ethenylbutyl, 3-hexen-1-yl, and the like.

"Alkynyl" means straight and branched hydrocarbon radicals having from 2 to 6 carbon atoms and one triple bond and includes ethynyl, 3-butyn-1-yl, propynyl, 2-butyn-1-yl, 3-pentyn-1-yl, and the like.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocyclyl", which means a cycloalkyl group also bearing at least one heteroatom selected from O, S, or $NR_2$, examples being oxiranyl, pyrrolidinyl, piperidyl, tetrahydropyran, and morpholine.

"Alkoxy" refers to the alkyl groups mentioned above bound through oxygen, examples of which include methoxy, ethoxy, isopropoxy, tert-butoxy, and the like. In addition, alkoxy refers to polyethers such as O—$(CH_2)_2$—O—$CH_3$, and the like.

"Alkanoyl" groups are alkyl linked through a carbonyl, ie, $C_1$–$C_5$—C(O)—. Such groups include formyl, acetyl, propionyl, butyryl, and isobutyryl.

"Acyl" means an alkyl or aryl (Ar) group bonded through a carbonyl group, ie, R—C(O)—. For example, acyl includes a $C_1$–$C_6$ alkanoyl, including substituted alkanoyl, wherein the alkyl portion can be substituted by $NR^4R^5$ or a carboxylic or heterocyclic group. Typical acyl groups include acetyl, benzoyl, and the like.

The alkyl, alkenyl, alkoxy, and alkynyl groups described above are optionally substituted, preferably by 1 to 3 groups selected from $NR^4R^5$, phenyl, substituted phenyl, thio $C_1$–$C_6$ alkyl, $C_1$–$C_6$ alkoxy, hydroxy, carboxy, $C_1$–$C_6$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_n$Ph where n is 1, 2, or 3. Perhalo and polyhalo substitution is also embraced.

Examples of substituted alkyl groups include 2-aminoethyl, pentachloroethyl, trifluoromethyl, 2-diethylaminoethyl, 2-dimethylaminopropyl, ethoxycarbonylmethyl, 3-phenylbutyl, methanylsulfanyl-methyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Examples of substituted alkynyl groups include 2-methoxyethynyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, trifluoromethoxy, 2-diethylaminoethoxy, 2-ethoxycarbonyl-ethoxy, 3-hydroxypropoxy, 6-carbohexyloxy, and the like.

Further, examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrinidyl-butyl, 3-imidazolidin-1-ylpropyl, 4-tetrahydrothiazol-3-yl-butyl, phenylmethyl, 3-chlorophenylmethyl, and the like.

The terms "Ar" and "aryl" refer to unsubstituted and substituted aromatic groups. Heteroaryl groups have from 4 to 9 ring atoms, from 1 to 4 of which are independently selected from the group consisting of O, S, and N. Preferred heteroaryl groups have 1 or 2 heteroatoms in a 5- or 6-membered aromatic ring. Mono and bicyclic aromatic ring systems are included in the definition of aryl and heteroaryl. Typical aryl and heteroaryl groups include phenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, pyrrole, pyrazole, imidazole, thiazole, and the like.

Preferred Ar groups are phenyl and phenyl substituted by 1, 2, or 3 groups independently selected from the group consisting of alkyl, alkoxy, thio, thioalkyl, hydroxy, —$COOR^7$, amino of the formula —$NR^4R^5$, and $T(CH_2)_m QR^4$ or $T(CH_2)_m CO_2R^4$ wherein m is 1 to 6, T is O, S, $NR^4$, $N(O)R^4$, $NR^4R^6Y$, or $CR^4R^5$, Q is O, S, $NR^5$, $N(O)R^5$, or $NR^5R^6Y$ wherein $R^4$ and $R^5$ are as described above, and $R^7$ is alkyl or substituted alkyl, for example, methyl, trichloroethyl, diphenylmethyl, and the like. The alkyl and alkoxy groups can be substituted as defined above. For example, typical groups are carboxyalkyl, alkoxycarbonylalkyl, hydroxyalkyl, hydroxyalkoxy, and alkoxyalkyl.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formula I and II are capable of further forming both pharmaceutically acceptable formulations comprising salts, including but not limited to acid addition and/or base salts, solvents and N-oxides of a compound of Formula I and/or II. This invention also provides pharmaceutical formulations comprising a compound of Formula I and/or II together with a pharmaceutically acceptable carrier, diluent, or excipient therefor. All of these forms are within the present invention.

Pharmaceutically acceptable acid addition salts of the compounds of Formula I and II include salts derived form inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, capryl ate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like.

Also contemplated are the salts of amino acids such as arginate, gluconate, galacturonate, and the like; see, for example, Berge, et al., "Pharmaceutical Salts," *J. of Pharmaceutical Science*, 1977;66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and allcine earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge, et al., supra.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

The compounds of the present invention are useful for treating cancer (for example, leukemia and cancer of the lung, breast, prostate, and skin such as melanoma) and other proliferative diseases including but not limited to psoriasis, HSV, HIV, restenosis, and atherosclerosis. To utilize a compound of the present invention to treat cancer, a patient having cancer is administered a therapeutically effective amount of a pharmaceutically acceptable composition comprising an invention compound.

A further embodiment of this invention is a method of treating subjects suffering from diseases caused by vascular smooth muscle cell proliferation. Compounds within the scope of the present invention effectively inhibit vascular smooth muscle cell proliferation and migration. The method entails inhibiting vascular smooth muscle proliferation, and/or migration by administering an effective amount of a compound of Formula I and/or II to a subject in need of treatment.

The compounds of the present invention can be formulated and administered in a wide variety of oral and parenteral dosage forms, including transdermal and rectal administration. It will be recognized to those skilled in the art that the following dosage forms may comprise as the active component, either a compound of Formula I and/or II or a corresponding pharmaceutically acceptable salt or solvate of a compound of Formula I and/or II.

A further embodiment of this invention is a pharmaceutical formulation comprising a compound of Formula I and/or II together with a pharmaceutically acceptable carrier, diluent, or excipient therefor. For preparing pharmaceutical compositions with the compounds of the present invention, pharmacuetically acceptable carriers can be either a solid or liquid. Solid form preparations include powders, tablets, pills, capsules, cachets, suppositories, and dispensible granules. A solid carrier can be one or more substances which may also act as diluents, flavoring agents, binders, preservatives, tablet disintegrating agents, or an encapsulating material.

In powders, the carrier is a finely divided solid such as talc or starch which is in a mixture with the finely divided active component. In tablets, the active component is mixed with the carrier having the necessary binding properties in suitable proportions and compacted in the shape and size desired.

The formulations of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogenously therein, as by stirring. The molten homogenous mixture is then poured into convenient size molds, allowed to cool, and thereby to solidify.

Liquid form preparations include solutions, suspensions, and emulsions such as water or water/propylene glycol solutions. For parenteral injection, liquid preparations can be formulated in solution in aqueous polyethylene glycol solution, isotonic saline, 5% aqueous glucose, and the like. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water and mixing with a viscous material, such as natural or synthetic gums, resins, methylcellulose, sodium carboxymethylcellulose, or other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be utilized to prepare sustained-release dosage forms. Also, osmotic pumps can be employed to deliver the active compound uniformally over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The therapeutically effective dose of a compound of Formula I and/or Formula II will generally be from about 1 mg to about 100 mg/kg of body weight per day. Typical adult doses will be about 50 mg to about 800 mg per day. The quantity of active component in a unit dose preparation may be varied or adjusted from about 0.1 mg to about 500 mg, preferably about 0.5 mg to 100 mg according to the particular application and the potency of the active component. The composition can, if desired, also contain other compatible therapeutic agents. A subject in need of treatment with a compound of Formula I and/or II is administered a dosage of about 1 to about 500 mg per day, either singly or in multiple doses over a 24-hour period.

The compounds of the present invention are capable of binding to and inhibiting the activity of proteins having the ability to phosphorylate other proteins, such as cdks, PDGFr, FGFr, c-src, and EGFr-FL. Cdks form complexes with cyclins, and these complexes phosphorylate key proteins allowing cells to proceed through the cell cycle (Meijer L., *Progress in Cell Cycle Research*, 1995;1:351–363). The compounds of this invention inhibit this phosphorylation and therefore can be used as anti-proliferative agents for the treatment of cancer and/or restenosis and other proliferative diseases.

Because of their inhibitory activity against cdks and other kinases, the compounds of the present invention are also useful research tools for studying the mechanism of action of those kinases, both in vitro and in vivo.

While the forms of the invention herein constitute presently preferred embodiments, many others are possible. It is not intended herein to mention all of the possible equivalent forms or ramifications of the invention. It is understood that the terms used herein are merely descriptive rather than limiting, and those skilled in the art will realize that various changes may be made without departing from the spirit or scope of the invention.

The following compounds illustrate specific embodiments provided by the present invention, and the compounds listed below are among the preferred embodiments.

8-(3-Phenoxy-benzyl)2-phenylamino-8H-pyrido[2,3-d]pyrimidin-7-one;
8-(2-Cyclopropyl-ethyl)-2-phenylamino-8H-pyrido[2,3-d]pyrimidin-7-one;
8-(2-Naphthalen-2-yl-ethyl)-2-phenylamino-8H-pyrido[2,3-d]pyrimidin-7-one;
8-(3,5-Dimethoxy-benzyl)-2-phenylamino-8H-pyrido[2,3-d]pyrimidin-7-one;
8-Hex-2-ynyl-2-phenylamino-8H-pyrido[2,3-d]pyrimidin-7-one;
8-(4-Methylsulfanyl-benzyl)-2-phenylamino-8H-pyrido[2,3-d]pyrimidin-7-one;
8-(3,3-Dimethyl-butyl)-2-phenylamino-8H-pyrido[2,3-d]pyrimidin-7-one;
8-(2-Phenethyl-benzyl)-2-phenylamino-8H-pyrido[2,3-d]pyrimidin-7-one;
8-(2-Ethyl-hexyl)-2-phenylamino-8H-pyrido[2,3-d]pyrimidin-7-one;
8-Cyclohex-3-enylmethyl-2-phenylamino-8H-pyrido[2,3-d]pyrimidin-7-one;
8-Bicyclo[2.2.1]hept-2-ylmethyl-2-phenylamino-8H-pyrido[2,3-d]pyrimidin-7-one;
8-(4-Chloro-2-nitro-benzyl)-2-phenylamino-8H-pyrido[2,3-d]pyrimidin-7-one;
8-(3-Ethyl-oxetan-3-ylmethyl)-2-phenylamino-8H-pyrido[2,3-d]pyrimidin-7-one;
8-[2-(2-Methoxy-ethoxy)-ethyl]-2-phenylamino-8H-pyrido[2,3-d]pyrimidin-7-one;
8-(2,2,3,3,3-Pentafluoro-propyl)-2-phenylamino-8H-pyrido[2,3-d]pyrimidin-7-one;
2-Phenylamino-8-(tetrahydro-furan-2-ylmethyl)-8H-pyrido[2,3-d]pyrimidin-7-one;

8-(3-Methyl-but-2-enyl)-2-phenylamino-8H-pyrido[2,3-d]pyrimidin-7-one;

8-[2-(4tert-Butyl-phenoxy)-ethyl]-2-phenylamino-8H-pyrido[2,3-d]pyrimidin-7-one;

8-(4-Ethyl-benzyl)-2-phenylamino-8H-pyrido[2,3-d]pyrimidin-7-one;

8-(2-Phenoxy-ethyl)-2-phenylamino-8H-pyrido[2,3-d]pyrimidin-7-one;

8-(2-Methyl-allyl)-2-phenylamino-8H-pyrido[2,3-d]pyrimidin-7-one;

8-(3-Methyl-benzyl)-2-phenylamino-8H-pyrido[2,3-d]pyrimidin-7-one;

8-(4-Methyl-benzyl)-2-phenylamino-8H-pyrido[2,3-d]pyrimidin-7-one;

8-(2-Butoxy-ethyl)-2-phenylamino-8H-pyrido[2,3-d]pyrimidin-7-one;

2-Phenylamino-8-(2,2,2-trifluoro-ethyl)-8H-pyrido[2,3-d]pyrimidin-7-one;

2-Phenylamino-8-(2-thiophen-2-yl-ethyl)-8H-pyrido[2,3-d]pyrimidin-7-one;

8-Benzo[1,3]dioxol-5-ylmethyl-2-phenylamino-8H-pyrido[2,3-]pyrimidin-7-one;

8-Cyclohexylmethyl-2-phenylamino-8H-pyrido[2,3-d]pyrimidin-7-one;

8-(2-Ethoxy-ethyl)-2-phenylamino-8H-pyrido[2,3-d]pyrimidin-7-one;

2-Phenylamino-8-thiophen-2-ylmethyl-8H-pyrido[2,3-d]pyrimidin-7-one;

8-Furan-2-ylmethyl-2-phenylamino-8H-pyrido[2,3-d]pyrimidin-7-one;

8-(3-Phenyl-allyl)-2-phenylamino-8H-pyrido[2,3-d]pyrimidin-7-one;

8-Furan-3-ylmethyl-2-phenylamino-8H-pyrido[2,3-d]pyrimidin-7-one;

8-(3-Methoxy-propyl)-2-phenylamino-8H-pyrido[2,3-d]pyrimidin-7-one;

8-(3-Methyl-bicyclo[2.2.1]hept-2-ylmethyl)-2-phenylamino-8H-pyrido[2,3-d]pyrimidin-7-one;

2-Phenylamino-8-(3-phenyl-prop-2-ynyl)-8H-pyrido[2,3-d]pyrimidin-7-one;

8-(2-Methyl-3-oxo-butyl)-2-phenylamino-8H-pyrido[2,3-d]pyrimidin-7-one;

8-[Bis-(4-fluoro-phenyl)-methyl]-2-phenylamino-8H-pyrido[2,3-d]pyrimidin-7-one;

8-[Cyclopropyl-(4-fluoro-phenyl)-methyl]-2-phenylamino-8H-pyrido[2,3-d]pyrimidin-7-one;

8-(2-Isopropyl-cyclohexyl)-2-phenylamino-8H-pyrido[2,3-d]pyrimidin-7-one;

8-(2,2,3,3,4,4,5,5,6,6,7,7-Dodecafluoro-1,1-dimethyl-heptyl)-2-phenylamino-8H-pyrido[2,3-d]pyrimidin-7-one;

2-Phenylamino-8-(1,7,7-trimethyl-bicyclo[2.2.1]hept-2-yl)-8H-pyrido[2,3-d]pyrimidin-7-one;

2-Phenylamino-8-(2,2,2-trifluoro-1-phenyl-ethyl)-8H-pyrido[2,3-d]pyrimidin-7-one;

2-Phenylamino-8-(2,2,2-trichloro-1-phenyl-ethyl)-8H-pyrido[2,3-d]pyrimidin-7-one;

8-(2,3-Dimethyl-cyclohexyl)-2-phenylamino-8H-pyrido[2,3-d]pyrimidin-7-one;

2-Phenylamino-8-(tetrahydro-pyran-4-yl)-8H-pyrido[2,3-d]pyrimidin-7-one;

8-Cyclohex-2-enyl-2-phenylamino-8H-pyrido[2,3-d]pyrimidin-7-one;

2-Phenylamino-8-(1,3,3-trimethyl-bicyclo[2.2.1]hept-2-yl)-8H-pyrido[2,3-d]pyrimidin-7-one;

8-Bicyclo[2.2.1]hept-5-en-2-yl-2-phenylamino-8H-pyrido[2,3-d]pyrimidin-7-one;

8-(1-Naphthalen-2-yl-ethyl)-2-phenylamino-8H-pyrido[2,3-d]pyrimidin-7-one;

8-(1-Methyl-2-phenyl-ethyl)-2-phenylamino-8H-pyrido[2,3-d]pyrimidin-7-one;

8-(2,5-Dimethyl-cyclohexyl)-2-phenylamino-8H-pyrido[2,3-d]pyrimidin-7-one;

8-(4-sec-Butyl-cyclohexyl)-2-phenylamino-8H-pyrido[2,3-d]pyrimidin-7-one;

8-Cyclohex-3-enyl-2-phenylamino-8H-pyrido[2,3-d]pyrimidin-7-one;

8-Indan-1-yl-2-phenylamino-8H-pyrido[2,3-d]pyrimidin-7-one;

8-(2-Isopropyl-5-methyl-cyclohexyl)-2-phenylamino-8H-pyrido[2,3-d]pyrimidin-7-one;

8-(1-Naphthalen-2-yl-ethyl)-2-phenylamino-8H-pyrido[2,3-d]pyrimidin-7-one;

8(2,6-Dimethyl-cyclohexyl)-2-phenylamino-8H-pyrido[2,3-d]pyrimidin-7-one;

8-(5-Isopropyl-2-methyl-cyclohexyl)-2-phenylamino-8H-pyrido[2,3-d]pyrimidin-7-one;

8-(1-Methyl-pent-2-ynyl)-2-phenylamino-8H-pyrido[2,3-d]pyrimidin-7-one;

8-Bicyclo[2.2.1]hept-2-yl-2-phenylamino-8H-pyrido[2,3-d]pyrimidin-7-one;

8-(1-Methyl-2,2-diphenyl-ethyl)-2-phenylamino-8H-pyrido[2,3-d]pyrimidin-7-one;

8-[1-(4-Methoxy-phenyl)-ethyl]-2-phenylamino-8H-pyrido[2,3-d]pyrimidin-7-one;

2-Phenylamino-8-(1,2,3,4-tetrahydro-naphthalen-2-yl)-8H-pyrido[2,3-d]pyrimidin-7-one;

2-Phenylamino-8-(1-p-tolyl-ethyl)-8H-pyrido[2,3-d]pyrimidin-7-one;

8-Adamantan-2-yl-2-phenylamino-8H-pyrido[2,3-d]pyrimidin-7-one;

8-(1-Methyl-but-3-ynyl)-2-phenylamino-8H-pyrido[2,3-d]pyrimidin-7-one;

8-Bicyclo[2.2.1]hept-2-yl-2-phenylamino-8H-pyrido[2,3-d]pyrimidin-7-one;

8-(1-Cyclohexyl-ethyl)-2-phenylamino-8H-pyrido[2,3-d]pyrimidin-7-one;

8-Dicyclohexylmethyl-2-phenylamino-8H-pyrido[2,3-d]pyrimidin-7-one;

2-Phenylamino-8-(phenyl-o-tolyl-methyl)-8H-pyrido[2,3-d]pyrimidin-7-one;

8-[1-(3,4-Dichloro-phenyl)-ethyl]-2-phenylamino-8H-pyrido[2,3-d]pyrimidin-7-one;

8-(1-Methyl-hexyl)-2-phenylamino-8H-pyrido[2,3-d]pyrimidin-7-one;

8-Indan-2-yl-2-phenylamino-8H-pyrido[2,3-d]pyrimidin-7-one;

8-[1-(2-Bromo-phenyl)ethyl]-2-phenylamino-8H-pyrido[2,3-d]pyrimidin-7-one;

8-(2-Methoxy-1-methyl-ethyl)-2-phenylamino-8H-pyrido[2,3-d]pyrimidin-7-one;

8-(1-Methyl-2-phenyl-ethyl)-2-phenylamino-8H-pyrido[2,3-d]pyrimidin-7-one;

8-(1-Ethyl-propyl)-2-phenylamino-8H-pyrido[2,3-d]pyrimidin-7-one;

8-(4-Isopropyl-cyclohexyl)-2-phenylamino-8H-pyrido[2,3-d]pyrimidin-7-one;

8-Acenaphthen-1-yl-2-phenylamino-8H-pyrido[2,3-d]pyrimidin-7-one;

8-(2-Oxo-cyclohexyl)-2-phenylamino-8H-pyrido[2,3-d]pyrimidin-7-one;

2-Phenylamino-8-(1,2,3,4-tetrahydro-naphthalen-1-yl)-8H-pyrido[2,3-d]pyrimidin-7-one;

8-(1-Methyl-heptyl)-2-phenylamino-8H-pyrido[2,3-d]pyrimidin-7-one;

2-Phenylamino-8-[phenyl-(2-trifluoromethyl-phenyl)-methyl]-8H-pyrido[2,3-d]pyrimidin-7-one;
2-Phenylamino-8-(1,7,7-trimethyl-bicyclo[2.2.1]hept-2-yl)-8H-pyrido[2,3-d]pyrimidin-7-one;
8-(1,1-Dioxo-tetrahydro-1-$\delta^6$-thiophen-3-yl)-2-phenylamino-8H-pyrido[2,3-d]pyrimidin-7-one;
8-(1-Biphenyl-4-yl-ethyl)-2-phenylamino-8H-pyrido[2,3-d]pyrimidin-7-one;
8-(3-Methyl-cyclohexyl)-2-phenylamino-8H-pyrido[2,3-d]pyrimidin-7-one;
8-Benzhydryl-2-phenylamino-8H-pyrido[2,3-d]pyrimidin-7-one;
2-Phenylamino-8-(9H-xanthen-9-yl)-8H-pyrido[2,3-d]pyrimidin-7-one;
8-(1-Pentyl-prop-2-ynyl)-2-phenylamino-8H-pyrido[2,3-d]pyrimidin-7-one;
8-(Octahydro-inden-5-yl)-2-phenylamino-8H-pyrido[2,3-d]pyrimidin-7-one;
2-Phenylamino-8-(2-phenyl-cyclohexyl)-8H-pyrido[2,3-d]pyrimidin-7-one;
8-(3,5-Dimethyl-cyclohexyl)-2-phenylamino-8H-pyrido[2,3-d]pyrimidin-7-one;
8-(4-tert-Butyl-cyclohexyl)-2-phenylamino-8H-pyrido[2,3-d]pyrimidin-7-one;
8-(2-Methyl-cyclohexyl)-2-phenylamino-8H-pyrido[2,3-d]pyrimidin-7-one;
8-[3-Phenoxy-1-(2-phenoxy-ethyl)-propyl]-2-phenylamino-8H-pyrido[2,3-d]pyrimidin-7-one;
8-(1-Cyclohexyl-propyl)-2-phenylamino-8H-pyrido[2,3-d]pyrimidin-7-one;
8-(1-Ethyl-prop-2-ynyl)-2-phenylamino-8H-pyrido[2,3-d]pyrimidin-7-one;
2-Phenylamino-8-(1-phenyl-heptyl)-8H-pyrido[2,3-d]pyrimidin-7-one;
8-[(4-Methoxy-phenyl)-pyridin-2-yl-methyl]-2-phenylamino-8H-pyrido[2,3-d]pyrimidin-7-one;
8-Bicyclohexyl4-yl-2-phenylamino-8H-pyrido[2,3-d]pyrimidin-7-one;
8-(4-Methyl-cyclohexyl)-2-phenylamino-8H-pyrido[2,3-d]pyrimidin-7-one;
8-Cyclohexyl-2-phenylamino-8H-pyrido[2,3-d]pyrimidin-7-one;
8-(Cyclohexyl-phenyl-methyl)-2-phenylamino-8H-pyrido[2,3-d]pyrimidin-7-one;
2-Phenylamino-8-(1-phenyl-propyl)-8H-pyrido[2,3-d]pyrimidin-7-one;
2-Phenylamino-8-(1-phenyl-prop-2-ynyl)-8H-pyrido[2,3-d]pyrimidin-7-one;
2-Phenylamino-8-(2-phenyl-[1,3]dioxan-5-yl)-8H-pyrido[2,3-d]pyrimidin-7-one;
2-Phenylamino-8-(2,2,2-trifluoro-1-trifluoromethyl-ethyl)-8H-pyrido[2,3-d]pyrimidin-7-one;
2-(7-Oxo-2-phenylamino-7H-pyrido[2,3-d]pyrimidin-8-yl)-propionitrile;
8-Cyclooctyl-2-phenylamino-8H-pyrido[2,3-d]pyrimidin-7-one;
8-(Decahydro-naphthalen-2-yl)-2-phenylamino-8H-pyrido[2,3-d]pyrimidin-7-one;
8-(9H-Fluoren-9-yl)-2-phenylamino-8H-pyrido[2,3-d]pyrimidin-7-one;
8-[4-(1,1-Dimethyl-propyl)cyclohexyl]-2-phenylamino-8H-pyrido[2,3-d]pyrimidin-7-one;
8-(10,11-Dihydro-5H-dibenzo[a,d]cyclohepten-5-yl)-2-phenylamino-8H-pyrido[2,3-d]pyrimidin-7-one;
2-Phenylamino-8-[2,2,2-trichloro-1-(4-fluoro-phenyl)-ethyl]-8H-pyrido[2,3-d]pyrimidin-7-one;
2-Phenylamino-8-(3,3,5-trimethyl-cyclohexyl)-8H-pyrido[2,3-d]pyrimidin-7-one;
8-(3-Phenoxy-benzyl)-2-(4-piperidin-1-yl-phenylamino)-8H-pyrido[2,3-]pyrimidin-7-one;
8-(2-Cyclopropyl-ethyl)-2-(4-piperidin-1-yl-phenylamino)-8H-pyrido[2,3-]pyrimidin-7-one;
8-(2-Naphthalen-2-yl-ethyl)-2-(4-piperidin-1-yl-phenylamino)-8H-pyrido[2,3-d]pyrimidin-7-one;
8-(3,5-Dimethoxy-benzyl)-2-(4-piperidin-1-yl-phenylamino)-8H-pyrido[2,3-d]pyrimidin-7-one;
8-Hex-2-ynyl-2-(4-piperidin-1-yl-phenylamino)-8H-pyrido[2,3-d]pyrimidin-7-one;
8-(4-Methylsulfanyl-benzyl)-2-(4-piperidin-1-yl-phenylamino)-8H-pyrido[2,3-d]pyrimidin-7-one;
8-(3,3-Dimethyl-butyl)-2-(4-piperidin-1-yl-phenylamino)-8H-pyrido[2,3-d]pyrimidin-7-one;
8-(2-Phenethyl-benzyl)-2-(4-piperidin-1-yl-phenylamino)-8H-pyrido[2,3-d]pyrimidin-7-one;
8-(2-Ethyl-hexyl)-2-(4-piperidin-1-yl-phenylamino)-8H-pyrido[2,3-d]pyrimidin-7-one;
8-Cyclohex-3-enylmethyl-2-(4-piperidin-1-yl-phenylamino)-8H-pyrido[2,3-d]pyrimidin-7-one;
8-Bicyclo[2.2.1]hept-2-ylmethyl-2-(4-piperidin-1-yl-phenylamino)-8H-pyrido[2,3-d]pyrimidin-7-one;
8(4Chloro-2-nitro-benzyl)-2-(4-piperidin-1-yl-phenylamino)-8H-pyrido[2,3-d]pyrimidin-7-one;
8-(3-Ethyl-oxetan-3-ylmethyl)-2-(4-piperidin-1-yl-phenylamino)-8H-—pyrido[2,3-d]pyrimidin-7-one;
8-[2-(2-Methoxy-ethoxy)-ethyl]-2-(4-piperidin-1-yl-phenylamino)-8H-pyrido[2,3-d]pyrimidin-7-one;
8-(2,2,3,3,3-Pentafluoro-propyl)-2-(4-piperidin-1-yl-phenylamino)-8H-pyrido[2,3-d]pyrimidin-7-one;
2-(4-Piperidin-1-yl-phenylamino)-8-(tetrahydro-furan-2-ylmethyl)-8H-pyrido[2,3-d]pyrimidin-7-one;
8-(3-Methyl-but-2-enyl)-2-(4-piperidin-1-yl-phenylamino)-8H-pyrido[2,3-]pyrimidin-7-one;
8-[2-(4-tert-Butyl-phenoxy)-ethyl]-2-(4-piperidin-1-yl-phenylamino)-8H-pyrido[2,3-d]pyrimidin-7-one;
8-(4-Ethyl-benzyl)-2-(4-piperidin-1-yl-phenylamino)-8H-pyrido[2,3-d]pyrimidin-7-one;
8-(2-Phenoxy-ethyl)-2-(4-piperidin-1-yl-phenylamino)-8H-pyrido[2,3-d]pyrimidin-7-one;
8-(2-Methyl-allyl)-2-(4-piperidin-1-yl-phenylamino)-8H-pyrido[2,3-d]pyrimidin-7-one;
8-(3-Methyl-benzyl)-2-(4-piperidin-1-yl-phenylamino)-8H-pyrido[2,3-d]pyrimidin-7-one;
8-(4-Methyl-benzyl)-2-(4-piperidin-1-yl-phenylamino)-8H-pyrido[2,3-d]pyrimidin-7one;
8-(2-Butoxy-ethyl)-2-(4-piperidin-1-yl-phenylamino)-8H-pyrido[2,3-d]pyrimidin-7-one;
2-(4-Piperidin-1-yl-phenylamino)-8-(2,2,2-trifluoro-ethyl)-8H-pyrido[2,3-d]pyrimidin-7-one;
2-(4-Piperidin-1-yl-phenylamino)-8-(2-thiophen-2-yl-ethyl)-8H-pyrido[2,3-d]pyrimidin-7-one;
8-Benzo[1,3]dioxol-5-ylmethyl-2-(4-piperidin-1-yl-phenylamino)-8H-pyrido[2,3-d]pyrimidin-7-one;
8-Cyclohexylmethyl-2-(4-piperidin-1-yl-phenylamino)-8H-pyrido[2,3-d]pyrimidin-7-one;
8(2-Ethoxy-ethyl)-2-(4-piperidin-1-yl-phenylamino)-8H-pyrido[2,3-d]pyrimidin-7-one;
2-(4-Piperidin-1-yl-phenylamino)-8-thiophen-2-ylmethyl-8H-pyrido[2,3-d]pyrimidin-7-one;
8-Furan-2-ylmethyl-2-(4-piperidin-1-yl-phenylamino)-8H-pyrido[2,3-d]pyrimidin-7-one;
8-(3-Phenyl-allyl)-2-(4-piperidin-1-yl-phenylamino)-8H-pyrido[2,3-d]pyrimidin-7-one;
8-Furan-3-ylmethyl-2-(4-piperidin-1-yl-phenylamino)-8H-pyrido[2,3-d]pyrimidin-7-one;
8-(3-Methoxy-propyl)-2-(4-piperidin-1-yl-phenylamino)-8H-pyrido[2,3-d]pyrimidin-7-one;

8-(3-Methyl-bicyclo[2.2.1]hept-2-ylmethyl)-2-(4-piperidin-1-yl-phenylamino)-8H-pyrido[2,3-d]pyrimidin-7-one;

8-(3-Phenyl-prop-2-ynyl)-2-(4-piperidin-1-yl-phenylamino)-8H-pyrido[2,3-d]pyrimidin-7-one;

8-(2-Methyl-3-oxo-butyl)-2-(4-piperidin-1-yl-phenylamino)-8H-pyrido[2,3-d]pyrimidin-7-one;

8-[Bis-(4-fluoro-phenyl)-methyl]-2-(4-piperidin-1-yl-phenylamino)-8H-pyrido[2,3-d]pyrimidin-7-one;

8-[Cyclopropyl-(4-fluoro-phenyl)-methyl]-2-(4-piperidin-1-yl-phenylamino)-8H-pyrido[2,3-d]pyrimidin-7-one;

8-(2-Isopropyl-cyclohexyl)-2-(4-piperidin-1-yl-phenylamino)-8H-pyrido[2,3-d]pyrimidin-7-one;

8-(2,2,3,3,4,4,5,5,6,6,7,7-Dodecafluoro-1,1-dimethyl-heptyl)-2-(4-piperidin-1-yl-phenylamino)-8H-pyrido[2,3-d]pyrimidin-7-one;

2-(4-Piperidin-1-yl-phenylamino)-8-(1,7,7-trimethyl-bicyclo[2.2.1]hept-2-yl)-8H-pyrido[2,3-d]pyrimidin-7-one;

2-(4-Piperidin-1-yl-phenylamino)-8-(2,2,2-trifluoro-1-phenyl-ethyl)-8H-pyrido[2,3-d]pyrimidin-7-one;

2-(4-Piperidin-1-yl-phenylamino)-8-(2,2,2-trichloro-1-phenyl-ethyl)-8H-pyrido[2,3-d]pyrimidin-7-one;

8-(2,3-Dimethyl-cyclohexyl)-2-(4-piperidin-1-yl-phenylamino)-8H-pyrido[2,3-d]pyrimidin-7-one;

2-(4-Piperidin-1-yl-phenylamino)-8-(tetrahydro-pyran-4-yl)-8H-pyrido[2,3-d]pyrimidin-7-one;

8-Cyclohex-2-enyl-2-(4-piperidin-1-yl-phenylamino)-8H-pyrido[2,3-d]pyrimidin-7-one;

2-(4-Piperidin-1-yl-phenylamino)-8-(1,3,3-trimethyl-bicyclo[2.2.1]hept-2-yl)-8H-pyrido[2,3-d]pyrimidin-7-one;

8-Bicyclo[2.2.1]hept-5-en-2-yl-2-(4-piperidin-1-yl-phenylamino)-8H-pyrido[2,3-d]pyrimidin-7-one;

8-(1-Naphthalen-2-yl-ethyl)-2-(4-piperidin-1-yl-phenylamino)-8H-pyrido[2,3-d]pyrimidin-7-one;

8-(1-Methyl-2-phenyl-ethyl)-2-(4-piperidin-1-yl-phenylamino)-8H-pyrido[2,3-d]pyrimidin-7-one;

8-(2,5-Dimethyl-cyclohexyl)-2-(4-piperidin-1-yl-phenylamino)-8H-pyrido[2,3-d]pyrimidin-7-one;

8-(4-sec-Butyl-cyclohexyl)-2-(4-piperidin-1-yl-phenylamino)-8H-pyrido[2,3-d]pyrimidin-7-one;

8Cyclohex-3-enyl-2-(4-piperidin-1-yl-phenylamino)-8H-pyrido[2,3-d]pyrimidin-7-one;

8-Indan-1-yl-2-(4-piperidin-1-yl-phenylamino)-8H-pyrido[2,3-d]pyrimidin-7-one;

8-(2-Isopropyl-5-methyl-cyclohexyl)-2-(4-piperidin-1-yl-phenylamino)-8H-pyrido[2,3-d]pyrimidin-7-one;

8-(1-Naphthalen-2-yl-ethyl)-2-(4-piperidin-1-yl-phenylamino)-8H-pyrido[2,3-d]pyrimidin-7-one;

8-(2,6-Dimethyl-cyclohexyl)-2-(4-piperidin-1-yl-phenylamino)-8H-pyrido[2,3-d]pyrimidin-7-one;

8-(5-Isopropyl-2-methyl-cyclohexyl)-2-(4piperidin-1-yl-phenylamino)-8H-pyrido[2,3-d]pyrimidin-7-one;

8-(1-Methyl-pent-2-ynyl)-2-(4-piperidin-1-yl-phenylamino)-8H-pyrido[2,3-d]pyrimidin-7-one;

8-Bicyclo[2.2.1]hept-2-yl-2-(4-piperidin-1-yl-phenylamino)-8H-pyrido[2,3-d]pyrimidin-7-one;

8-(1-Methyl-2,2-diphenyl-ethyl)-2-(4-piperidin-1-yl-phenylamino)-8H-pyrido[2,3-d]pyrimidin-7-one;

8-[1-(4-Methoxy-phenyl)-ethyl]-2-(4-piperidin-1-yl-phenylamino)-8H-pyrido[2,3-d]pyrimidin-7-one;

2-(4-Piperidin-1-yl-phenylamino)-8-(1,2,3,4-tetrahydro-naphthalen-2-yl)-8H-pyrido[2,3-d]pyrimidin-7-one;

2-(4-Piperidin-1-yl-phenylamino)-8-(1-p-tolyl-ethyl)-8H-pyrido[2,3-d]pyrimidin-7-one;

8-Adamantan-2-yl-2-(4-piperidin-1-yl-phenylamino)-8H-pyrido[2,3-d]pyrimidin-7-one;

8-(1-Methyl-but-3-ynyl)-2-(4-piperidin-1-yl-phenylamino)-8H-pyrido[2,3-d]pyrimidin-7-one;

8-Bicyclo[2.2.1]hept-2-yl-2-(4-piperidin-1-yl-phenylamino)-8H-pyrido[2,3-d]pyrimidin-7-one;

8-(1-Cyclohexyl-ethyl)-2-(4-piperidin-1-yl-phenylamino)-8H-pyrido[2,3-d]pyrimidin-7-one;

8-Dicyclohexylmethyl-2-(4-piperidin-1-yl-phenylamino)-8H-pyrido[2,3-d]pyrimidin-7-one;

8-(Phenyl-o-tolyl-methyl)-2-(4-piperidin-1-yl-phenylamino)-8H-pyrido[2,3-d]pyrimidin-7-one;

8-[1-(3,4-Dichloro-phenyl)-ethyl]-2-(4-piperidin-1-yl-phenylamino)-8H-pyrido[2,3-d]pyrimidin-7-one;

8-(1-Methyl-hexyl)-2-(4-piperidin-1-yl-phenylamino)-8H-pyrido[2,3-d]pyrimidin-7-one;

8-Indan-2-yl-2-(4-piperidin-1-yl-phenylamino)-8H-pyrido[2,3-d]pyrimidin-7-one;

8-[1-(2-Bromo-phenyl)-ethyl]-2-(4-piperidin-1-yl-phenylamino)-8H-pyrido[2,3-d]pyrimidin-7-one;

8-(2-Methoxy-1-methyl-ethyl)-2-(4-piperidin-1-yl-phenylamino)-8H-pyrido[2,3-d]pyrimidin-7-one;

8-(1-Methyl-2-phenyl-ethyl)-2-(4-piperidin-1-yl-phenylamino)-8H-pyrido[2,3-d]pyrimidin-7-one;

8-(1-Ethyl-propyl)-2-(4-piperidin-1-yl-phenylamino)-8H-pyrido[2,3-d]pyrimidin-7-one;

8-(4-Isopropyl-cyclohexyl)-2-(4-piperidin-1-yl-phenylamino)-8H-pyrido[2,3-d]pyrimidin-7-one;

8-Acenaphthen-1-yl-2-(4-piperidin-1-yl-phenylamino)-8H-pyrido[2,3-d]pyrimidin-7-one;

8-(2-Oxo-cyclohexyl)-2-(4-piperidin-1-yl-phenylamino)-8H-pyrido[2,3-d]pyrimidin-7-one;

2-(4-Piperidin-1-yl-phenylamino)-8-(1,2,3,4-tetrahydro-naphthalen-1-yl)-8H-pyrido[2,3-d]pyrimidin-7-one;

8-(1-Methyl-heptyl)-2-(4-piperidin-1-yl-phenylamino)-8H-pyrido[2,3-d]pyrimidin-7-one;

8-[Phenyl-(2-trifluoromethyl-phenyl)-methyl]-2-(4-piperidin-1-yl-phenylamino)-8H-pyrido[2,3-d]pyrimidin-7-one;

2-(4-Piperidin-1-yl-phenylamino)-8-(1,7,7-trimethyl-bicyclo[2.2.1]hept-2-yl)-8H-pyrido[2,3-d]pyrimidin-7-one;

8-(1,1-Dioxo-tetrahydro-$\delta^6$-thiophen-3-yl)-2-(4-piperidin-1-yl-phenylamino)-8H-pyrido[2,3-d]pyrimidin-7-one;

8-(1-Biphenyl-4-yl-ethyl)-2-(4-piperidin-1-yl-phenylamino)-8H-pyrido[2,3-d]pyrimidin-7-one;

8-(3-Methyl-cyclohexyl)-2-(4-piperidin-1-yl-phenylamino)-8H-pyrido[2,3-d]pyrimidin-7-one;

8-Benzhydryl-2-(4-piperidin-1-yl-phenylamino)-8H-pyrido[2,3-d]pyrimidin-7-one;

2-(4-Piperidin-1-yl-phenylamino)-8-(9H-xanthen-9-yl)-8H-pyrido[2,3-d]pyrimidin-7-one;

8-(1-Pentyl-prop-2-ynyl)-2-(4-piperidin-1-yl-phenylamino)-8H-pyrido[2,3-d]pyrimidin-7-one;

8-(Octahydro-inden-5-yl)-2-(4piperidin-1-yl-phenylamino)-8H-pyrido[2,3-d]pyrimidin-7-one;

8-(2-Phenyl-cyclohexyl)-2-(4-piperidin-1-yl-phenylamino)-8H-pyrido[2,3-d]pyrimidin-7-one;

8-(3,5-Dimethyl-cyclohexyl)-2-(4-piperidin-1-yl-phenylamino)-8H-pyrido[2,3-d]pyrimidin-7-one;

8-(4-tert-Butyl-cyclohexyl)-2-(4-piperidin-1-yl-phenylamino)-8H-pyrido[2,3-d]pyrimidin-7-one;

8-(2-Methyl-cyclohexyl)-2-(4-piperidin-1-yl-phenylamino)-8H-pyrido[2,3-d]pyrimidin-7-one;

8-[3-Phenoxy-1-(2-phenoxy-ethyl)-propyl]-2-(4-piperidin-1-yl-phenylamino)-8H-pyrido[2,3-d]pyrimidin-7-one;

8-(1-Cyclohexyl-propyl)-2-(4-piperidin-1-yl-phenylamino)-8H-pyrido[2,3-d]pyrimidin-7-one;

8-(1-Ethyl-prop-2-ynyl)-2-(4-piperidin-1-yl-phenylamino)-8H-pyrido[2,3-d]pyrimidin-7-one;

8-(1-Phenyl-heptyl)-2-(4-piperidin-1-yl-phenylamino)-8H-pyrido[2,3-d]pyrimidin-7-one;
8-[(4-Methoxy-phenyl)-pyridin-2-yl-methyl]-2-(4-piperidin-1-yl-phenylamino)-8H-pyrido[2,3-d]pyrimidin-7-one;
8-Bicyclohexyl-4-yl-2-(4-piperidin-1-yl-phenylamino)-8H-pyrido[2,3-d]pyrimidin-7-one;
8-(4-Methyl-cyclohexyl)-2-(4-piperidin-1-yl-phenylamino)-8H-pyrido[2,3-d]pyrimidin-7-one;
8-Cyclohexyl-2-(4-piperidin-1-yl-phenylamino)-8H-pyrido[2,3-d]pyrimidin-7-one;
8-(Cyclohexyl-phenyl-methyl)-2-(4-piperidin-1-yl-phenylamino)-8H-pyrido[2,3-d]pyrimidin-7-one;
8-(1-Phenyl-propyl)-2-(4-piperidin-1-yl-phenylamino)-8H-pyrido[2,3-d]pyrimidin-7-one;
8-(1-Phenyl-prop-2-ynyl)-2-(4-piperidin-1-yl-phenylamino)-8H-pyrido[2,3-d]pyrimidin-7-one;
8-(2-Phenyl-[1,3]dioxan-5-yl)-2-(4-piperidin-1-yl-phenylamino)-8H-pyrido[2,3-d]pyrimidin-7-one;
2-(4-Piperidin-1-yl-phenylamino)-8-(2,2,2-trifluoro-1-trifluoromethyl-ethyl)-8H-pyrido[2,3-d]pyrimidin-7-one;
2-[7-Oxo-2-(4-piperidin-1-yl-phenylamino)-7H-pyrido[2,3-d]pyrimidin-8-yl]-propionitrile;
8-Cyclooctyl-2-(4-piperidin-1-yl-phenylamino)-8H-pyrido[2,3-d]pyrimidin-7-one;
8Decahydro-naphthalen-2-yl)-2-(4-piperidin-1-yl-phenylamino)-8H-pyrido[2,3-d]pyrimidin-7-one;
8-(9H-Fluoren-9-yl)-2-(4-piperidin-1-yl-phenylamino)-8H-pyrido[2,3-d]pyrimidin-7-one;
8-[4-(1,1-Dimethyl-propyl)-cyclohexyl]-2-(4-piperidin-1-yl-phenylamino)-8H-pyrido[2,3-d]pyrimidin-7-one;
8(10,11-Dihydro-5H-dibenzo[a,d]cyclohepten-5-yl)-2-(4-piperidin-1-yl-phenylamino)-8H-pyrido[2,3-d]pyrimidin-7-one;
2-(4-Piperidin-1-yl-phenylamino)-8-[2,2,2-trichloro-1-(4-fluoro-phenyl)-ethyl]-8H-pyrido[2,3-d]pyrimidin-7-one;
2-(4-Piperidin-1-yl-phenylamino)-8-(3,3,5-triethyl-cyclohexyl)-8H-pyrido[2,3-d]pyrimidin-7-one;
2-[4-(4-Methyl-piperazin-1-yl)-phenylamino]-8-(3-phenoxy-benzyl)-8H-pyrido[2,3-d]pyrimidin-7-one;
8-(2-Cyclopropyl-ethyl)-2-[4-(4-methyl-piperazin-1-yl)-phenylamino]-8H-pyrido[2,3-d]pyrimidin-7-one;
2-[4-(4-Methyl-piperazin-1-yl)-phenylamino]-8-(2-naphthalen-2-yl-ethyl)-8H-pyrido[2,3-d]pyrimidin-7-one;
8-(3,5-Dimethoxy-benzyl)-2-[4-(4-methyl-piperazin-1-yl)-phenylamino]-8H-pyrido[2,3-d]pyrimidin-7-one;
8-Hex-2-ynyl-2-[4-(4-methyl-piperazin-1-yl)-phenylamino]-8H-pyrido[2,3-d]pyrimidin-7-one;
2-[4-(4-Methyl-piperazin-1-yl)-phenylamino]-8-(4-methylsulfanyl-benzyl)-8H-pyrido[2,3-d]pyrimidin-7-one;
2-[4-(4-Methyl-piperazin-1-yl)-phenylamino]-8-(4-methylsulfanyl-benzyl)-8H-pyrido[2,3-d]pyrimidin-7-one;
8-(3,3-Dimethyl-butyl)-2-[4-(4-methyl-piperazin-1-yl)-phenylamino]-8H-pyrido[2,3-d]pyrimidin-7-one;
2-[4-(4-Methyl-piperazin-1-yl)-phenylamino]-8-(2-phenethyl-benzyl)-8H-pyrido[2,3-d]pyrimidin-7-one;
8-(2-Ethyl-hexyl)-2-[4(4-methyl-piperazin-1-yl)-phenylamino]-8H-pyrido[2,3-d]pyrimidin-7-one;
8-Cyclohex-3-enylmethyl-2-[4-(4-methyl-piperazin-1-yl)-phenylamino]-8H-pyrido[2,3-d]pyrimidin-7-one;
8-Bicyclo[2.2.1]hept-2-ylmethyl-2-[4-(4-methyl-piperazin-1-yl)-phenylamino]-8H-pyrido[2,3-d]pyrimidin-7-one;
8-(4-Chloro-2-nitro-benzyl)-2-[4-(4-methyl-piperazin-1-yl)-phenylamino]-8H-pyrido[2,3-d]pyrimidin-7-one;
8-(3-Ethyl-oxetan-3-ylmethyl)-2-[4-(4-methyl-piperazin-1-yl)-phenylamino]-8H-pyrido[2,3-d]pyrimidin-7-one;
8-[2-(2-Methoxy-ethoxy)-ethyl]-2-[4-(4-methyl-piperazin-1-yl)-phenylamino]-8H-pyrido[2,3-d]pyrimidin-7-one;
2-[4-(4-Methyl-piperazin-1-yl)-phenylamino]-8-(2,2,3,3,3-pentafluoro-propyl)-8H-pyrido[2,3-d]pyrimidin-7-one;
2-[4-(4-Methyl-piperazin-1-yl)-phenylamino]-8-(tetrahydro-furan-2-ylmethyl)-8H-pyrido[2,3-d]pyrimidin-7-one;
8-(3-Methyl-but-2-enyl)-2-[4-(4-methyl-piperazin-1-yl)-phenylamino]-8H-pyrido[2,3-d]pyrimidin-7-one;
8-[2-(4-tert-Butyl-phenoxy)-ethyl]-2-[4-(4-methyl-piperazin-1-yl)-phenylamino]-8H-pyrido[2,3-d]pyrimidin-7-one;
8-(4-Ethyl-benzyl)-2-[4-(4-methyl-piperazin-1-yl)-phenylamino]-8H-pyrido[2,3-d]pyrimidin-7-one;
2-[4-(4-Methyl-piperazin-1-yl)-phenylamino]-8-(2-phenoxy-ethyl)-8H-pyrido[2,3-d]pyrimidin-7-one;
8-(2-Methyl-allyl)-2-[4-(4-methyl-piperazin-1-yl)-phenylamino]-8H-pyrido[2,3-d]pyrimidin-7-one;
8-(3-Methyl-benzyl)-2-[4-(4-methyl-piperazin-1-yl)-phenylamino]-8H-pyrido[2,3-d]pyrimidin-7-one;
8-(4-Methyl-benzyl)-2-[4-(4-methyl-piperazin-1-yl)-phenylamino]-8H-pyrido[2,3-d]pyrimidin-7-one;
8-(2-Butoxy-ethyl)-2-[4-(4-methyl-piperazin-1-yl)-phenylamino]-8H-pyrido[2,3-d]pyrimidin-7-one;
2-[4(4-Methyl-piperazin-1-yl)-phenylamino]-8-(2,2,2-trifluoro-ethyl)-8H-pyrido[2,3-d]pyrimidin-7-one;
2-[4-(4-Methyl-piperazin-1-yl)-phenylamino]-8-(2-thiophen-2-yl-ethyl)-8H-pyrido[2,3-d]pyrimidin-7-one;
8-Benzo[1,3]dioxol-5-ylmethyl-2-[4-(4-methyl-piperazin-1-yl)-phenylamino]-8H-pyrido[2,3-d]pyrimidin-7-one;
8-Cyclohexylmethyl-2-[4-(4-methyl-piperazin-1-yl)-phenylamino]-8H-pyrido[2,3-d]pyrimidin-7-one;
8-(2-Ethoxy-ethyl)-2-[4-(4-methyl-piperazin-1-yl)-phenylamino]-8H-pyrido[2,3-d]pyrimidin-7-one;
2-[4-(4-Methyl-piperazin-1-yl)-phenylamino]-8-thiophen-2-ylmethyl-8H-pyrido[2,3-d]pyrimidin-7-one;
8-Furan-2-ylmethyl-2-[4-(4-methyl-piperazin-1-yl)-phenylamino]-8H-pyrido[2,3-d]pyrimidin-7-one;
2-[4-(4-Methyl-piperazin-1-yl)-phenylamino]-8-(3-phenyl-allyl)-8H-pyrido[2,3-d]pyrimidin-7-one;
8-Furan-3-ylmethyl-2-[4-(4-methyl-piperazin-1-yl)-phenylamino]-8H-pyrido[2,3-d]pyrimidin-7-one;
8-(3-Methoxy-propyl)-2-[4-(4-methyl-piperazin-1-yl)-phenylamino]-8H-pyrido[2,3-d]pyrimidin-7-one;
8-(3-Methyl-bicyclo[2.2.1]hept-2-ylmethyl)-2-[4-(4-methyl-piperazin-1-yl)-phenylamino]-8H-pyrido[2,3-d]pyrimidin-7-one;
2-[4-(4-Methyl-piperazin-1-yl)-phenylamino]-8-(3-phenyl-prop-2-ynyl)-8H-pyrido[2,3-d]pyrimidin-7-one;
8(2-Methyl-3-oxo-butyl)-2-[4-(4-methyl-piperazin-1-yl)-phenylamino]-8H-pyrido[2,3-d]pyrimidin-7-one;
8-[Bis-(4-fluoro-phenyl)-methyl]-2-[4-(4-methyl-piperazin-1-yl)-phenylamino]-8H-pyrido[2,3-d]pyrimidin-7-one;
8-[Cyclopropyl-(4-fluoro-phenyl)-methyl]-2-[4-(4-methyl-piperazin-1-yl)-phenylamino]-8H-pyrido[2,3-d]pyrimidin-7-one;
8-(2-Isopropyl-cyclohexyl)-2-[4-(4-methyl-piperazin-1-yl)-phenylamino]-8H-pyrido[2,3-d]pyrimidin-7-one;
8-(2,2,3,3,4,4,5,5,6,6,7,7-Dodecafluoro-1,1-dimethyl-heptyl)-2-[4-(4-methyl-piperazin-1-yl)-phenylamino]-8H-pyrido[2,3-d]pyrimidin-7-one;
2-[4-(4-Methyl-piperazin-1-yl)-phenylamino]-8-(1,7,7-trimethyl-bicyclo[2.2.1]hept-2-yl)-8H-pyrido[2,3-d]pyrimidin-7-one;
2-[4-(4-Methyl-piperazin-1-yl)-phenylamino]-8-(2,2,2-trifluoro-1-phenyl-ethyl)-8H-pyrido[2,3-d]pyrimidin-7-one;

2-[4-(4-Methyl-piperazin-1-yl)-phenylamino]-8-(2,2,2-trichloro-1-phenyl-ethyl)-8H-pyrido[2,3-d]pyrimidin-7-one;

8-(2,3-Dimethyl-cyclohexyl)-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-(tetrahydro-pyran-4-yl)-8H-pyrido[2,3-d]pyrimidin-7-one;

8-Cyclohex-2-enyl-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-(1,3,3-trimethyl-bicyclo[2.2.1]hept-2-yl)-8H-pyrido[2,3-d]pyrimidin-7-one;

8-Bicyclo[2.2.1]hept-5-en-2-yl-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-(1-naphthalen-2-yl-ethyl)-8H-pyrido[2,3-d]pyrimidin-7-one;

8-(1-Methyl-2-phenyl-ethyl)-2-[4-(4-methyl-piperazin-1-yl)-phenylamino]-8H-pyrido[2,3-d]pyrimidin-7-one;

8-(2,5-Dimethyl-cyclohexyl)-2-[4-(4-methyl-piperazin-1-yl)-phenylamino]-8H-pyrido[2,3-d]pyrimidin-7-one;

8-(4-sec-Butyl-cyclohexyl)-2-[4-(4-methyl-piperazin-1-yl)-phenylamino]-8H-pyrido[2,3-d]pyrimidin-7-one;

8-Cyclohex-3-enyl-2-[4-(4-methyl-piperazin-1-yl)-phenylamino]-8H-pyrido[2,3-d]pyrimidin-7-one;

8-Indan-1-yl-2-[4-(4-methyl-piperazin-1-yl)-phenylamino]-8H-pyrido[2,3-d]pyrimidin-7-one;

8-(2-Isopropyl-5-methyl-cyclohexyl)-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-(1-naphthalen-2-yl-ethyl)-8H-pyrido[2,3-d]pyrimidin-7-one;

8-(2,6-Dimethyl-cyclohexyl)-2-[4-(4-methyl-piperazin-1-yl)-phenylamino]-8H-pyrido[2,3-d]pyrimidin-7-one;

8-(5-Isopropyl-2-methyl-cyclohexyl)-2-[4-(4-methyl-piperazin-1-yl)-phenylamino]-8H-pyrido[2,3-d]pyrimidin-7-one;

8-(1-Methyl-pent-2-ynyl)-2-[4-(4-methyl-piperazin-1-yl)-phenylamino]-8H-pyrido[2,3-d]pyrimidin-7-one;

8-Bicyclo[2.2.1]hept-2-yl-2-[4-(4-methyl-piperazin-1-yl)-phenylamino]-8H-pyrido[2,3-d]pyrimidin-7-one;

8-(1-Methyl-2,2-diphenyl-ethyl)-2-[4-(4-methyl-piperazin-1-yl)-phenylamino]-8H-pyrido[2,3-d]pyrimidin-7-one;

8-[1-(4-Methoxy-phenyl)-ethyl]-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-(1,2,3,4-tetrahydro-naphthalen-2-yl)-8H-pyrido[2,3-d]pyrimidin-7-one;

2-[4-(4-Methyl-piperazin-1-yl)-phenylamino]-8-(1-p-tolyl-ethyl)-8H-pyrido[2,3-d]pyrimidin-7-one;

8-Adamantan-2-yl-2-[4-(4-methyl-piperazin-1-yl)-phenylamino]-8H-pyrido[2,3-d]pyrimidin-7-one;

8-(1-Methyl-but-3-ynyl)-2-[4-(4-methyl-piperazin-1-yl)-phenylamino]-8H-pyrido[2,3-d]pyrimidin-7-one;

8-Bicyclo[2.2.1]hept-2-yl-2-[4-(4-methyl-piperazin-1-yl)-phenylamino]-8H-pyrido[2,3-d]pyrimidin-7-one;

8-(1-Cyclohexyl-ethyl)-2-[4-(4-methyl-piperazin-1-yl)-phenylamino]-8H-pyrido[2,3-d]pyrimidin-7-one;

8-Dicyclohexylmethyl-2-[4-(4-methyl-piperazin-1-yl)-phenylamino]-8H-pyrido[2,3]pyrimidin-7-one;

2-[4-(4-Methyl-piperazin-1-yl)-phenylamino]-8-(phenyl-o-tolyl-methyl)-8H-pyrido[2,3-d]pyrimidin-7-one;

8-[1-(3,4-Dichloro-phenyl)-ethyl]-2-[4-(4-methyl-piperazin-1-yl)-phenylamino]-8H-pyrido[2,3-d]pyrimidin-7-one;

8-(1-Methyl-hexyl)-2-[4-(4-methyl-piperazin-1-yl)-phenylamino]-8H-pyrido[2,3-d]pyrimidin-7-one;

8-Indan-2-yl-2-[4-(4-methyl-piperazin-1-yl)-phenylamino]-8H-pyrido[2,3-d]pyrimidin-7-one;

8-[1-(2-Bromo-phenyl)-ethyl]-2-[4-(4-methyl-piperazin-1-yl)-phenylamino]-8H-pyrido[2,3-d]pyrimidin-7-one;

8-(2-Methoxy-1-methyl-ethyl)-2-[4-(4-methyl-piperazin-1-yl)-phenylamino]-8H-pyrido[2,3-d]pyrimidin-7-one;

8(1-Methyl-2-phenyl-ethyl)-2-[4-(4-methyl-piperazin-1-yl)-phenylamino]-8H-pyrido[2,3-d]pyrimidin-7-one;

8-(1-Ethyl-propyl)-2-[4-(4-methyl-piperazin-1-yl)-phenylamino]-8H-pyrido[2,3-d]pyrimidin-7-one;

8-(4-Isopropyl-cyclohexyl)-2-[4-(4-methyl-piperazin-1-yl)-phenylamino]-8H-pyrido[2,3-d]pyrimidin-7-one;

8-Acenaphthen-1-yl-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-(2-oxo-cyclohexyl)-8H-pyrido[2,3-d]pyrimidin-7-one;

2-[4-(4-Methyl-piperazin-1-yl)-phenylamino]-8-(1,2,3,4-tetrahydro-naphthalen-1-yl)-8H-pyrido[2,3-d]pyrimidin-7-one;

8-(1-Methyl-heptyl)-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-[phenyl-(2-trifluoromethyl-phenyl)-methyl]-8H-pyrido[2,3-d]pyrimidin-7-one;

2-[4-(4-Methyl-piperazin-1-yl)-phenylamino]-8-(1,7,7-trimethyl-bicyclo[2.2.1]hept-2-yl)-8H-pyrido[2,3-d]pyrimidin-7-one;

8-(1,1-Dioxo-tetrahydro-$\delta^6$-thiophen-3-yl)-2-[4-(4-methyl-piperazin-1-yl)-phenylamino]-8H-pyrido[2,3-d]pyrimidin-7-one;

8-(1-Bipheny-4-yl-ethyl)-2-[4-(4-methyl-piperazin-1-yl)-phenylamino]-8H-pyrido[2,3-d]pyrimidin-7-one;

8-(3-Methyl-cyclohexyl)-2-[4-(4-methyl-piperazin-1-yl)-phenylamino]-8H-pyrido[2,3-d]pyrimidin-7-one;

8-Benzhydryl-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-(9H-xanthen-9-yl)-8H-pyrido[2,3-d]pyrimidin-7-one;

2-[4-(4-Methyl-piperazin-1-yl)-phenylamino]-8-(1-pentyl-prop-2-ynyl)-8H-pyrido[2,3-d]pyrimidin-7-one;

2-[4-(4-Methyl-piperazin-1-yl)-phenylamino]-8-(octahydro-inden-5-yl)-8H-pyrido[2,3-d]pyrimidin-7-one;

2-[4-(4-Methyl-piperazin-1-yl)-phenylamino]-8-(2-phenyl-cyclohexyl)-8H-pyrido[2,3-d]pyrimidin-7-one;

8-(3,5-Dimethyl-cyclohexyl)-2-[4-(4-methyl-piperazin-1-yl)-phenylamino]-8H-pyrido[2,3-d]pyrimidin-7-one;

8-(4-tert-Butyl-cyclohexyl)-2-[4-(4-methyl-piperazin-1-yl)-phenylamino]-8H-pyrido[2,3-d]pyrimidin-7-one;

8-(2-Methyl-cyclohexyl)-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-[3-phenoxy-1-(2-phenoxy-ethyl)-propyl]-8H-pyrido[2,3-d]pyrimidin-7-one;

8-(1-Cyclohexyl-propyl)-2-[4-(4-methyl-piperazin-1-yl)-phenylamino]-8H-pyrido[2,3-d]pyrimidin-7-one;

8-(1-Ethyl-prop-2-ynyl)-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-(1-phenyl-heptyl)-8H-pyrido[2,3-d]pyrimidin-7-one;

8-[(4-Methoxy-phenyl)-pyridin-2-yl-methyl]-2-[4-(4-methyl-piperazin-1-yl)-phenylamino]-8H-pyrido[2,3-d]pyrimidin-7-one;

8-Bicyclohexylyl-2-[4-(4-methyl-piperazin-1-yl)-phenylamino]-8H-pyrido[2,3-d]pyrimidin-7-one;

8-(4-Methyl-cyclohexyl)-2-[4-(4-methyl-piperazin-1-yl)-phenylamino]-8H-pyrido[2,3-d]pyrimidin-7-one;

8-Cyclohexyl-2-[4-(4-methyl-piperazin-1-yl)-phenylamino]-8H-pyrido[2,3-d]pyrimidin-7-one;

8-(Cyclohexyl-phenyl-methyl)-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-(1-phenyl-propyl)-8H-pyrido[2,3-d]pyrimidin-7-one;

2-[4-(4-Methyl-piperazin-1-yl)-phenylamino]-8-(1-phenyl-prop-2-ynyl)-8H-pyrido[2,3-d]pyrimidin-7-one;

2-[4-(4-Methyl-piperazin-1-yl)-phenylamino]-8-(2-phenyl-[1,3]dioxan-5-yl)-8H-pyrido[2,3-d]pyrimidin-7-one;

2-[4-(4-Methyl-piperazin-1-yl)-phenylamino]-8-(2,2,2-trifluoro-1-trifluoromethyl-ethyl)-8H-pyrido[2,3-d]pyrimidin-7-one;

2-{2-[4-(4-Methyl-piperazin-1-yl)-phenylamino]-7-oxo-7H-pyrido[2,3-d]pyrimidin-8-yl}-propionitrile;

8-Cyclooctyl-2-[4-(4-methyl-piperazin-1-yl)-phenylamino]-8H-pyrido[2,3-d]pyrimidin-7-one;

8-(Decahydro-naphthalen-2-yl)-2-[4-(4-methyl-piperazin-1-yl)-phenylamino]-8H-pyrido[2,3-d]pyrimidin-7-one;

8-(9H-Fluoren-9-yl)-2-[4-(4-methyl-piperazin-1-yl)-phenylamino]-8H-pyrido[2,3-d]pyrimidin-7-one;

8-[4-(1,1-Dimethyl-propyl)-cyclohexyl]-2-[4-(4-methyl-piperazin-1-yl)-phenylamino]-8H-pyrido[2,3-d]pyrimidin-7-one;

8-(10,11-Dihydro-5H-dibenzo[a,d]cyclohepten-5-yl)-2-[4-(4-methyl-piperazin-1-yl)-phenylamino]-8H-pyrido[2,3-d]pyrimidin-7-one;

2-[4-(4-Methyl-piperazin-1-yl)-phenylamino]-8-[2,2,2-trichloro-1-(4-fluoro-phenyl)-ethyl]-8H-pyrido[2,3-d]pyrimidin-7-one;

2-[4-(4-Methyl-piperazin-1-yl)-phenylamino]-8-(3,3,5-trimethyl-cyclohexyl)-8H-pyrido[2,3-d]pyrimidin-7-one;

8-(3-Phenoxy-benzyl)-2-(4-pyrazol-1-yl-phenylamino)-8H-pyrido[2,3-d]pyrimidin-7-one;

8-(2-Cyclopropyl-ethyl)-2-(4-pyrazol-1-yl-phenylamino)-8H-pyrido[2,3-d]pyrimidin-7-one;

8-(2-Naphthalen-2-yl-ethyl)-2-(4-pyrazol-1-yl-phenylamino)-8H-pyrido[2,3-d]pyrimidin-7-one;

8-(3,5-Dimethoxy-benzyl)-2-(4-pyrazol-1-yl-phenylamino)-8H-pyrido[2,3-d]pyrimidin-7-one;

8-Hex-2-ynyl-2-(4-pyrazol-1-yl-phenylamino)-8H-pyrido[2,3-d]pyrimidin-7-one;

8-(4-Methylsulfanyl-benzyl)-2-(4-pyrazol-1-yl-phenylamino)-8H-pyrido[2,3-d]pyrimidin-7-one;

8-(3,3-Dimethyl-butyl)-2-(4-pyrazol-1-yl-phenylamino)-8H-pyrido[2,3-d]pyrimidin-7-one;

8-(2-Phenethyl-benzyl)-2-(4-pyrazol-1-yl-phenylamino)-8H-pyrido[2,3-d]pyrimidin-7-one;

8-(2-Ethyl-hexyl)-2-(4-pyrazol-1-yl-phenylamino)-8H-pyrido[2,3-d]pyrimidin-7-one;

8-Cyclohex-3-enylmethyl-2-(4-pyrazol-1-yl-phenylamino)-8H-pyrido[2,3-d]pyrimidin-7-one;

8-Bicyclo[2.2.1]hept-2-ylmethyl-2-(4-pyrazol-1-yl-phenylamino)-8H-pyrido[2,3-d]pyrimidin-7-one;

8-(4-Chloro-2-nitro-benzyl)-2-(4-pyrazol-1-yl-phenylamino)-8H-pyrido[2,3-d]pyrimidin-7-one;

8-(3-Ethyl-oxetan-3-ylmethyl)-2-(4-pyrazol-1-yl-phenylamino)-8H-pyrido[2,3-d]pyrimidin-7-one;

8-[2-(2-Methoxy-ethoxy)-ethyl]-2-(4-pyrazol-1-yl-phenylamino)-8H-pyrido[2,3-d]pyrimidin-7-one;

8-(2,2,3,3,3-Pentafluoro-propyl)-2-(4-pyrazol-1-yl-phenylamino)-8H-pyrido[2,3-d]pyrimidin-7-one;

2-(4-Pyrazol-1-yl-phenylamino)-8-(tetrahydro-furan-2-ylmethyl)-8H-pyrido[2,3-d]pyrimidin-7-one;

8-(3-Methyl-but-2-enyl)-2-(4-pyrazol-1-yl-phenylamino)-8H-pyrido[2,3-d]pyrimidin-7-one;

8-[2-(4-tert-Butyl-phenoxy)-ethyl]-2-(4-pyrazol-1-yl-phenylamino)-8H-pyrido[2,3-d]pyrimidin-7-one;

8-(4-Ethyl-benzyl)-2-(4-pyrazol-1-yl-phenylamino)-8H-pyrido[2,3-d]pyrimidin-7-one;

8-(2-Phenoxy-ethyl)-2-(4-pyrazol-1-yl-phenylamino)-8H-pyrido[2,3]pyrimidin-7-one;

8-(2-Methyl-allyl)-2-(4-pyrazol-1-yl-phenylamino)-8H-pyrido[2,3-d]pyrimidin-7-one;

8-(3-Methyl-benzyl)-2-(4-pyrazol-1-yl-phenylamino)-8H-pyrido[2,3-d]pyrimidin-7-one;

8-(4-Methyl-benzyl)-2-(4-pyrazol-1-yl-phenylamino)-8H-pyrido[2,3-d]pyrimidin-7-one;

8-(2-Butoxy-ethyl)-2-(4-pyrazol-1-yl-phenylamino)-8H-pyrido[2,3-d]pyrimidin-7-one;

2-(4-Pyrazol-1-yl-phenylamino)-8-(2,2,2-trifluoro-ethyl)-8H-pyrido[2,3-d]pyrimidin-7-one;

2-(4-Pyrazol-1-yl-phenylamino)-8-(2-thiophen-2-yl-ethyl)-8H-pyrido[2,3-d]pyrimidin-7-one;

8-Benzo[1,3]dioxol-5-ylmethyl-2-(4-pyrazol-1-yl-phenylamino)-8H-pyrido[2,3-d]pyrimidin-7-one;

8-Cyclohexylmethyl-2-(4-pyrazol-1-yl-phenylamino)-8H-pyrido[2,3-d]pyrimidin-7-one;

8-(2-Ethoxy-ethyl)-2-(4-pyrazol-1-yl-phenylamino)-8H-pyrido[2,3-d]pyrimidin-7-one;

2-(4-Pyrazol-1-yl-phenylamino)-8-thiophen-2-ylmethyl-8H-pyrido[2,3-d]pyrimidin-7-one;

8-Furan-2-ylmethyl-2-(4-pyrazol-1-yl-phenylamino)-8H-pyrido[2,3-d]pyrimidin-7-one;

8-(3-Phenyl-allyl)-2-(4-pyrazol-1-yl-phenylamino)-8H-pyrido[2,3-d]pyrimidin-7-one;

8-Furan-3-ylmethyl-2-(4-pyrazol-1-yl-phenylamino)-8H-pyrido[2,3-d]pyrimidin-7-one;

8-(3-Methoxy-propyl)-2-(4-pyrazol-1-yl-phenylamino)-8H-pyrido[2,3-d]pyrimidin-7-one;

8-(3-Methyl-bicyclo[2.2.1]hept-2-ylmethyl)-2-(4-pyrazol-1-yl-phenylamino)-8H-pyrido[2,3-d]pyrimidin-7-one;

8-(3-Phenyl-prop-2-ynyl)-2-(4-pyrazol-1-yl-phenylamino)-8H-pyrido[2,3-d]pyrimidin-7-one;

8-(2-Methyl-3-oxo-butyl)-2-(4-pyrazol-1-yl-phenylamino)-8H-pyrido[2,3-d]pyrimidin-7-one;

8-[Bis-(4-fluoro-phenyl)-methyl]-2-(4-pyrazol-1-yl-phenylamino)-8H-pyrido[2,3-d]pyrimidin-7-one;

8-[Cyclopropyl-(4-fluoro-phenyl)-methyl]-2-(4-pyrazol-1-yl-phenylamino)-8H-pyrido[2,3-d]pyrimidin-7-one;

8-(2-Isopropyl-cyclohexyl)-2-(4-pyrazol-1-yl-phenylamino)-8H-pyrido[2,3-d]pyrimidin-7-one;

8-(2,2,3,3,4,4,5,5,6,6,7,7-Dodecafluoro-1,1-dimethyl-heptyl)-2-(4-pyrazol-1-yl-phenylamino)-8H-pyrido[2,3-d]pyrimidin-7-one;

2-(4-Pyrazol-1-yl-phenylamino)-8-(1,7,7-trimethyl-bicyclo[2.2.1]hept-2-yl)-8H-pyrido[2,3-d]pyrimidin-7-one;

2-(4-Pyrazol-1-yl-phenylamino)-8-(2,2,2-trifluoro-1-phenyl-ethyl)-8H-pyrido[2,3-d]pyrimidin-7-one;

2-(4-Pyrazol-1-yl-phenylamino)-8-(2,2,2-trichloro-1-phenyl-ethyl)-8H-pyrido[2,3-d]pyrimidin-7-one;

8-(2,3-Dimethyl-cyclohexyl)-2-(4-pyrazol-1-yl-phenylamino)-8H-pyrido[2,3-d]pyrimidin-7-one;

2-(4-Pyrazol-1-yl-phenylamino)-8-(tetrahydro-pyran4-yl)-8H-pyrido[2,3-d]pyrimidin-7-one;

8-Cyclohex-2-enyl-2-(4-pyrazol-1-yl-phenylamino)-8H-pyrido[2,3-d]pyrimidin-7-one;

2-(4-Pyrazol-1-yl-phenylamino)-8-(1,3,3-trimethyl-bicyclo[2.2.1]hept-2-yl)-8H-pyrido[2,3]pyrimidin-7-one;

8-Bicyclo[2.2.1]hept-5-en-2-yl-2-(4-pyrazol-1-yl-phenylamino)-8H-pyrido[2,3-d]pyrimidin-7-one;

8-(1-Naphthalen-2-yl-ethyl)-2-(4-pyrazol-1-yl-phenylamino)-8H-pyrido[2,3-d]pyrimidin-7-one;

8-(1-Methyl-2-phenyl-ethyl)-2-(4-pyrazol-1-yl-phenylamino)-8H-pyrido[2,3-d]pyrimidin-7-one;
8-(2,5-Dimethyl-cyclohexyl)-2-(4-pyrazol-1-yl-phenylamino)-8H-pyrido[2,3-d]pyrimidin-7-one;
8-(4-sec-Butyl-cyclohexyl)-2-(4-pyrazo-1-yl-phenylamino)-8H-pyrido[2,3-d]pyrimidin-7-one;
8-Cyclohex-3-enyl-2-(4-pyrazol-1-yl-phenylamino)-8H-pyrido[2,3-d]pyrimidin-7-one;
8-Indan-1-yl-2-(4-pyrazol-1-yl-phenylamino)-8H-pyrido[2,3-d]pyrimidin-7-one;
8-(2-Isopropyl-5-methyl-cyclohexyl)-2-(4-pyrazol-1-yl-phenylamino)-8H-pyrido[2,3-d]pyrimidin-7-one;
8-(1-Naphthalen-2-yl-ethyl)-2-(4-pyrazol-1-yl-phenylamino)-8H-pyrido[2,3-d]pyrimidin-7-one;
8-(2,6-Dimethyl-cyclohexyl)-2-(4-pyrazol-1-yl-phenylamino)-8H-pyrido[2,3-d]pyrimidin-7-one;
8-(5-Isopropyl-2-methyl-cyclohexyl)-2-(4-pyrazol-1-yl-phenylamino)-8H-pyrido[2,3-d]pyrimidin-7-one;
8-(1-Methyl-pent-2-ynyl)-2-(4-pyrazol-1-yl-phenylamino)-8H-pyrido[2,3-d]pyrimidin-7-one;
8-Bicyclo[2.2.1]hept-2-yl-2-(4-pyrazol-1-yl-phenylamino)-8H-pyrido[2,3-d]pyrimidin-7-one;
8-(1-Methyl-2,2-diphenyl-ethyl)-2-(4-pyrazol-1-yl-phenylamino)-8H-pyrido[2,3-d]pyrimidin-7-one;
8-[1-(4-Methoxy-phenyl)-ethyl]-2-(4-pyrazol-1-yl-phenylamino)-8H-pyrido[2,3-d]pyrimidin-7-one;
2-(4-Pyrazol-1-yl-phenylamino)-8-(1,2,3,4-tetrahydro-naphthalen-2-yl)-8H-pyrido[2,3-d]pyrimidin-7-one;
2-(4-Pyrazol-1-yl-phenylamino)-8-(1-p-tolyl-ethyl)-8H-pyrido[2,3-d]pyrimidin-7-one;
8-Adamantan-2-yl-2-(4-pyrazol-1-yl-phenylamino)-8H-pyrido[2,3-d]pyrimidin-7-one;
8-(1-Methyl-but-3-ynyl)-2-(4-pyrazol-1-yl-phenylamino)-8H-pyrido[2,3-d]pyrimidin-7-one;
8-Bicyclo[2.2.1]hept-2-yl-2-(4-pyrazol-1-yl-phenylamino)-8H-pyrido[2,3-d]pyrimidin-7-one;
8-(1-Cyclohexyl-ethyl)-2-(4-pyrazol-1-yl-phenylamino)-8H-pyrido[2,3-d]pyrimidin-7-one;
8-Dicyclohexylmethyl-2-(4-pyrazol-1-yl-phenylamino)-8H-pyrido[2,3-d]pyrimidin-7-one;
8-(Phenyl-o-tolyl-methyl)-2-(4-pyrazol-1-yl-phenylamino)-8H-pyrido[2,3-d]pyrimidin-7-one;
8-[1-(3,4-Dichloro-phenyl)-ethyl]-2-(4-pyrazol-1-yl-phenylamino)-8H-pyrido[2,3-d]pyrimidin-7-one;
8-(1-Methyl-hexyl)-2-(4-pyrazol-1-yl-phenylamino)-8H-pyrido[2,3-d]pyrimidin-7-one;
8-Indan-2-yl-2-(4-pyrazol-1-yl-phenylamino)-8H-pyrido[2,3-d]pyrimidin-7-one;
8-[1-(2-Bromo-phenyl)-ethyl]-2-(4-pyrazol-1-yl-phenylamino)-8H-pyrido[2,3-d]pyrimidin-7-one;
8-(2-Methoxy-1-methyl-ethyl)-2-(4-pyrazol-1-yl-phenylamino)-8H-pyrido[2,3-d]pyrimidin-7-one;
8-(1-Methyl-2-phenyl-ethyl)-2-(4-pyrazol-1-yl-phenylamino)-8H-pyrido[2,3-d]pyrimidin-7-one;
8-(1-Ethyl-propyl)-2-(4-pyrazol-1-yl-phenylamino)-8H-pyrido[2,3-d]pyrimidin-7-one;
8-(4-Isopropyl-cyclohexyl)-2-(4-pyrazol-1-yl-phenylamino)-8H-pyrido[2,3-d]pyrimidin-7-one;
8-Acenaphthen-1-yl-2-(4pyrazol-1-yl-phenylamino)-8H-pyrido[2,3-d]pyrimidin-7-one;
8-(2-Oxo-cyclohexyl)-2-(4-pyrazol-1-yl-phenylamino)-8H-pyrido[2,3-d]pyrimidin-7-one;
2-(4-Pyrazol-1-yl-phenylamino)-8-(1,2,3,4-tetrahydro-naphthalen-1-yl)-8H-pyrido[2,3-d]pyrimidin-7-one;
8-(1-Methyl-heptyl)-2-(4-pyrazol-1-yl-phenylamino)-8H-pyrido[2,3-d]pyrimidin-7-one;
8-[Phenyl-(2-trifluoromethyl-phenyl)-methyl]-2-(4-pyrazol-1-yl-phenylamino)-8H-pyrido[2,3-d]pyrimidin-7-one;
2-(4-Pyrazol-1-yl-phenylamino)-8-(1,7,7-trimethyl-bicyclo[2.2.1]hept-2-yl)-8H-pyrido[2,3-d]pyrimidin-7-one;
8-(1,1-Dioxo-tetrahydro-8$^6$-thiophen-3-yl)-2-(4-pyrazol-1-yl-phenylamino)-8H-pyrido[2,3-d]pyrimidin-7-one;
8-(1-Biphenyl-4-yl-ethyl)-2-(4-pyrazol-1-yl-phenylamino)-8H-pyrido[2,3-d]pyrimidin-7-one;
8-(3-Methyl-cyclohexyl)-2-(4-pyrazol-1-yl-phenylamino)-8H-pyrido[2,3-d]pyrimidin-7-one;
8-Benzhydryl-2-(4-pyrazol-1-yl-phenylamino)-8H-pyrido[2,3-d]pyrimidin-7-one;
2-(4-Pyrazol-1-yl-phenylamino)-8-(9H-xanthen-9-yl)-8H-pyrido[2,3-d]pyrimidin-7-one;
8-(1-Pentyl-prop-2-ynyl)-2-(4-pyrazol-1-yl-phenylamino)-8H-pyrido[2,3-d]pyrimidin-7-one;
8-(Octahydro-inden-5-yl)-2-(4-pyrazol-1-yl-phenylamino)-8H-pyrido[2,3-d]pyrimidin-7-one;
8-(2-Phenyl-cyclohexyl)-2-(4-pyrazol-1-yl-phenylamino)-8H-pyrido[2,3-d]pyrimidin-7-one;
8-(3,5-Dimethyl-cyclohexyl)-2-(4-pyrazol-1-yl-phenylamino)-8H-pyrido[2,3-d]pyrimidin-7-one;
8-(4-tert-Butyl-cyclohexyl)-2-(4-pyrazol-1-yl-phenylamino)8H-pyrido[2,3-d]pyrimidin-7-one;
8-(2-Methyl-cyclohexyl)-2-(4-pyrazol-1-yl-phenylamino)-8H-pyrido[2,3-d]pyrimidin-7-one;
8-[3-Phenoxy-1-(2-phenoxy-ethyl)-propyl]-2-(4-pyrazol-1-yl-phenylamino)-8H-pyrido[2,3-d]pyrimidin-7-one;
8-(1-Cyclohexyl-propyl)-2-(4-pyrazol-1-yl-phenylamino)-8H-pyrido[2,3-d]pyrimidin-7-one;
8-(1-Ethyl-prop-2-ynyl)-2-(4pyrazol-1-yl-phenylamino)-8H-pyrido[2,3-d]pyrimidin-7-one;
8(1-Phenyl-heptyl)-2-(4-pyrazol-1-yl-phenylamino)-8H-pyrido[2,3-d]pyrimidin-7-one;
8-[(4-Methoxy-phenyl)-pyridin-2-yl-methyl]-2-(4-pyrazol-1-yl-phenylamino)-8H-pyrido[2,3-d]pyrimidin-7-one;
8-Bicyclohexyl-4-yl-2-(4-pyrazol-1-yl-phenylamino)-8H-pyrido[2,3-d]pyrimidin-7-one;
8-(4-Methyl-cyclohexyl)-2-(4-pyrazol-1-yl-phenylamino)-8H-pyrido[2,3-d]pyrimidin-7-one;
8-Cyclohexyl-2-(4-pyrazol-1-yl-phenylamino)-8H-pyrido[2,3-d]pyrimidin-7-one;
8-(Cyclohexyl-phenyl-methyl)-2-(4-pyrazol-1-yl-phenylamino)-8H-pyrido[2,3-d]pyrimidin-7-one;
8-(1-Phenyl-propyl)-2-(4-pyrazol-1-yl-phenylamino)-8H-pyrido[2,3-d]pyrimidin-7-one;
8-(1-Phenyl-prop-2-ynyl)-2-(4-pyrazol-1-yl-phenylamino)-8H-pyrido[2,3-d]pyrimidin-7-one;
8-(2-Phenyl-[1,3]dioxan-5-yl)-2-(4-pyrazol-1-yl-phenylamino)-8H-pyrido[2,3-d]pyrimidin-7-one;
2-(4-Pyrazol-1-yl-phenylamino)-8-(2,2,2-trifluoro-1-trifluoromethyl-ethyl)-8H-pyrido[2,3-d]pyrimidin-7-one;
2-[7-Oxo-2-(4-pyrazol-1-yl-phenylamino)-7H-pyrido[2,3-d]pyrimidin-8-yl]-propionitrile;
8-Cyclooctyl-2-(4-pyrazol-1-yl-phenylamino)-8H-pyrido[2,3-d]pyrimidin-7-one;
8-(Decahydro-naphthalen-2-yl)-2-(4-pyrazol-1-yl-phenylamino)-8H-pyrido[2,3-d]pyrimidin-7-one;
8(9H-Fluoren-9-yl)-2-(4-pyrazol-1-yl-phenylamino)-8H-pyrido[2,3-d]pyrimidin-7-one;
8-[4-(1,1-Dimethyl-propyl)-cyclohexyl]-2-(4-pyrazol-1-yl-phenylamino)-8H-pyrido[2,3-d]pyrimidin-7-one;
8-(10,11-Dihydro-5H-dibenzo[a,d]cyclohepten-5-yl)-2-(4-pyrazol-1-yl-phenylamino)-8H-pyrido[2,3-d]pyrimidin-7-one;
2-(4-Pyrazol-1-yl-phenylamino)-8-[2,2,2-trichloro-1-(4-fluoro-phenyl)-ethyl]-8H-pyrido[2,3-d]pyrimidin-7-one;
2-(4-Pyrazol-1-yl-phenylamino)-8-(3,3,5-trimethyl-cyclohexyl)-8H-pyrido[2,3-d]pyrimidin-7-one;

8-Cyclopentyl-2-[4-(3-diethylamino-2-hydroxy-propoxy)-phenylamino]-8H-pyrido[2,3-d]pyrimidin-7-one;

8-Cyclopentyl-2-[4-(2-hydroxy-3-morpholin-4-yl-propoxy)-phenylamino]-8H-pyrido[2,3-d]pyrimidin-7-one;

8-Cyclohexyl-2-[4-(3-diethylamino-2-hydroxy-propoxy)-phenylamino]-8H-pyrido[2,3-d]pyrimidin-7-one;

8-Cyclohexyl-2-[4-(2-hydroxy-3-morpholin-4-yl-propoxy)-phenylamino]-8H-pyrido[2,3-d]pyrimidin-7-one;

8-Bicyclo[2.2.1]hept-2-yl-2-[4-(3-diethylamino-2-hydroxy-propoxy)-phenylamino]-8H-pyrido[2,3-d]pyrimidin-7-one; and 8-Bicyclo[2.2.1]hept-2-yl-2-[4-(2-hydroxy-3-morpholin-4-yl-propoxy)-phenylamino]-8H-pyrido[2,3-d]pyrimidin-7-one.

Compounds of Formulas I and II may be prepared according to the syntheses outlined in Schemes 1 through 9, infra. Although these schemes often indicate exact structures, those with ordinary skill in the art will appreciate that the methods apply widely to analogous compounds of Formula I and/or II, given appropriate consideration to protection and deprotection or reactive functional groups by methods standard to the art of organic chemistry. For example, hydroxy groups, in order to prevent unwanted side reactions, generally need to be converted to ethers or esters during chemical reactions at other sites in the molecule. The hydroxy protecting group is readily removed to provide the free hydroxy group. Amino groups and carboxylic acid groups are similarly derivatized to protect them against unwanted side reactions. Typical protecting groups and methods for attaching and cleaving them are described fully by Greene and Wuts in *Protective Groups in Organic Synthesis*, John Wiley and Sons, New York, (2nd Ed., 1991), and McOmie, *Protective Groups in Organic Chemistry*, Plenum Press, New York, 1973.

Scheme 1 describes a typical method for the preparation of the pyrido[2,3-d]pyrimidin-7(8H)-ones of the invention. The synthesis begins with commercially available (Aldrich) 4-chloro-2-methylthio-pyrimidine-5-carboxylic acid ethyl ester. Displacement of the 4-chloro group with an amine in a solvent such as tetrahydrofuran in the presence or absence of a tertiary amine such as triethylamine provides the corresponding 4-amino-2-methylthio-pyrimidine-5-carboxylic acid ethyl ester. The amine used can be anhydrous or in an aqueous solution as with methyl or ethyl amine. The use of aqueous ammonium hydroxide provides the corresponding primary amine at position 4. Oxidation of the methylthio group with an oxidant such as an oxaziridine in a solvent such as chloroform at room temperature provides the methyl sulfoxide derivative. Displacement of the sulfoxide with an amine results in formation of the corresponding 2,4-diamino-pyrimidine-5-carboxylic acid ethyl ester. The temperature required for the displacement depends upon the amine used. Aromatic, secondary, and tertiary amines usually require higher temperatures than primary aliphatic or benzyl amines. When aromatic amines such as aniline are used, the reaction is usually run with the amine as the solvent at high temperatures. The ester group is sequentially reduced to the alcohol, preferably with lithium aluminum hydride in tetrahydrofuran, and then oxidized to the aldehyde. While sodium dichromate can be used as the oxidant, superior results are obtained with manganese II oxide in chloroform.

The 2,4-di-amino-pyrimidine-5-carboxaldehydes can be reacted with either a stabilized phosphorane, a phosphonate ester in the presence of a base, or any alternative Wittig or Horner-Emmons reagent to provide the corresponding unsaturated ester. The resulting double bond can be trans, cis, or a mixture of both. For example, reaction of a 2,4-diamino-pyrimidine-5-carboxaldehyde with an excess amount of the stabilized phosphorane (carbethoxymethylene)triphenylphosphorane in tetrahydrofuran at reflux temperature gives mainly, or in some cases exclusively, the trans unsaturated ethyl ester. Upon treatment with base, ring closure occurs to give the desired pyrido[2,3-d]pyrimidin-7 (8H)-one. This reaction can be carried out using a tertiary amine such as triethylamine or, preferably, N,N-diisopropylethyl amine as the solvent, with 1 to 10 equivalents of 1,8-diazabicyclo[5.4.0]undec-7-ene present. The reaction is carried out at elevated temperature, and is usually complete in 2 to 24 hours. Alternatively, the 2,4-diamino-pyrimidine-5-carboxaldehyde can be reacted with a phosphonate ester such as bis(2,2,2-trifluoroethyl) (methoxycarbonyl-methyl)-phosphonate using a strongly dissociated base (*Tetrahedron Lett.*, 1983:4405) to give predominately, if not exclusively, the cis unsaturated ester. Upon treatment with base under the conditions discussed previously, ring closure occurs.

SCHEME 1

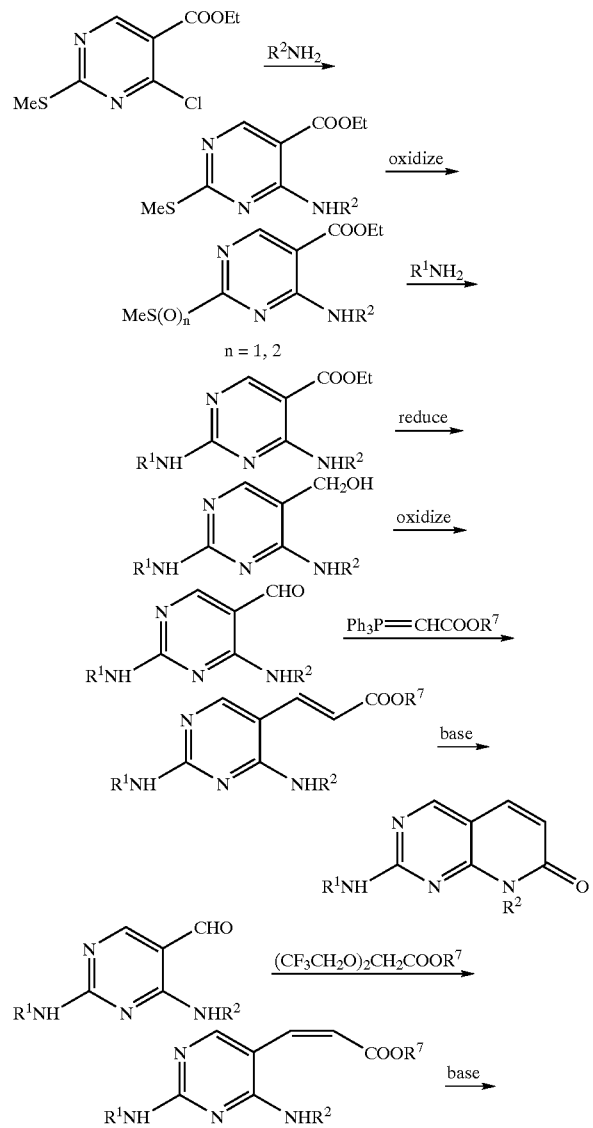

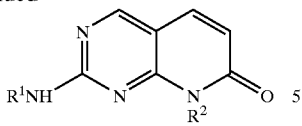

Scheme 2 depicts the preparation of pyrido[2,3-d]pyrimidin-7(8H)-ones of the invention where $R^2$ is H. The sequence of reactions is the same as Scheme 1, where the initial step uses ammonium hydroxide giving the 4-primary amino pyrimidine. The resultant pyrido[2,3-d]pyrimidin-7(8H)ones where $R^2$ is equal to H can be alkylated at the 8-position by treatment with a base such as sodium hydride in a solvent such as dimethylformamide or tetrahydrofuran at temperatures ranging from 40° C. to reflux, thus providing the corresponding pyrido[2,3-d]pyrimidin-7(8H)-ones where $R^2$ is other than H. The advantage of the route shown in Scheme 2 is that it allows for several $R^2$ analogs to be prepared from a common intermediate. The required aldehyde can also be obtained by reduction of the corresponding nitrile (*J. Org. Chem.*, 1960;82:5711) with a reducing agent, preferably diisobutylaluminum hydride.

SCHEME 2

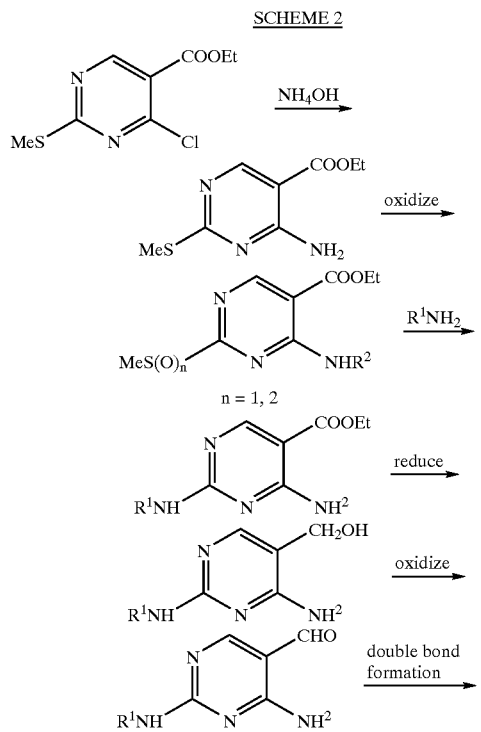

A route that allows for the preparation of several analogs with various $R^1$ groups from a common intermediate is shown in Scheme 3. The initial step is the same as in Scheme 1, but instead of oxidizing the methyl thio group, the ester is sequentially reduced and then oxidized using the conditions described in Scheme 1 to provide the corresponding 2-methylthio-4-amino-pyrimidine-5-carboxaldehyde. This aldehyde is converted to the corresponding unsaturated ester using the conditions described in Scheme 1. The methylthio group can be displaced directly with primary alkyl amines to give the pyrido[2,3d]pyrimidin-7-(8H)-ones of the invention where $R^1$ is H or a primary alkyl group. The methylthio group can also be converted to the corresponding sulfoxide by treatment with an oxidizing agent, preferably an oxaziridine, in a solvent such as chloroform at room temperature. Alternatively, an oxidizing agent, such as m-chloroperbenzoic acid, can be used in excess to convert the methylthio derivative to the corresponding methyl sulfone. Upon treatment of these oxidized derivatives with an amine, usually with several equivalents of the amine at elevated temperatures in the case of aromatic or tertiary amines, pyrido[2,3-d]pyrimidin-7(8H)-ones of the invention with various $R^1$ groups are obtained. In some cases a solvent such as tetrahydrofuran or dimethylsulfoxide can be used.

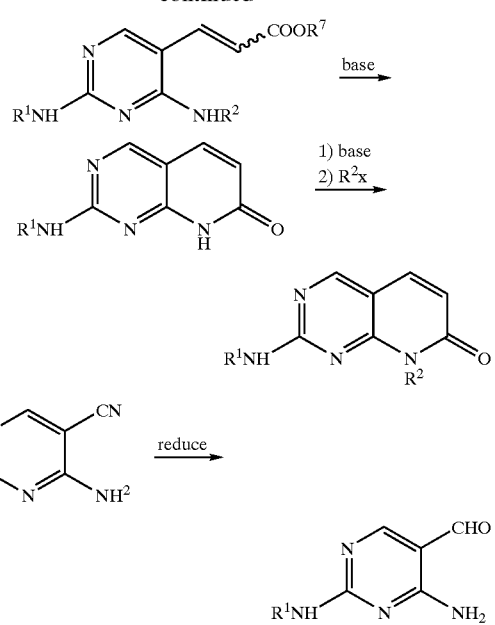

SCHEME 3

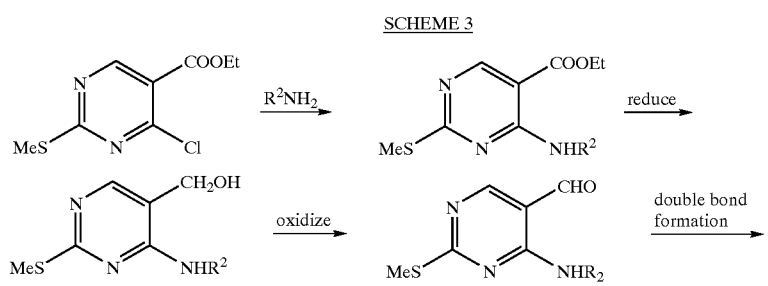

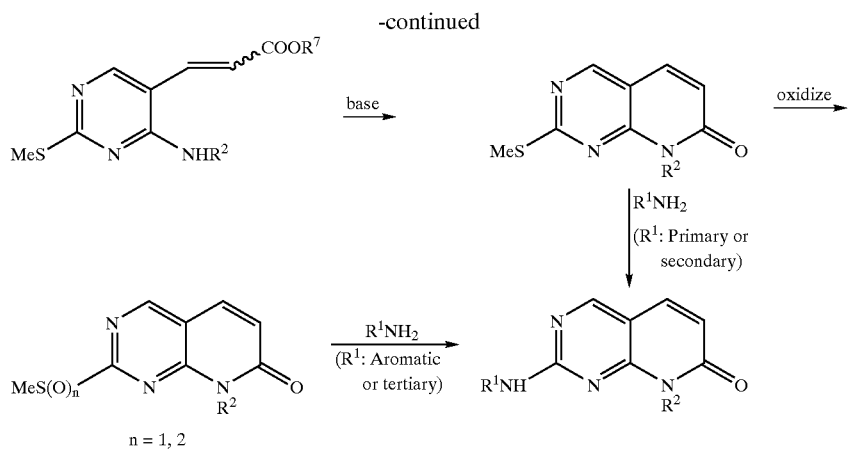

The most convergent route to the compounds of the invention where X is O is via the synthesis of 2-methanesulfanyl-8H-pyrido[2,3-d]pyrimidin-7-one which is depicted in Scheme 4. This key intermediate is prepared by the methods discussed in the previous schemes and is converted to the compounds of the invention by 2 routes, shown in Scheme 5. In the first, the methylthio group is converted to an amino group, in some cases via an oxidized intermediate. These derivatives are then alkylated at N8 to give the desired compounds. Alternatively, 2-methanesulfanyl-8H-pyrido[2,3-d]pyrimidin-7-one is first alkylated at N8, then the methylthio group, or an oxidized derivative, is displaced by an amine.

SCHEME 4

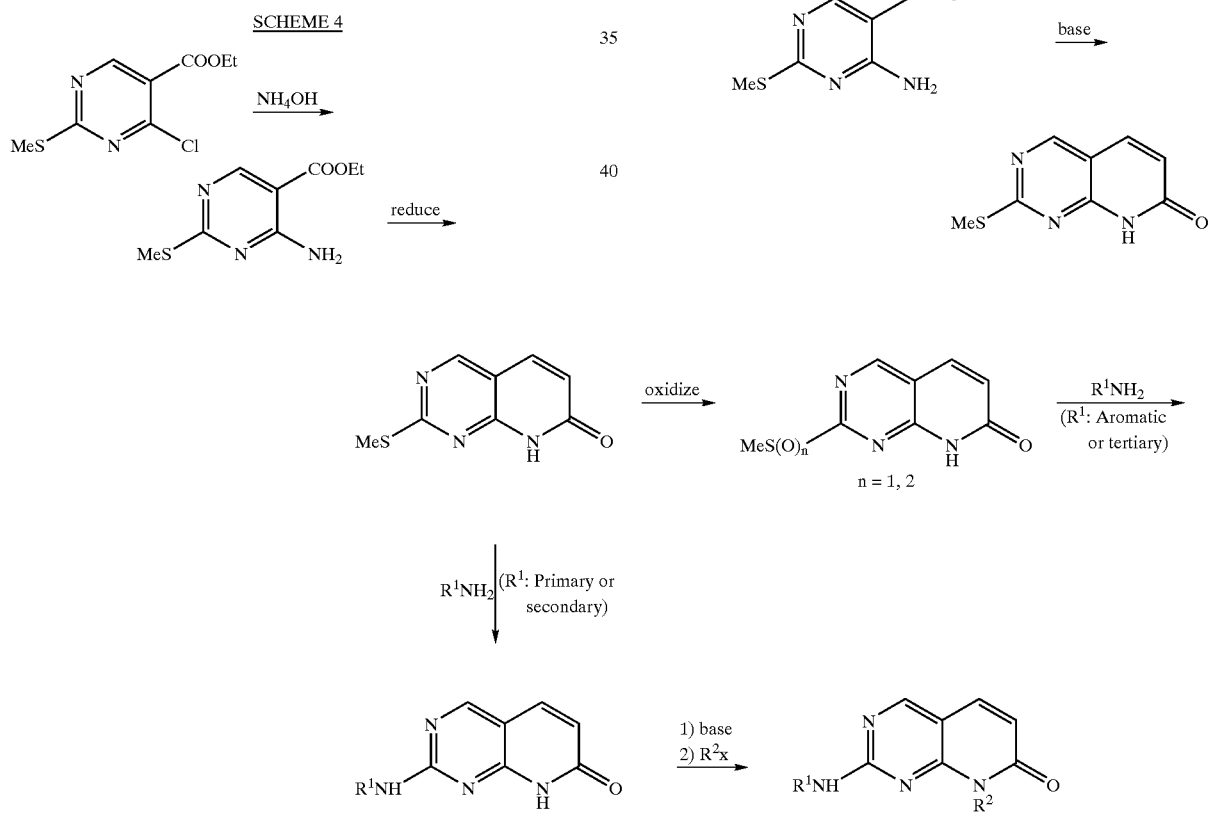

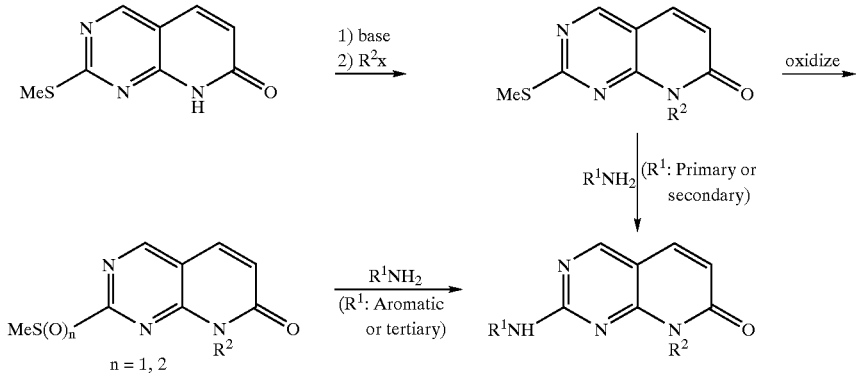

Scheme 6 describes a typical method for the preparation of the pyrido[2,3-d]pyrimidin-7(8H)-imines of the invention (X=NH). The synthesis begins with the 2,4-diaminopyrimidine-5-carboxaldehyde previously described in Scheme 1. Reaction with diethyl cyanomethylphosphonate in the presence of a base, such as sodium hydride, in a solvent such as tetrahydrofuran, provides the corresponding unsaturated nitrile. This nitrile is then cyclized to give the pyrido[2,3-d]pyrimidin-7(8H)-imine under the same conditions used to prepare the pyrido[2,3-d]pyrimidin-7(8H)-ones of Scheme 1. Alternatively, the pyrimidine-5-carboxaldehyde can contain a methylthio group at $C_2$. After formation of the unsaturated nitrile followed by ring closure, the methylthio group at $C_2$ can be converted to an amino group by the methology previously mentioned. The pyrido[2,3-d]pyrimidin-7(8H)-imines can also be converted to the pyrido[2,3-d]pyrimidin-7(8H)-ones by direct hydrolysis with concentrated acid, such as hydrochloric acid, at elevated temperatures. A milder method can also be used where the imine is first acylated with acetic anhydride. The hydrolysis of this acyl intermediate to the 7-one occurs under shorter reaction time and lower reaction temperatures.

SCHEME 6

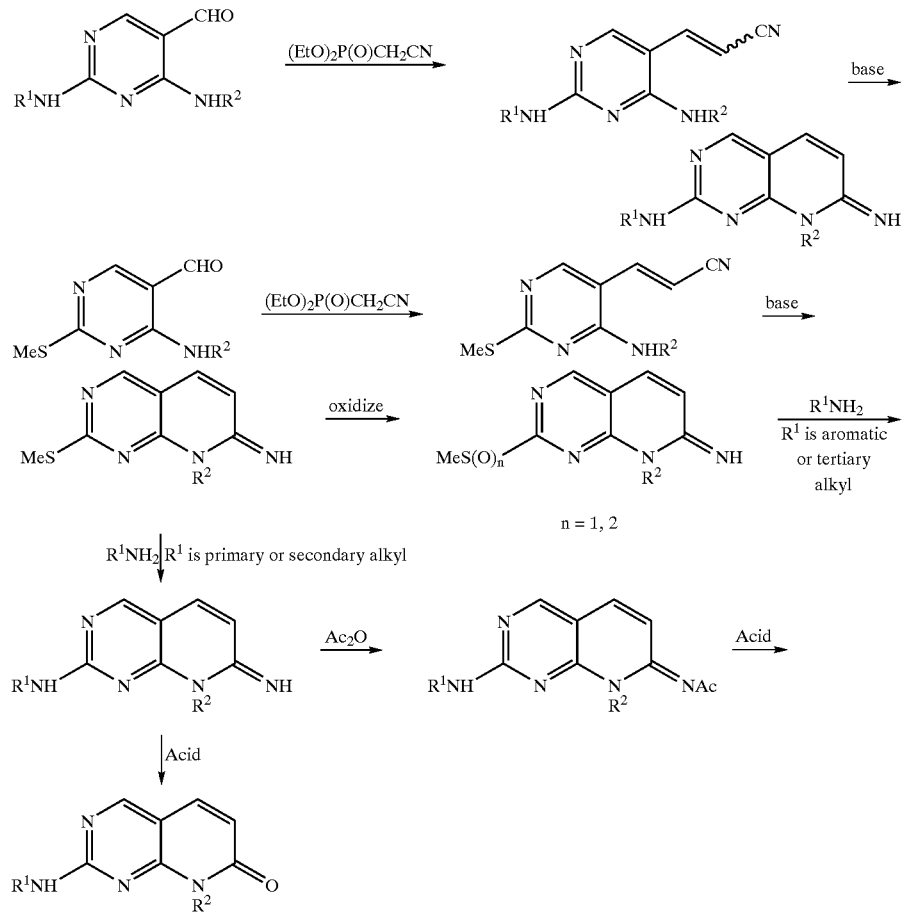

As shown in Scheme 7, those compounds where there is no double bond between $C_5$ and $C_6$ can be prepared by direct reduction of the double bond for those cases where X is O. Alternatively, a more preferred route is to reduce the double bond of the precursor unsaturated ester. This can be accomplished with a metal catalyst, such as palladium, in the presence of hydrogen under pressure. This saturated ester is then cyclized using the conditions discussed previously. Due to the propensity of the imine or nitrile group to be reduced under the conditions used to reduce the carbon-carbon double bond, a different route is required to prepare the compounds of the invention without a double bond at $C_5$—$C_6$ for those cases where X is NH. The saturated ester is hydrolyzed to the acid and then converted to the primary amide, by activation of the carboxylate with an acid chloride or N,N-carbonyldiimidazole, followed by treatment with ammonia gas or aqueous ammonium hydroxide. The primary amide is dehydrated to the corresponding nitrile with a reagent such as phosphorous pentoxide. This saturated nitrile is then cyclized using the conditions described previously.

SCHEME 7

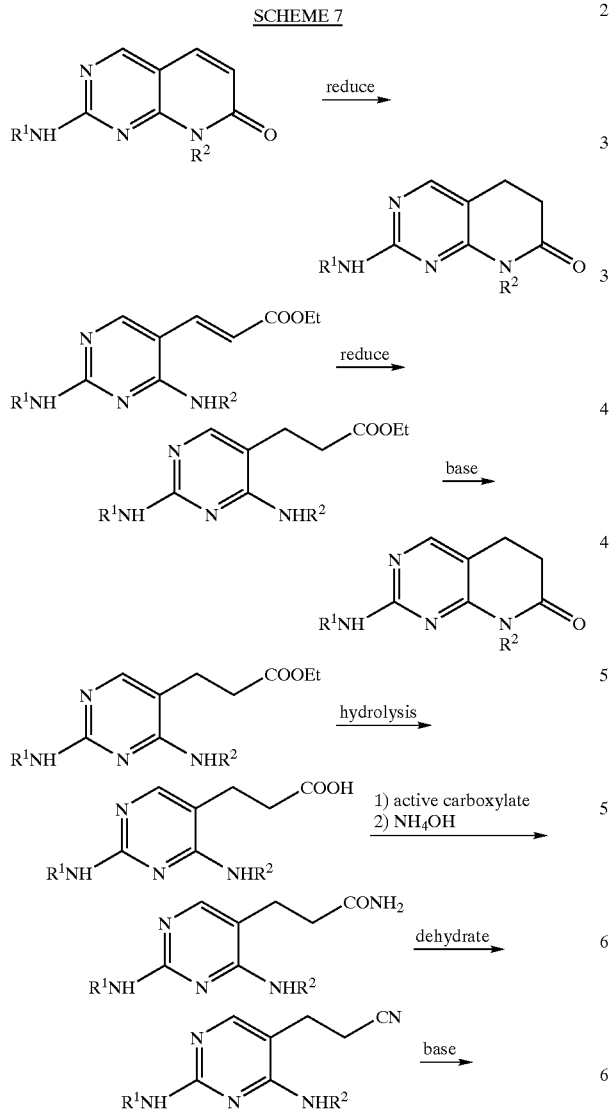

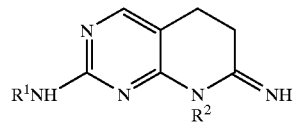

It should be noted that while the routes depicted in the earlier schemes showed the preparation of the pyrido[2,3-d]pyrimidin-7(8H)-ones of the invention where $R^3$ is H, these routes can be readily modified to prepare compounds where $R^3$ is lower alkyl, as shown in Scheme 8. Treatment with base provides compounds of the invention where X is O and $R^3$ is lower alkyl. Alternatively, these same reactions can be carried out on the 2-methylthio-4-amino-pyrimidine-5-carboxaldehyde and, after cyclization, the 2-methylthio group can be converted to the corresponding amine. Suitable modification of Scheme 6 would lead to the preparation of the pyrido[2,3-d]pyrimidin-7(8H)-imines of the invention where $R^3$ is lower alkyl.

SCHEME 8

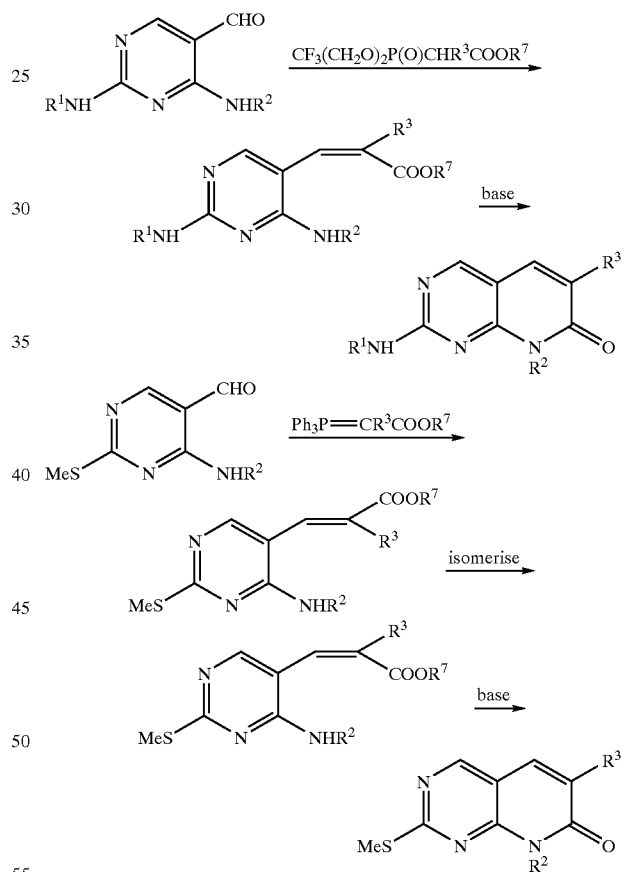

Additional 2,4-diaminopyrimidines of the invention can be prepared as shown in Scheme 9. For example, those analogs where Z is $CH_2OH$ are prepared by reduction of the ester with a reducing agent such as an excess of diisobutylaluminum hydride in a solvent such as tetrahydrofuran or chloroform. Subsequent oxidation with an oxidizing agent such as manganese oxide, or Swem's conditions, provides the compound where Z is CHO. Compounds where Z is $COOR^7$ or $CONHR^7$ can be obtained from the compound where Z is COOH. Activation of the carboxylate with an acid chloride or 1,1-carbonyldiimidazole, followed by addition of an alcohol of formula R⁷OH or an amine of formula R⁷NH₂, would provide those compounds where Z is COOR⁷ and CONHR⁷, respectively.

SCHEME 9

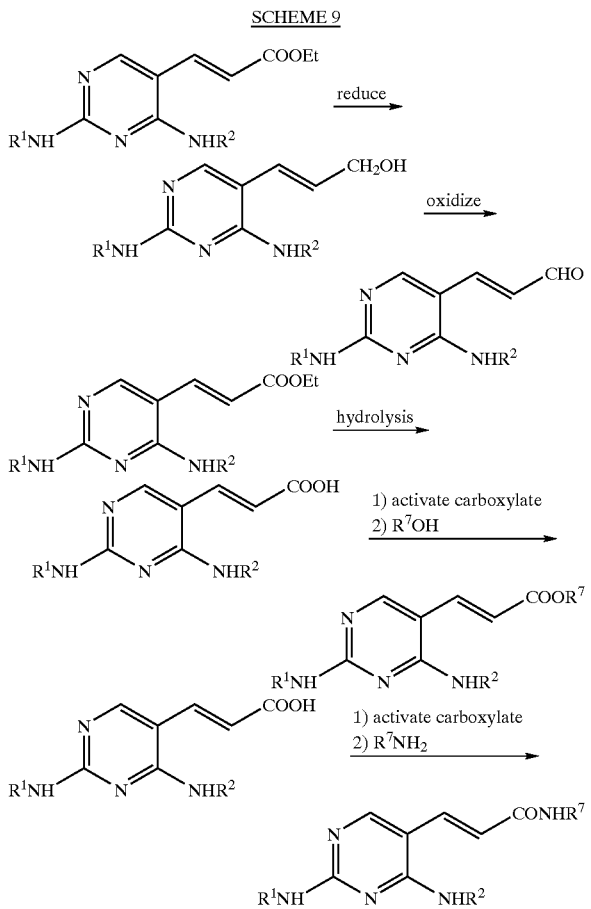

EXAMPLES

The following examples are for illustrative purposes only and are not intended, nor should they be construed as limiting the invention in any manner. Those skilled in the art will appreciate that variations and modifications can be made without violating the spirit or scope of the invention.

Example 1

4-Ethylamino-2-methanesulfanyl-pyrimidine-5-carboxylic acid ethyl ester

To a room temperature solution of 4-chloro-2-methanesulfanyl-pyrimidine-5-carboxylic acid ethyl ester (10.00 g, 43.10 mmol) in 150 mL of tetrahydrofuran was added triethylamine (18.5 mL, 133 mmol) followed by 9 mL of a 70% aqueous solution of ethylamine. The solution was stirred for 30 minutes then concentrated in vacuo and partitioned between chloroform and saturated aqueous sodium bicarbonate. The organic layer was dried over magnesium sulfate, filtered, and concentrated to provide 9.32 g (90%) of 4-ethylamino-2-methanesulfanyl-pyrimidine-5-carboxylic acid ethyl ester as an oil.

Analysis calculated for $C_{10}H_{15}N_3O_2S$: C, 49.77; H, 6.27; N, 17.41.

Found: C, 49.77; H, 6.24; N, 17.30.

Example 2

(4-Ethylamino-2-methanesulfanyl-pyrimidin-5-yl)-methanol

A solution of 4-ethylamino-2-methanesulfanyl-pyrimidine-5-carboxylic acid ethyl ester (8.93 g, 37.1 mmol) in 100 mL of tetrahydrofuran was added dropwise to a room temperature suspension of lithium aluminum hydride (2.30 g, 60.5 mmol) in 100 mL of tetrahydrofuran. After 10 minutes, the reaction was carefully quenched with 4.5 mL of water, 4.5 mL of 15% NaOH, and an additional 16 mL of water, and the mixture was stirred for 1.5 hours. The white precipitate was removed by filtration, washing with ethyl acetate. The filtrate was concentrated in vacuo and 1:1 hexane:ethyl acetate was added. The solids were collected to give 6.77 g (92%) of (4-ethylamino-2-methanesulfanyl-pyrimidin-5-yl)-methanol, mp 152–156° C.

Analysis calculated for $C_8H_{13}N_3OS$: C, 48.22; H, 6.58; N, 21.09.

Found: C, 48.14; H, 6.61; N, 20.85.

Example 3

4-Ethylamino-2-methanesulfanyl-pyrimidine-5-carboxaldehyde

To (4-ethylamino-2-methanesulfanyl-pyrimidin-5-yl)-methanol (6.44 g, 32.4 mmol) in 600 mL of chloroform was added manganese oxide (21.0 g, 241 mmol). The suspension was stirred at room temperature for 2 hours and an additional 5.5 g of manganese oxide was added. Stirring was continued for 4.5 hours. The mixture was filtered through celite, washing with chloroform. The filtrate was concentrated in vacuo to give 6.25 g (97%) of 4-ethylamino-2-methanesulfanyl-pyrimidine-5-carboxaldehyde, mp 58–61° C.

Analysis calculated for $C_8H_{11}N_3OS$: C, 48.71; H, 5.62; N, 21.30.

Found: C, 48.62; H, 5.60; N, 21.28.

Example 4

4-Ethylamino-2-methanesulfinyl-pyrimidine-5-carboxylic acid ethyl ester

To a room temperature solution of 4-ethylamino-2-methanesulfanyl-5-pyrimidinecarboxylate ethyl ester (2.011 g, 8.34 mmol) in 70 mL of chloroform was added (±)-trans-2-(phenylsulfonyl)-3-phenyloxaziridine (2.70 g, 10.34 mmol). The solution was stirred at room temperature for 7 hours then concentrated in vacuo. The residue was purified by flash chromatography, eluting with a gradient of ethyl acetate to 3% methanol in ethyl acetate, to provide 2.07 g (97%) of 4-ethylamino-2-methanesulfinyl-pyrimidine-5-carboxylic acid ethyl ester, mp 54–56° C.

Analysis calculated for $C_{10}H_{15}N_3O_3S$: C, 46.68; H, 5.88; N, 16.33.

Found: C, 46.56; H, 5.68; N, 16.23.

Example 5

4-Ethylamino-2-phenylamino-pyrimidine-5-carboxylic acid ethyl ester

A solution of 4-ethylamino-2-methanesulfinyl-pyrimidine-5-carboxylic acid ethyl ester (5.38 g, 20.9 mmol) in 4 mL of aniline was heated at 130° C. for 1 hour. The solution was cooled to room temperature, and 20 mL of 1:1 hexane:ethyl acetate was added. The resultant white solid was collected by filtration to give 1.96 g (33%) of the title product. The filtrate was concentrated in vacuo and purified by flash chromatography eluting with 3:1 hexane:ethyl acetate to provide an additional 257 mg (4%) of pure 4-ethylamino-2-phenylamino-pyrimidine-5-carboxylic acid ethyl ester, mp 145–147° C.

Analysis calculated for $C_{15}H_{18}N_4O_2$: C, 62.92; H, 6.34; N, 19.57.

Found: C, 62.83; H, 6.24; N, 19.50.

Example 6

(4-Ethylamino-2-phenylamino-pyrimidin-5-yl)-methanol

A solution of 4-ethylamino-2-phenylamino-pyrimidine-5-carboxylic acid ethyl ester (109 mg, 0.38 mmol) in 6 mL of tetrahydrofuran was added dropwise to a room temperature suspension of lithium aluminum hydride (35 mg, 0.92 mmol) in 5 mL of tetrahydrofuran. After 25 minutes, an additional 30 mg of lithium aluminum hydride was added, and stirring was continued for 30 minutes. The reaction was carefully quenched with 120 μL of water, 200 μL of 15% NaOH, and an additional 300 μL of water. After stirring for 1 hour, the white precipitate was removed by filtration, washing with ethyl acetate. The filtrate was concentrated in vacuo, and the crude material was purified by flash chromatography eluting with ethyl acetate to provide 36 mg (39%) of (4-ethylamino-2-phenylamino-pyrimidin-5-yl)-methanol, mp 174–176° C.

Analysis calculated for $C_{13}H_{16}N_4O$: C, 63.92; H, 6.60; N, 22.93.

Found: C, 63.97; H, 6.58; N, 22.79.

Example 7

4-Ethylamino-2-phenylamino-pyrimidine-5-carboxaldehyde

To a solution of (4-ethylamino-2-phenylamino-pyrimidin-5-yl)-methanol (173 mg, 0.71 mmol) in 15 mL of chloroform was added manganese oxide (600 mg, 6.89 mmol). After stirring at room temperature overnight, the mixture was filtered through a pad of celite, washing with chloroform. The filtrate was concentrated in vacuo to give 170 mg (99%) of 4-ethylamino-2-phenylamino-pyrimidine-5-carboxaldehyde, mp 155–157° C.

Analysis calculated for $C_{13}H_{14}N_4O$: C, 64.45; H, 5.82; N, 23.12.

Found: C, 64.31; H, 6.01; N, 22.98.

Example 8

4-Methylamino-2-methanesulfanyl-pyrimidine-5-carboxylic acid ethyl ester

To a room temperature solution of 4-chloro-2-methanesulfanyl-pyrimidine-5-carboxylic acid ethyl ester (18.66 g, 80.4 mmol) in 260 mL of tetrahydrofuran was added triethylamine (34 mL, 244 mmol) followed by 30 mL of a 40% aqueous solution of methylamine. The solution was stirred for 30 minutes, then was concentrated in vacuo and partitioned between chloroform and saturated aqueous sodium bicarbonate. The organic layer was washed with brine, dried over magnesium sulfate, filtered, and concentrated to provide a white solid. The solid was suspended in hexane and filtered to provide 14.70 g (81%) of 4-methylamino-2-methanesulfanyl-pyrimidine-5-carboxylic acid ethyl ester, mp 91–93° C. Literature mp 93–94° C.: *J Org. Chem.,* 1960:2137.

Analysis calculated for $C_9H_{13}N_3O_2S$: C, 47.56; H, 5.76; N, 18.49.

Found: C, 47.93; H, 5.67; N, 18.58.

Example 9

(4-Methylamino-2-methanesulfanyl-pyrimidin-5-yl)-methanol

A solution of 4-methylamino-2-methanesulfanyl-pyrimidine-5-carboxylic acid ethyl ester (4.36 g, 19.3 mmol) in 60 mL of tetrahydrofuran was added dropwise to a room temperature suspension of lithium aluminum hydride (1.10 g, 29.0 mmol) in 40 mL of tetrahydrofuran. After 10 minutes, the reaction was carefully quenched with 2 mL of water, 2 mL of 15% NaOH, and 7 mL of water, and the mixture was stirred for 1 hour. The white precipitate was removed by filtration, washing with ethyl acetate. The filtrate was concentrated in vacuo and 25 mL of 3:1 hexane:ethyl acetate was added. The solids were collected to give 2.99 g (84%) of (4-methylamino-2-methanesulfanyl-pyrimidin-5-yl) methanol, mp 155–157° C. Literature, mp 157–159° C.: *J Chem. Soc.,* 1968:733.

Analysis calculated for $C_7H_{11}N_3OS$: C, 45.39; H, 5.99; N, 22.68.

Found: C, 45.42; H, 5.93; N, 22.42.

Example 10

4-Methylamino-2-methanesulfanyl-pyrimidine5-carboxaldehyde

To (4-methylamino-2-methanesulfanyl-pyrimidin-5-yl)-methanol (5.78 g, 31.2 mmol) in 600 mL of chloroform was added manganese oxide (25.0 g, 286 mmol). The suspension was stirred at room temperature for 6 hours then filtered through celite washing with 300 mL of chloroform. The filtrate was concentrated in vacuo, and hexane was added to the residue. The solid was collected to give 5.35 g (93%) of 4-methylamino-2-methanesulfanyl-pyrimidine-5-carboxaldehyde, mp 97–100° C.

Example 11

4-Amino-2-methanesulfanyl-pyrimidine-5-carboxylic acid ethyl ester

To a room temperature solution of 4chloro-2-methanesulfanyl-pyrimidine-5-carboxylic acid ethyl ester (15.0 g, 65 mmol) in 200 mL of tetrahydrofuran was added 25 mL of triethylamine followed by 35 mL of aqueous ammonium hydroxide. After stirring at room temperature for 1.5 hours, an additional 30 mL of aqueous ammonium hydroxide was added, and stirred was continued for 1 hour. The reaction mixture was concentrated in vacuo and partitioned between ethyl acetate and saturated aqueous sodium bicarbonate. The organic layer was washed with brine, dried over magnesium sulfate, filtered, and concentrated in vacuo. Ethyl acetate and hexane were added, and the resultant solid was collected by filtration to provide 10.84 g (79%) of 4-amino-2-methanesulfanyl-pyrimidine-5-carboxylic acid ethyl ester.

Example 12

(4-Amino-2-methanesulfanyl-pyrimidin-5-yl)-methanol

A solution of 4-amino-2-methanesulfanyl-pyrimidine-5-carboxylic acid ethyl ester (13.36 g, 63 mmol) in 250 mL of tetrahydrofuran was added dropwise to a room temperature suspension of lithium aluminum hydride (3.82 g, 100 mmol) in 250 mL of tetrahydrofuran. After 30 minutes, the reaction was cooled to 0° C., and isopropyl alcohol was added until bubbling diminished. The reaction was quenched with 15 mL of water, 15 mL of 15% NaOH, and 50 mL of water, and the mixture was stirred for 1 hour. The white precipitate was removed by filtration, washing with ethyl acetate. The filtrate was concentrated in vacuo and 3:1 hexane:ethyl acetate was added. The solids were collected, washed with 3:1 hexane:ethyl acetate, followed by hexane. The solid was dissolved in ethyl acetate, and the solution was dried over magnesium sulfate. Filtration followed by concentration in vacuo gave 8.14 g (76%) of (4-amino-2-methanesulfanyl-pyrimidin-5-yl)-methanol.

Analysis calculated for $C_6H_9N_3OS$: C, 42.09; H, 5.30; N, 24.54.

Found: C, 42.31; H, 5.24; N, 24.27.

Example 13

4-Amino-2-methanesulfanyl-pyrimidine-5-carboxaldehyde

To (4-amino-2-methanesulfanyl-pyrimidin-5-yl)-methanol (8.14 g, 48 mmol) in 1 L of chloroform was added manganese oxide (33.13 g, 381 mmol). The suspension was stirred at room temperature overnight then filtered through celite washing with 300 mL of chloroform. The filtrate was concentrated in vacuo to give 8.14 g (quantitative yield) of 4-amino-2-methanesulfanyl-pyrimidine-5-carboxaldehyde, mp 185–187° C. Literature mp=183–184° C., *JOC*, 1958;23:1738.

Analysis calculated for $C_6H_7N_3OS$: C, 42.59; H, 4.17; N, 24.83.

Found: C, 42.84; H, 4.21; N, 24.73.

Example 14

4-(4-Methoxybenzylamino)-2-methanesulfanyl-pyrimidine-5-carboxylic acid ethyl ester To a room temperature solution of 4-chloro-2-methanesulfanyl-pyrimidine-5-carboxylic acid ethyl ester (6.05 g, 26.07 mmol) in 60 mL of tetrahydrofuran was added triethylamine (11 mL, 79.5 mmol) followed by 3.6 mL (27.6 mmol) of 4-methoxybenzylamine. The solution was stirred for 1 hour then filtered. The white solid was washed with ethyl acetate, and the filtrate was concentrated in vacuo. The residue was partitioned between chloroform and saturated aqueous sodium bicarbonate. The organic layer was dried over magnesium sulfate, filtered, and concentrated to provide 7.60 g (88%) of 4-(4-methoxybenzylamino)-2-methanesulfanyl-pyrimidine-5-carboxylic acid ethyl ester, mp 72–74° C.

Analysis calculated for $C_{16}H_{19}N_3O_3S$: C, 57.64; H, 5.74; N, 12.60.

Found: C, 57.65; H, 5.80; N, 12.57.

Example 15

[4-(4-Methoxybenzylamino)-2-methanesulfanyl-pyrimidin-5-yl]-methanol

A solution of 4-(4-methoxybenzylamino)-2-methanesulfanyl-pyrimidine-5-carboxylic acid ethyl ester (6.89 g, 20.70 mmol) in 60 mL of tetrahydrofuran was added dropwise to a room temperature suspension of lithium aluminum hydride (1.17 g, 30.8 mmol) in 40 mL of tetrahydrofuran. After 30 minutes, the reaction was carefully quenched with 2 mL of water, 2 mL of 15% NaOH, and 7 mL of water, and the mixture was stirred to give a white precipitate. The solid was removed by filtration, washing with ethyl acetate. The filtrate was partially concentrated in vacuo, and the white solid was collected by filtration to give 1.47 g (24%) of product. The filtrate was concentrated, and upon addition of 3:1 hexane:ethyl acetate, additional solid formed. The precipitate was collected to give 3.16 g (52%) of [4-(4-methoxybenzylamino)-2-methanesulfanyl-pyrimidin-5-yl]-methanol, mp 163–165° C.

Analysis calculated for $C_{14}H_{17}N_3O_2S$: C, 57.71; H, 5.88; N, 14.42.

Found: C, 57.78; H, 5.88; N, 14.36.

Example 16

4-(4-Methoxybenzylamino)-2-methanesulfanyl-pyrimidine-5-carboxaldehyde

To [4-(4-methoxybenzylamino)-2-methanesulfanyl-pyrimidin-5-yl]-methanol (4.08 g, 14.02 mmol) in 400 mL of chloroform was added manganese oxide (10.90 g, 125 mmol). The suspension was stirred at room temperature for 8 hours and then filtered through celite washing with chloroform. The filtrate was concentrated in vacuo followed by the addition of hexane to give 3.87 g (96%) of 4-(4-methoxybenzylamino)-2-methanesulfanyl-pyrimidine-5-carboxaldehyde, mp 87–89° C.

Analysis calculated for $C_{14}H_{15}N_3O_2S$: C, 58.11; H, 5.23; N, 14.52.

Found: C, 57.88; H, 5.12; N, 14.35.

Example 17

Ethyl 3-(4-Ethylamino-2-phenylamino-pyrimidin-5-yl) acrylate

To a room temperature solution of 4-ethylamino-2-phenylamino-pyrimidine-5-carboxaldehyde (320 mg, 1.32 mmol) in 12 mL of tetrahydrofuran was added (carbethoxymethylene)triphenylphosphorane (720 mg, 2.07 mmol). The reaction mixture was heated at reflux for 7 hours then stirred at room temperature overnight. An additional amount of (carbethoxymethylene)triphenylphosphorane (300 mg, 0.86 mmol) was added, and the reaction mixture was heated at reflux for an additional 8 hours then stirred at room temperature for 3 days. The reaction mixture was concentrated in vacuo, and the residue was purified by flash chromatography, eluting with 1:2 ethyl acetate:hexane, to provide 357 mg (86%) of ethyl 3-(4-ethylamino-2-phenylamino-pyrimidin-5-yl)acrylate, mp 125–126° C.

Analysis calculated for $C_{17}H_{20}N_4O_2$: C, 65.37; H. 6.45; N, 17.94.

Found: C, 65.40; H, 6.57; N, 17.64.

Example 18

8-Ethyl-2-phenylamino-8H-pyrido[2,3-d]pyrimidin-7-one

To a room temperature solution of ethyl 3-(4-ethylamino-2-phenylamino pyrimidin-5-yl)acrylate (179 mg, 0.57mmol) in 10 mL of triethylamine was added 90 μL of 1,8-diazabicyclo[5.4.0]undec-7-ene. The reaction mixture was heated at reflux for 8.5 hours then stirred at room temperature overnight. An additional amount of 1,8-diazabicyclo[5.4.0]undec-7-ene (90 μL) was added, and the reaction mixture was heated at reflux for 9 hours then stirred at room temperature overnight. The reaction mixture was concentrated in vacuo and purified by flash chromatography, followed by recrystallization from ethyl acetate:hexane, to provide 8-ethyl-2-phenylamino-8H-pyrido[2,3-d]pyrimidin-7-one, mp 203–204° C.

Analysis calculated for $C_{15}H_{14}N_4O$-0.05 EtOAc: C, 67.45; H, 5.36; N, 20.70.

Found: C, 67.29; H, 5.40; N, 20.62.

Example 19

Ethyl 3-(4-Amino-2-methanesulfanyl-pyrimidin-5-yl)acrylate

To a room temperature solution of 4-amino-2-methanesulfanyl-pyrimidine-5-carbaldeyde (4.08 g, 24.14 mmol) in 100 mL of tetrahydrofuran was added (carbethoxymethylene)triphenylphosphorane (10.80 g, 31 mmol). The reaction mixture was heated at reflux for 3 hours then stirred at room temperature overnight. The reaction mixture was concentrated in vacuo, and the residue was purified by flash chromatography, eluting with 1:1 ethyl acetate:hexane, to provide 4.30 g (75%) of ethyl 3-(4-amino-2-methanesulfanyl-pyrimidin-5-yl)acrylate, mp softens at 108° C.

Analysis calculated for $C_{10}H_{13}N_3O_2S$: C, 50.19; H, 5.48; N, 17.56.

Found: C, 50.22; H, 5.45; N, 17.24.

Example 20

2-Methanesulfanyl-8H-pyrido[2,3-d]pyrimidin-7-one

To a room temperature solution of ethyl 3-(4-amino-2-methanesulfanyl pyrimidin-5-yl)acrylate (368 mg, 1.53 mmol) in 3 mL of N,N-diisopropylethylamine was added 380 µL of 1,8-diazabicyclo[5.4.0]undec-7-ene. The reaction mixture was heated at reflux for 3 hours then cooled to room temperature and concentrated. The residue was purified by flash chromatography eluting with ethyl acetate. The fractions containing the product were partially concentrated in vacuo, and the solids were removed by filtration to provide 134 mg (45%) of 2-methanesulfanyl-8H-pyrido[2,3-d]pyrimidin-7-one, mp 269–271° C.

Analysis calculated for $C_8H_7N_3OS$: C, 49.73; H, 3.65; N, 21.75.

Found: C, 49.67; H, 3.46; N, 21.49.

Example 21

8-Ethyl-2-methanesulfanyl-8H-pyrido[2,3-d]pyrimidin-7-one

To a suspension of NaH (80 mg of a 60% suspension of NaH in mineral oil) in 10 mL of dimethylformamide was added 2-methanesulfanyl-8H-pyrido[2,3-d]pyrimidin-7-one (262 mg, 1.35 mmol). The reaction mixture was heated to 50° C. resulting in a brown solution. The solution was cooled slightly and iodoethane (150 µL, 1.88 mmol) was added. The reaction was heated at 50° C. for 10 minutes, then cooled to room temperature and partitioned between cold water and ethyl acetate. The organic layer was dried over magnesium sulfate, filtered, and concentrated in vacuo. The residue was purified by flash chromatography, eluting with 1:1 ethyl acetate:hexane to all ethyl acetate, to provide 192 mg (64%) of 8-ethyl-2-methanesulfanyl-8H-pyrido[2,3-d]pyrimidin-7-one, mp 104–106° C.

Analysis calculated for $C_{10}H_{11}N_3OS$: C, 54.28; H, 5.01; N, 18.99.

Found: C, 54.28; H. 5.03; N, 19.06.

Alternate Preparation of Example 21

8-Ethyl-2-methanesulfanyl-8H-pyrido[2,3-d]pyrimidin-7-one

To a room temperature solution of ethyl 3-(4-ethylamino-2-methanesulfanyl-pyrimidin-5-yl)acrylate (6.62 g, 24.78 mmol) in 30 mL of N,N-diisopropylethylamine was added 4.25 mL of 1,8-diazabicyclo[5.4.0]undec-7ene. The reaction mixture was heated at reflux overnight then cooled to room temperature. The resultant solid was collected by filtration and washed with 1:1 hexane:ethyl acetate to give 1.83 g (33%) of 8-ethyl-2-methanesulfanyl-8H-pyrido[2,3-d]pyrimidin-7-one. The filtrate was concentrated in vacuo and upon the addition of hexane, a solid formed that was collected, washed with hexane, and purified by flash chromatography eluting with ethyl acetate to provide an additional 2.22 g (40%) of title product.

Example 22

8-Ethyl-2-methanesulfinyl-8H-pyrido[2,3-d]pyrimidin-7-one

To a room temperature solution of 8-ethyl-2-methanesulfanyl-8H-pyrido[2,3-d]pyrimidin-7-one (2.22 g, 10.04 mmol) in 100 mL of chloroform was added (±)-trans-2-(phenylsulfonyl)-3-phenyloxaziridine (3.17 g, 12.15 mmol). The solution was stirred at room temperature overnight then concentrated in vacuo. The residue was treated with ethyl acetate to give a solid that was collected by filtration and washed with ethyl acetate to provide 2.21 g (93%) of 8-ethyl-2-methanesulfinyl-8H-pyrido[2,3-d]pyrimidin-7-one, mp 202–203° C.

Analysis calculated for $C_{10}H_{11}N_3O_2S$: C, 50.62; H, 4.67; N, 17.71.

Found: C, 50.30; H, 4.54; N, 17.45.

Example 23

8-Ethyl-2-methanesulfonyl-8H-pyrido[2,3-d]pyrimidin-7-one

To a room temperature solution of 8-ethyl-2-methanesulfanyl-8H-pyrido[2,3-d]pyrimidin-7-one (328 mg, 1.48 mmol) in 15 mL of chloroform was added m-chloroperbenzoic acid (m-CPBA) (810 mg of 50%–60% m-CPBA, remainder water). The reaction was stirred at room temperature for 1.5 hours then partitioned between chloroform and saturated sodium bicarbonate. The organic layer was dried over magnesium sulfate, filtered, and concentrated in vacuo. The residue was purified by flash chromatography, eluting with a gradient of ethyl acetate to 10% methanol in ethyl acetate, to provide 147 mg (39%) of product that contained trace amounts of impurities, and 42 mg (11%) of analytically pure 8-ethyl-2-methanesulfonyl-8H-pyrido[2,3-d]pyrimidin-7-one, mp 184–186° C.

Analysis calculated for $C_{10}H_{11}N_3O_3S$-0.25$H_2O$: C, 46.59; H, 4.50; N, 16.30.

Found: C, 46.77; H, 4.44; N, 16.24.

Example 24

Ethyl 3-(4-Ethylamino-2-methanesulfanyl-pyrimidin-5-yl)acrylate

To a room temperature solution of 4-ethylamino-2-methanesulfanyl-pyrimidine-5-carboxaldehyde (6.34 g, 32.14 mmol) in 100 mL of tetrahydrofuran was added (carbethoxymethylene)triphenylphosphorane (14.32 g, 41.14 mmol). The reaction mixture was heated at reflux for 70 minutes then concentrated in vacuo and the residue partitioned between ethyl acetate and 1 N HCl. The organic layer was extracted with additional 1 N HCl, the acidic layers were combined and treated with saturated sodium bicarbonate until basic. The product was extracted into ethyl acetate, and the organic layer was dried over magnesium sulfate, filtered, and concentrated. Upon the addition of hexane, a solid formed. The solid was collected by filtration to give 6.79 g (79%) of ethyl 3-(4-ethylamino-2-methanesulfanyl-pyrimidin-5-yl)acrylate. An analytical sample was obtained by flash chromatography eluting with ethyl acetate, mp 79–80° C.

Analysis calculated for $C_{12}H_{17}N_3O_2S$: C, 53.91; H, 6.41; N, 15.72.

Found: C, 53.97; H, 6.52; N, 15.78.

Example 25

Ethyl 3-(4-Methylamino-2-methanesulfanyl-pyrimidin-5-yl)acrylate

To a room temperature solution of 4-methylamino-2-methanesulfanyl pyrimidine-5-carboxaldehyde (5.00 g, 27.30 mmol) in 90 mL of tetrahydrofuran was added (carbethoxymethylene)triphenylphosphorane (12.35 g, 35.49 mmol). The reaction mixture was heated at reflux for 2.5 hours then cooled to room temperature and concentrated in vacuo. The residue was partitioned between ethyl acetate and 1 N HCl. The organic layer was treated with saturated sodium bicarbonate until basic. The product was extracted into ethyl acetate and the organic layer dried over magnesium sulfate, filtered, and concentrated. Upon the addition of 4:1 hexane:ethyl acetate, a solid formed that was collected by filtration to give 5.76 g (83%) of ethyl 3-(4 methylamino-2-methanesulfanyl-pyrimidin-5-yl)acrylate, mp 142–144° C.

Analysis calculated for $C_{11}H_{15}N_3O_2S$: C, 52.16; H, 5.97; N, 16.59.

Found: C, 51.89; H, 5.87; N, 16.38.

Example 26

8-Methyl-2-methanesulfanyl-8H-pyrido[2,3-d]pyrimidin-7-one

To a room temperature solution of ethyl 3-(4-methylamino-2-methanesulfanyl-pyrimidin-5-yl)acrylate (1.14 g, 4.48 mmol) in 6 mL of N,N-diisopropylethylamine was added 700 μL of 1,8-diazabicyclo[5.4.0]undec-7-ene. The reaction mixture was heated at reflux overnight then cooled to room temperature. An additional amount of 1,8-diazabicyclo[5.4.0]undec-7-ene (700 μL) was added,and the mixture was heated at reflux for 5 hours. The mixture was cooled to room temperature, and the solid was removed by filtration and purified by flash chromatography eluting with ethyl acetate. The fractions were concentrated and upon the addition of 3:1 hexane:ethyl acetate, a solid formed and was collected providing 172 mg (18%) of pure 8-methyl-2-methanesulfanyl-8H-pyrido[2,3-d]pyrimidin-7-one. Concentration of the filtrate provided an additional 184 mg (20%) of product, mp 190–192° C.

Analysis calculated for $C_9H_9N_3OS$: C, 52.16; H, 4.38; N, 20.27.

Found: C, 52.03; H, 4.24; N, 20.15.

Example 27

8-Methyl-2-methanesulfonyl-8H-pyrido[2,3-d]pyrimidin-7-one

To a room temperature solution of 8-methyl-2-methanesulfanyl-8H-pyrido[2,3-d]pyrimidin-7-one (187 mg, 0.90 mmol) in 10 mL of chloroform was added m-CPBA (550 mg of 50%–60% m-CPBA, remainder water). The reaction was stirred at room temperature for 2 hours then partitioned between chloroform and saturated sodium bicarbonate. The organic layer was dried over magnesium sulfate, filtered, and concentrated in vacuo. Upon the addition of chloroform followed by hexane, a solid formed and was collected to give 144 mg (67%) of 8-methyl-2-methanesulfonyl-8H-pyrido[2,3-d]pyrimidin-7-one, mp 194–196° C.

Analysis calculated for $C_9H_9N_3O_3S$: C, 45.18; H, 3.79; N, 17.56.

Found: C, 44.98; H, 3.76; N, 17.38.

Example 28

Ethyl 3-(4-Amino-2-phenylamino-pyrimidin-5-yl)acrylate

To a 0° C. solution of 4-amino-2-phenylamino-pyrimidine-5-carbonitrile (7.00 g, 33.18 mmol) (literature prep: *J Org. Chem.*, 1960:5711) in 170 mL of tetrahydrofuran was added 45 mL of a 1 M solution of diisobutylaluminum hydride in methylene chloride. The ice bath was removed, and an additional 40 mL of a 1 M solution of diisobutylaluminum hydride in methylene chloride was added. The reaction mixture was cooled to 0° C., and 60 mL of methanol was added dropwise. This mixture was then added to a rapidly stirring mixture of 300 mL of ethyl acetate and 250 mL of 1 N HCl. The layers were separated, and the organic layer was extracted with additional 1 N HCl. The acid layers were combined, treated with 330 mL of 1 N NaOH, and extracted with ethyl acetate. The organic layer was dried over magnesium sulfate, filtered, and concentrated. Purification by flash chromatography eluting with ethyl acetate gave 4.99 g (68%) of 4-amino-2-phenylamino-pyrimidine-5-carboxaldehyde.

To a room temperature solution of 4-amino-2-phenylamino-pyrimidine-5-carboxaldehyde (2.89 g, 13.50 mmol) in 120 mL of tetrahydrofuran was added (carbethoxymethylene)triphenylphosphorane (11.00 g, 31.60 mmol). The reaction mixture was heated at reflux for 9 hours then stirred at room temperature overnight. The solution was concentrated in vacuo and treated with ethyl acetate and hexane to give a yellow solid. The solid was collected by filtration and purified by flash chromatography to give 1.55 g (40%) of ethyl 3-(4-amino-2-phenylamino-pyrimidin-5-yl)acrylate, mp 190–192° C.

Analysis calculated for $C_{15}H_{16}N_4O_2$: C, 63.37; H, 5.67; N, 19.71.

Found: C, 63.08; H, 5.72; N, 19.72.

Example 29

8-(4-Methoxybenzylamino)-2-methanesulfanyl-8H-pyrido[2,3-d]pyrimidin-7-one

To a room temperature solution of 4-(4-methoxybenzylamino)-2-methanesulfanyl-pyrimidine-5-carboxaldehyde (1.35 g, 4.65 mmol) in 25 mL of tetrahydrofuran was added (carbethoxymethylene)

triphenylphosphorane (2.10 g, 6.00 mmol). The reaction mixture was heated at reflux for 6 hours then stirred at room temperature for 3 days. The reaction mixture was concentrated in vacuo and the residue partitioned between ethyl acetate and 1 N HCl. The acidic layer was treated with saturated sodium bicarbonate until basic. The product was extracted into ethyl acetate, and the organic layer was dried over magnesium sulfate. Filtration, concentration, and purification by flash chromatography eluting with 1:2 ethyl acetate:hexane provided 1.22 g (73%) of ethyl 3-(4-(4-methoxybenzylamino)-2-methanesulfanyl-pyrimidin-5-yl) acrylate as a thick oil.

To a room temperature solution of ethyl 3-(4-(4-methoxybenzylamino)-2-methanesulfanyl-pyrimidin-5-yl) acrylate (950 mg, 2.65 mmol) in 10 mL of N,N-diisopropylethylamine was added 3.4 mL of 1,8-diazabicyclo[5.4.0]undec-7-ene. The reaction mixture was heated at reflux for 4.5 hours then stirred at room temperature overnight. The liquid was decanted from the gummy solid and ethyl acetate was added to the residue. The solid was collected by filtration and washed with methanol to provide 141 mg (17%) of product. The filtrate was concentrated, and methanol was added. The solid was removed by filtration to provide 240 mg of analytically pure 8-(4-methoxybenzylamino)-2-methanesulfanyl-8H-pyrido [2,3-d]pyrimidin-7-one (28%). The filtrate was concentrated and purified by flash chromatography eluting with ethyl acetate to provide an additional 162 mg (19%) of product, mp 160–162° C.

Analysis calculated for $C_{16}H_{15}N_3O_2S$: C, 61.32; H, 4.82; N, 13.41.

Found: C, 61.06; H, 4.78; N, 13.47.

Example 30

2-Methanesulfinyl-8H-pyrido[2,3-d]pyrimidin-7-one

To a room temperature solution of 2-methanesulfanyl-8H-pyrido[2,3-d]pyrimidin-7-one (120 mg, 0.62 mmol) in 20 mL of chloroform was added (±)-trans-2-(phenylsulfonyl)-3-phenyloxaziridine (200 mg, 0.77 mmol). The solution was stirred at room temperature overnight. The solid was collected by filtration and found to be 2-methylthio-8H-pyrido [2,3-d]pyrimidin-7-one. The filtrate was stirred at room temperature for 2 days then concentrated. Addition of ethyl acetate resulted in the formation of a solid that was collected by filtration to provide 64 mg (76% based on recovered starting material) of 2-methanesulfinyl-8H-pyrido[2,3-d] pyrimidin-7-one, mp 237–242° C.

Analysis calculated for $C_8H_7N_3O_2S\cdot0.2H_2O$: C, 45.15; H, 3.50; N, 19.74.

Found: C, 45.41; H, 3.23; N, 19.80.

Example 31

Mixture of 2-methanesulfinyl-8H-pyrido[2,3-d] pyrimidin-7-one and 2-methanesulfonyl 8H-pyrido [2,3-d]pyrimidin-7-one To a room temperature suspension of 2-methanesulfanyl-8H-pyrido[2,3-d]pyrimidin-7-one (860 mg, 4.45 mmol) in 150 mL of chloroform was added m-CPBA (2.85 g of 50%–60% m-CPBA, remainder water). The reaction mixture was stirred at room temperature for 2 hours. The solid was filtered and washed with chloroform to give 924 mg of a mixture of 2-methanesulfinyl-8H-pyrido[2,3-d]pyrimidin-7-one and 2-methanesulfonyl-8H-pyrido[2,3-d]pyrimidin-7-one.

Example 32

2-Phenylamino-8H-pyrido[2,3-d]pyrimidin-7-one

A suspension of 204 mg of the mixture of 2-methanesulfinyl-8H-pyrido[2,3-d]pyrimidin-7-one and 2-methanesulfonyl-8H-pyrido[2,3-d]pyrimidin-7-one in 1 mL of aniline was heated at reflux for 10 minutes resulting in a dark brown solution. Upon cooling to room temperature, a solid formed. Ethyl acetate was added, and the solid was collected by filtration, washed with ethyl acetate, then suspended in methanol and filtered, and washed with additional methanol to provide 175 mg of 2-phenylamino-8H-pyrido[2,3-d]pyrimidin-7-one, mp>350° C.

Analysis calculated for $C_{13}H_{10}N_4S\cdot0.15H_2O$: C, 64.80; H, 4.31; N, 23.25.

Found: C, 64.56; H, 4.15; N, 23.59.

Example 33

8-Isopropyl-2-methanesulfanyl-8H-pyrido[2,3-d] pyrimidin-7-one

To a suspension of NaH (48 mg of a 60% suspension of NaH in mineral oil) in 6 mL of dimethylformamide was added 2-methanesulfanyl-8H-pyrido[2,3-d]pyrimidin-7-one (158 mg, 0.82 mmol). The reaction mixture was heated to 50° C. resulting in a yellow solution. The solution was cooled slightly and 2-iodopropane (120 μL, 1.20 mmol) was added. The reaction was heated at 50° C. for 30 minutes then cooled to room temperature and partitioned between water and ethyl acetate. The organic layer was dried over magnesium sulfate, filtered, and concentrated in vacuo. The residue was purified by flash chromatography, eluting with a gradient of 1:3 ethyl acetate:hexane to all ethyl acetate, to provide 140 mg (69%) of 8-isopropyl-2-methanesulfanyl-8H-pyrido [2,3-d]pyrimidin-7-one, mp 101–102° C.

Analysis calculated for $C_{11}H_{13}N_3OS$: C, 56.15; H, 5.57; N, 17.86.

Found: C, 56.07; H, 5.59; N, 17.78.

Example 34

8-Isopropyl-2-methanesulfinyl-8H-pyrido[2,3-d] pyrimidin-7-one

To a room temperature solution of 8-isopropyl-2-methanesulfanyl-8H-pyrido[2,3-d]pyrimidin-7-one (1.19 g, 5.08 mmol) in 50 mL of chloroform was added (±)-trans-2-(phenylsulfonyl)-3-phenyloxaziridine (1.76 g, 6.75 mmol). The solution was stirred at room temperature overnight then concentrated in vacuo. The residue was treated with ethyl acetate and hexane to give a solid which was collected by filtration and purified by flash chromatography, eluting with a gradient of ethyl acetate to 10% methanol in ethyl acetate, to provide 1.00 g (78%) of 8-isopropyl-2-methanesulfinyl-8H-pyrido[2,3-d]pyrimidin-7-one, mp 132–133° C.

Analysis calculated for $C_{11}H_{13}N_3O_2S$: C, 52.57; H, 5.21; N, 16.72.

Found: C, 52.68; H, 5.24; N, 16.48.

Examples 35–43

General procedure for the preparation of 8-substituted-2-phenylamino-8H-pyrido[2,3-d] pyrimidin-7-ones from 2-phenylamino-8H-pyrido[2, 3-d]pyrimidin-7-one Used to prepare Examples 35–43

To a suspension of NaH (1.0–1.5 equivalents of a 60% suspension of NaH in mineral oil) in 5 mL of dimethylformamide was added 2-phenylamino-8H-pyrido[2,3-d] pyrimidin-7-one (1 equivalent). The reaction mixture was heated to 50° C. to 60° C. resulting in a yellow solution. The solution was cooled slightly and the desired alkyl halide (1.1–2.0 equivalents) was added. The reaction mixture was heated at 50° C., for a time ranging from 5 minutes to 1 hour, then cooled to room temperature and partitioned between water and ethyl acetate. In some cases, the organic layer was washed with additional water or brine. The organic layer was dried over magnesium sulfate, filtered, and concentrated in vacuo. The residue was purified by the procedure noted.

Example 35

8-Benzyl-2-phenylamino-8H-pyrido[2,3-d] pyrimidin-7-one

Purified by flash chromatography eluting with a gradient of 1:1 ethyl acetate:hexane to all ethyl acetate (35%), mp 215–216° C.

Analysis calculated for $C_{20}H_{16}N_4O$: C, 72.16; H, 5.00; N, 16.83.

Found: C, 72.45; H, 4.83; N, 16.88.

Example 36

7-Oxo-2-phenylamino-7H-pyrido[2,3-d]pyrimidin-8-yl)-acetic acid methyl ester

Purified by adding methanol and ethyl acetate to the residue and collecting the resultant solid (44%), mp 232–233° C.

Analysis calculated for $C_{16}H_{14}N_4O_3$: C, 61.93; H, 4.55; N, 18.05.

Found: C, 61.68; H, 4.53; N, 18.02.

Example 37

8-Methoxymethyl-2-phenylamino-8H-pyrido[2,3-d] pyrimidin-7-one

Purified by flash chromatography eluting with a gradient of 1:1 ethyl acetate:hexane to all ethyl acetate (61%), mp 173–174° C.

Analysis calculated for $C_{15}H_{14}N_4O_2$: C, 63.82; H, 5.00; N, 19.85.

Found: C, 63.60; H, 4.86; N, 19.59.

Example 38

8-(3-Benzyloxypropyl)-2-phenylamino-8H-pyrido[2,3-d]pyrimidin-7-one

Purified by flash chromatography eluting with a gradient of 1:1 ethyl acetate:hexane to all ethyl acetate (46%), mp 133–135° C.

Analysis calculated for $C_{23}H_{22}N_4O_2$: C, 71.48; H, 5.74; N, 14.50.

Found: C, 71.20; H, 5.67; N, 14.35.

Example 39

8-Oxiranylmethyl-2-phenylamino-8H-pyrido[2,3-d] pyrimidin-7-one

Purified by flash chromatography eluting with a gradient of 1:1 ethyl acetate:hexane to all ethyl acetate to 10% methanol in ethyl acetate (38%), mp 163–165° C.

Analysis calculated for $C_{16}H_{14}N_4O_2 \cdot 0.05$ $CH_3COOCH_2CH_3$: C, 65.13; H, 4.86; N, 18.76.

Found: C, 64.73; H, 4.76; N, 18.66.

Example 40

8-Butyl-2-phenylamino-8H-pyrido[2,3-d]pyrimidin-7-one

Purified by flash chromatography eluting with a gradient of 1:1 ethyl acetate:hexane to all ethyl acetate (42%), mp 183–184° C.

Analysis calculated for $C_{17}H_{18}N_4O \cdot 0.25$ $H_2O$: C, 68.32; H, 6.24; N, 18.75.

Found: C, 68.35; H, 5.97; N, 18.69.

Example 41

2-Phenylamino-8-propyl-8H-pyrido[2,3-d] pyrimidin-7-one

Purified by flash chromatography eluting with a gradient of 1:1 ethyl acetate:hexane to all ethyl acetate (65%), mp 163–164° C.

Analysis calculated for $C_{16}H_{16}N_4O$: C, 68.55; H, 5.75; N, 19.99.

Found: C, 68.56; H, 5.97; N, 19.73.

Example 42

8-Isobutyl-2-phenylamino-8H-pyrido[2,3-d] pyrimidin-7-one

Purified by flash chromatography eluting with 1:1 ethyl acetate:hexane (72%), mp 170–171° C.

Analysis calculated for $C_{17}H_{18}N_4O \cdot 0.05$ $CH_3COOCH_2CH_3$: C, 68.89; H, 6.31; N, 18.47.

Found: C, 68.60; H, 6.20; N, 18.15.

Example 43

8-Isopropyl-2-phenylamino-8H-pyrido[2,3-d] pyrimidin-7-one

Purified by flash chromatography eluting with a gradient of 1:1 ethyl acetate:hexane to all ethyl acetate (23%), mp 170–171° C.

Analysis calculated for $C_{16}H_{16}N_4O$: C, 68.55; H, 5.75; N, 19.99.

Found: C, 68.31; H, 5.73; N, 19.88.

Examples 44–45

General procedure for the preparation of 2-amino-8-ethyl-8H-pyrido[2,3-d]pyrimidin-7-ones from 8-ethyl-2-methanesulfonyl-8H-pyrido[2,3-d] pyrimidin-7-one Used to Prepare Examples 44–45

To 8-ethyl-2-methanesulfonyl-8H-pyrido[2,3-d] pyrimidin-7-one (1 equivalent) was added 1 to 10 equivalents of an amine. In those examples where the amine used was aniline or a substituted aniline, the reaction mixture was heated at 175° C. for 10 minutes to 1 hour. In the case of primary amines, the reaction was run at room temperature for 10 to 60 minutes. The reaction mixture was partitioned between saturated sodium bicarbonate and ethyl acetate. In some cases, the organic layer was washed with additional water or brine. The organic layer was dried over magnesium sulfate, filtered, and concentrated in vacuo. The residue was purified by the procedure noted.

Alternate Preparation of Example 18

8-Ethyl-2-phenylamino-8H-pyrido[2,3-d]pyrimidin-7-one

Purified by flash chromatography eluting with a gradient of 1:1 hexane:ethyl acetate to all ethyl acetate (40%), mp 194–195° C.

Analysis calculated for $C_{15}H_{14}N_4O$: C, 67.65; H, 5.30; N, 21.04.

Found: C, 67.34; H, 5.19; N, 20.88.

Example 44

2-Benzylamino-8-ethyl-8H-pyrido[2,3-d]pyrimidin-7-one

Purified by adding 3:1 hexane:ethyl acetate to the residue and collecting the resultant solid (41%), mp 96–97° C.

Analysis calculated for $C_{16}H_{16}N_4O$: C, 68.55; H, 5.75; N, 19.99.

Found: C, 68.00; H, 5.87; N, 19.20.

Example 45

8-Ethyl-2-ethylamino-8H-pyrido[2,3-d]pyrimidin-7-one

Analytical material was obtained directly (87%), mp 60–161° C.

Analysis calculated for $C_{11}H_{14}N_4O$: C, 60.53; H, 6.47; N, 25.67.

Found: C, 60.27; H, 6.35; N, 25.61.

Examples 46–54

General procedure for the preparation of 2-amino-8-ethyl-8H-pyrido[2,3-d]pyrimidin-7-ones from 8-ethyl-2-methanesulfinyl-8H-pyrido[2,3-d]pyrimidin-7-one
Used to Prepare Examples 46–54

To 8-ethyl-2-methanesulfinyl-8H-pyrido[2,3-d] pyrimidin-7-one (1 equivalent) was added 1 to 10 equivalents of an amine. In those cases where the amine was aniline, a substituted aniline, or a tertiary amine, the reaction mixture was heated at 175° C. for 10 minutes to 1 hour. In the case of primary or secondary alkyl amines, the reaction was run at room temperature for 10 to 60 minutes. The reaction mixture was worked up and purified by the procedure noted.

Example 46

2-tert-Butylamino-8-ethyl-8H-pyrido[2,3-d]pyrimidin-7-one

After cooling to room temperature, the reaction mixture was partitioned between chloroform and saturated sodium bicarbonate. The organic layer was dried over magnesium sulfate, filtered, and concentrated in vacuo. The residue was purified by flash chromatography eluting with ethyl acetate (32%), mp 103–104° C.

Analysis calculated for $C_{13}H_{18}N_4O\cdot 0.25\ H_2O$: C, 62.27; H, 7.39; N, 22.36.

Found: C, 62.64; H, 7.45; N, 22.35.

Example 47

8-Ethyl-2-isopropylamino-8H-pyrido[2,3-d]pyrimidin-7-one

The reaction mixture was partitioned between ethyl acetate and saturated sodium bicarbonate. The organic layer was dried over magnesium sulfate, filtered, and concentrated in vacuo (71%), mp 119–120° C.

Analysis calculated for $C_{12}H_{16}N_4O$: C, 62.05; H, 6.94; N, 24.12.

Found: C, 61.84; H, 7.04; N, 23.92.

Example 48

2-Cyclohexylamino-8-ethyl-8H-pyrido[2,3-d]pyrimidin-7-one

The reaction mixture was partitioned between ethyl acetate and saturated sodium bicarbonate. The organic layer was washed with brine, dried over magnesium sulfate, filtered, and concentrated in vacuo. The solid was washed with hexane and filtered (67%), mp 135–136° C.

Analysis calculated for $C_{15}H_{20}N_4O$: C, 66.15; H, 7.40; N, 20.57.

Found: C, 66.20; H, 7.54; N, 20.57.

Example 49

2-(Biphenyl-4-ylamino)-8-ethyl-8H-pyrido[2,3-d]pyrimidin-7-one

After cooling to room temperature, ethyl acetate and hexane were added, and the resultant solid was collected and purified by flash chromatography eluting with ethyl acetate. A second chromatography eluting with a gradient of 2:1 hexane:ethyl acetate to all ethyl acetate gave clean product (32%), mp 207–208° C.

Analysis calculated for $C_{21}H_{18}N_4O\cdot 0.5\ H_2O$: C, 71.79; H, 5.41; N, 15.95.

Found: C, 72.08; H, 5.35; N, 15.78.

Example 50

8-Ethyl-2-(pyridin-4-ylamino)-8H-pyrido[2,3-d]pyrimidin-7-one

After cooling to room temperature, the reaction mixture was partitioned between chloroform and saturated sodium bicarbonate. The aqueous phase was extracted with additional chloroform, and the organic layers were combined, washed with brine, dried over magnesium sulfate, filtered, and concentrated in vacuo. The residue was purified by flash chromatography eluting with 5% chloroform in ethyl acetate (33%), mp 259–260° C.

Analysis calculated for $C_{14}H_{13}N_5O\cdot 0.25\ H_2O$: C, 61.87; H, 4.97; N, 25.78.

Found: C, 61.94; H, 4.73; N, 25.47.

Example 51

8-Ethyl-2-(4-methoxyphenylamino)-8H-pyrido[2,3-d]pyrimidin-7-one

After cooling to room temperature, ethyl acetate and hexane were added, and the resultant solid was collected and purified by recrystallization from ethyl acetate (59%), mp 196–197° C.

Analysis calculated for $C_{16}H_{16}N_4O_2\cdot 0.5\ H_2O$: C, 59.44; H, 5.88; N, 17.34.

Found: C, 59.37; H, 5.23; N, 17.12.

Example 52

2-[4-(2-Diethylaminoethoxy)-phenylamino]-8-ethyl-8H-pyrido[2,3-d]pyrimidin-7-one After cooling to room temperature, the reaction mixture was partitioned between ethyl acetate and saturated sodium bicarbonate. The organic layer was washed with brine, dried over magnesium sulfate, filtered, and concentrated in vacuo. Hexane and ethyl acetate were added and the resultant solid removed by filtration. The solid was purified by flash chromatography eluting with a gradient of ethyl acetate to 5% methanol in ethyl acetate to 30% methanol in ethyl acetate (30%), mp 128–129° C.

Analysis calculated for $C_{21}H_{27}N_5O_2$-0.5 $H_2O$: C, 64.62; H, 7.18; N, 17.95.

Found: C, 65.00; H, 7.11; N, 17.95.

Example 53

8-Ethyl-2-[4-(4-methylpiperazin-1-yl)-phenylamino]-8H-pyrido[2,3-d]pyrimidin-7-one After cooling to room temperature, the reaction mixture was dissolved in chloroform and purified by flash chromatographed eluting with 30% methanol in ethyl acetate. The fractions containing product were concentrated and upon the addition of hexane and ethyl acetate, a solid was obtained and collected by filtration (26%), mp 185–186° C.

Analysis calculated for $C_{20}H_{24}N_6O$-1.0 $H_2O$: C, 62.83; H, 6.81; N, 21.99.

Found: C, 63.12; H, 6.61; N, 21.78.

Example 54

8-Ethyl-2-[3-(1,1,2,2-tetrafluoroethoxy)-phenylamino]-8H-pyrido[2,3-d]pyrimidin-7-one After cooling to room temperature, the reaction mixture was partitioned between ethyl acetate and saturated sodium bicarbonate. The organic layer was washed with brine, dried over magnesium sulfate, filtered, and concentrated in vacuo. The resultant solid was purified by flash chromatography eluting with ethyl acetate (20%), mp 175–176° C.

Analysis calculated for $C_{17}H_{14}N_4F_4O_2$: C, 53.41; H, 3.69; N, 14.65.

Found: C, 53.19; H, 3.81; N, 14.39.

Example 55

8-Ethyl-2-(4-hydroxyphenylamino)-8H-pyrido[2,3-d]pyrimidin-7-one

A mixture of 8-ethyl-2-(4-methoxyphenylamino)-8H-pyrido[2,3-d]pyrimidin-7-one (133 mg, 0.45 mmol) and 1 mL of 48% aqueous HBr in 10 mL of propionic acid was heated at reflux for 3 hours. After cooling to room temperature, the reaction mixture was partitioned between ethyl acetate and saturated sodium bicarbonate. The aqueous layer was further extracted with ethyl acetate and the organic layers were combined and washed with brine, dried over magnesium sulfate, filtered, and concentrated in vacuo. The resultant solid was purified by dissolving in ethyl acetate and passing the solution through silica gel to provide 58 mg (46%) of 8-ethyl-2-(4 hydroxyphenylamino)-8H-pyrido[2,3-d]pyrimidin-7-one, mp 222–224° C.

Analysis calculated for $C_{15}H_{14}N_4O_2$-0.25 $H_2O$: C, 62.83; H, 5.06; N, 19.55.

Found: C, 63.12; H, 4.93; N, 19.18.

Example 56

2-Benzyloxyphenylamino-8-ethyl-8H-pyrido[2,3-d]pyrimidin-7-one

A mixture of 8-ethyl-2-(4-hydroxyphenylamino)-8H-pyrido[2,3-d]pyrimidin-7-one (94 mg, 0.33 mmol), benzyl bromide (70 mg, 0.41 mmol) and potassium carbonate (370 mg, 2.67 mmol) in 5 mL of dimethylformamide was heated at reflux for 5 minutes. After cooling to room temperature, water was added, and the resultant solid was collected and purified by flash chromatography eluting with a gradient of 1:1 hexane:ethyl acetate to all ethyl acetate to provide 70 mg (56%) of 2-benzyloxyphenylamino-8-ethyl-8H-pyrido[2,3-d]pyrimidin-7-one, mp 195–197° C.

Analysis calculated for $C_{22}H_{20}N_4O_2$: C, 70.95; H, 5.41; N, 15.04.

Found: C, 70.56; H, 5.44; N, 14.86.

Example 57

8-Ethyl-2-[4-(2-methoxyethoxy)phenylamino]-8H-pyrido[2,3-d]pyrimidin-7-one

A mixture of 8-ethyl-2-(4-hydroxyphenylamino)-8H-pyrido[2,3-d]pyrimidin-7-one (92 mg, 0.33 mmol), 2-methoxyethyl bromide (55 mg, 0.40 mmol) and potassium carbonate (360 mg, 2.61 mmol) in 5 mL of dimethylformamide was heated at reflux for 5 minutes. After cooling to room temperature, water was added, and the resultant solid collected by filtration. The solid was dissolved in ethyl acetate and the solution dried over magnesium sulfate, filtered, concentrated, and purified by flash chromatography eluting with ethyl acetate to provide 92 mg (56%) of 8-ethyl-2-[4-(2-methoxyethoxy)phenylamino]-8H-pyrido[2,3-d]pyrimidin-7-one, mp 169–171° C.

Analysis calculated for $C_{18}H_{20}N_4O_3$-0.25 $H_2O$: C, 62.70; H, 5.95; N, 16.26.

Found: C, 62.86; H, 5.87; N, 16.36.

Example 58

8-(4Methoxybenzyl)-2-phenylamino-8H-pyrido[2,3-d]pyrimidin-7-one

To a room temperature solution of 8-(4-methoxybenzylamino)-2-methanesulfanyl-8H-pyrido[2,3-d]pyrimidin-7-one (380 mg, 1.21 mmol) in 20 mL of chloroform was added m-CPBA (900 mg of 50%–60% m-CPBA, remainder water). The reaction was stirred at room temperature for 2 hours then partitioned between chloroform and saturated sodium bicarbonate. The organic layer was washed with additional saturated sodium bicarbonate followed by brine, dried over magnesium sulfate, filtered, and concentrated in vacuo. Upon the addition of chloroform and hexane, a solid formed and was collected to give 335 mg (62%) of 8-(4-methoxybenzylamino)-2-methanesulfonyl-8H-pyrido[2,3-d]pyrimidin-7-one.

A solution of 8-(4-methoxybenzylamino)-2-methanesulfonyl-8H-pyrido[2,3-d]pyrimidin-7-one (217 mg, 0.63 mmol) in 1.5 mL of aniline was heated at reflux for 10 minutes. Upon cooling to room temperature, a solid formed. Water (10 mL) was added, and the filtrate was decanted from the gummy solid that was then dissolved in ethyl acetate and purified by flash chromatography eluting with a gradient of 2:1 hexane:ethyl acetate to all ethyl acetate. The fractions containing product were concentrated in vacuo and treated with hexane and ethyl acetate. The solid was collected by filtration to provide 101 mg (45%) of 8-(4-methoxybenzyl)-2-phenylamino-8H-pyrido[2,3-d]pyrimidin-7-one, mp 215–216° C.

Analysis calculated for $C_{21}H_{18}N_4O_2$: C, 70.38; H, 5.06; N, 15.63.

Found: C, 70.06; H, 4.91; N, 15.47.

Example 59

2-[4-(2-Diethylaminoethoxy)-phenylamino]-8-isopropyl-8H-pyrido[2,3-d]pyrimidin-7-one To 8-isopropyl-2-methanesulfinyl-8H-pyrido[2,3-d]pyrimidin-7-one (126 mg, 0.50 mmol) was added 4-(2-diethylaminoethoxy)aniline (313 mg, 1.51 mmol). The reaction mixture was heated at 175° C. for 10 minutes then cooled to room temperature and partitioned between saturated sodium bicarbonate and ethyl acetate. The organic layer was dried over magnesium sulfate, filtered, and concentrated in vacuo. The residue was purified by flash chromatography eluting with 10% methanol in ethyl acetate. The fractions containing product were concentrated, and hexane was added. The resultant solid was collected by filtration to give 94 mg (47%) of 2-[4-(2-diethylaminoethoxy)-phenylamino]-8-isopropyl-8H-pyrido[2,3-d]pyrimidin-7-one, mp 84–85° C.

Analysis calculated for $C_{22}H_{29}N_5O_2$: C, 66.81; H, 7.39; N, 17.71.

Found: C, 66.63; H, 7.47; N, 17.72.

Example 60

8-Isopropyl-2-[4-(4-methylpiperazin-1-yl)-phenylamino]-8H-pyrido[2,3-d]pyrimidin-7-one To 8-isopropyl-2-methanesulfinyl-8H-pyrido[2,3-d]pyrimidin-7-one (212 mg, 0.85 mmol) was added 4-(4-methylpiperazin-1-yl)-aniline (323 mg, 1.69 mmol). The reaction mixture was heated at 175° C. for 10 minutes then cooled to room temperature and partitioned between saturated sodium bicarbonate and chloroform. The organic layer was washed with brine, dried over magnesium sulfate, filtered, and concentrated in vacuo. The residue was purified by flash chromatography eluting with 10% methanol in ethyl acetate. The fractions containing product were concentrated, and hexane and ethyl acetate were added to give a solid that was dissolved in chloroform and passed through an aluminum oxide column. The fractions containing product were concentrated, and upon addition of hexane and ethyl acetate, a solid formed providing 160 mg (50%) of 8-isopropyl-2-[4-(4-methylpiperazin-1-yl)-phenylamino]-8H-pyrido[2,3-d]pyrimidin-7-one, mp 221–222° C.

Analysis calculated for $C_{21}H_{26}N_6O \cdot 0.25\ H_2O$: C, 65.88; H, 6.93; N, 21.96.

Found: C, 66.18; H, 6.95; N, 21.57.

Example 61

8-Methyl-2-phenylamino-8H-pyrido[2,3-d]pyrimidin-7-one

A mixture of 8-methyl-2-methanesulfonyl-8H-pyrido[2,3-d]pyrimidin-7-one (287 mg, 1.20 mmol) in 1 mL of aniline was heated at reflux for 10 minutes. The reaction mixture was partitioned between ethyl acetate and saturated sodium bicarbonate. The organic layer was washed with brine, dried over magnesium sulfate, and concentrated in vacuo. Upon addition of ethyl acetate and hexane, a precipitate formed and was collected to give 107 mg (35%) of product. An analytical sample of 8-methyl-2-phenylamino-8H-pyrido[2,3-d]pyrimidin-7-one was obtained by recrystallization from hexane and ethyl acetate followed by flash chromatography eluting with ethyl acetate, mp 244–247° C.

Analysis calculated for $C_{14}H_{12}N_4O \cdot 0.20\ H_2O$: C, 65.71; H, 4.88; N, 21.89.

Found: C, 65.73; H, 4.45; N, 21.55.

Example 62

2-Amino-8-methyl-8H-pyrido[2,3-d]pyrimidin-7-one

8-Methyl-2-methanesulfanyl-8H-pyrido[2,3-d]pyrimidin-7-one (160 mg, 0.77 mmol) was dissolved in 15 mL of methanolic ammonia and heated in a sealed glass tube at 120° C. for 35 hours. The resultant crystals were collected by filtration washing with 1:1 hexane:ethyl acetate to give 77 mg (57%) of 2-amino-8-methyl-8H-pyrido[2,3-d]pyrimidin-7-one, mp 237–253° C.

Analysis calculated for $C_8H_8N_4O \cdot 0.15\ H_2O$: C, 53.71; H, 4.68; N, 31.32.

Found: C, 53.86; H, 4.69; N, 31.00.

Example 63

2-Benzylamino-8-methyl-8H-pyrido[2,3-d]pyrimidin-7-one

A solution of 8-methyl-2-methanesulfanyl-8H-pyrido[2,3-d]pyrimidin-7-one (171 mg, 0.83 mmol) in 1.5 mL of benzylamine was heated at reflux for 3 hours. The solid that formed upon cooling was collected by filtration, washed with 1:1 hexane:ethyl acetate, and then chromatographed eluting with ethyl acetate to give 95 mg (43%) of 2-benzylamino-8-methyl-8H-pyrido[2,3-d]pyrimidin-7-one, mp 160–162° C.

Analysis calculated for $C_{15}H_{14}N_4O$: C, 67.65; H, 5.30; N, 21.04.

Found: C, 67.81; H, 5.07; N, 20.99.

Example 64

2-Butylamino-8-methyl-8H-pyrido[2,3-d]pyrimidin-7-one

A solution of 8-methyl-2-methanesulfonyl-8H-pyrido[2,3-d]pyrimidin-7-one (200 mg, 0.83 mmol) in 2 mL of n-butylamine was stirred at room temperature for 10 minutes. The reaction mixture was partitioned between ethyl acetate and water, and the organic layer was washed with saturated sodium bicarbonate and brine, dried over magnesium sulfate, and concentrated in vacuo. A 4:1 mixture of hexane:ethyl acetate was added to the residue and the resultant solid collected by filtration to give 154 mg (79%) of 2-butylamino-8-methyl-8H-pyrido[2,3-d]pyrimidin-7-one, mp 146–147° C.

Analysis calculated for $C_{12}H_{16}N_4O$: C, 62.05; H, 6.94; N, 24.12.

Found: C, 61.91; H, 6.86; N, 24.13.

Example 65

2-Ethylamino-8-methyl-8H-pyrido[2,3-d]pyrimidin-7-one

A mixture of 8-methyl-2-methanesulfonyl-8H-pyrido[2,3-d]pyrimidin-7-one (152 mg, 0.63 mmol) in 2.5 mL of 70% aqueous ethylamine was stirred at room temperature for 10 minutes. The reaction mixture was partitioned between ethyl acetate and water, and the organic layer was washed with saturated sodium bicarbonate and brine, dried over magnesium sulfate, and concentrated in vacuo to give 105 mg (82%) of 2-ethylamino 8-methyl-8H-pyrido[2,3-d]pyrimidin-7-one, mp 194–195° C.

Analysis calculated for $C_{10}H_{12}N_4O$: C, 58.81; H, 5.92; N, 27.43.

Found: C, 58.44; H, 5.80; N, 27.15.

Example 66

8-Methyl-2-(2-pyridin-2-yl-ethylamino)-8H-pyrido [2,3-d]pyrimidin-7-one

A mixture of 8-methyl-2-methanesulfonyl-8H-pyrido[2,3-d]pyrimidin-7-one (165 mg, 0.69 mmol) and 2-(2-aminoethyl)-pyridine (165 µL, 1.38 mmol) in 2 mL of tetrahydrofuran was stirred at room temperature for 30 minutes. The solid was collected to give 40 mg (21%) of product. The filtrate was concentrated and purified by flash chromatography to give 125 mg (64%) of 8-methyl-2-(2-pyridin-2-yl-ethylamino)-8H-pyrido[2,3-d]pyrimidin-7-one, mp 155–156° C.

Analysis calculated for $C_{15}H_{15}N_5O$-0.20 $H_2O$: C, 63.03; H, 5.46; N, 24.51.

Found: C, 63.31; H, 5.18; N, 24.75.

Example 67

2-Isopropylamino-8-methyl-8H-pyrido[2,3-d] pyrimidin-7-one

A mixture of 8-methyl-2-methanesulfonyl-8H-pyrido[2,3-d]pyrimidin-7-one (194 mg, 0.81 mmol) and 2 mL of isopropylamine was stirred at room temperature for 15 minutes. Excess amine was removed in vacuo, and the residue was partitioned between ethyl acetate and water. The organic phase was washed with saturated sodium bicarbonate, followed by brine, dried over magnesium sulfate, and concentrated to give 168 mg (95%) of 2-isopropylamino-8-methyl-8H-pyrido[2,3-d]pyrimidin-7-one, mp 148–149° C.

Analysis calculated for $C_{11}H_{14}N_4O$: C, 60.53; H, 6.47; N, 25.67.

Found: C, 60.27; H, 6.50; N, 25.60.

Example 68

3-(4Ethylamino-2-phenylamino-pyrimidin-5-yl) propionic acid ethyl ester

A mixture of ethyl 3-(4-ethylamino-2-phenylamino-pyrimidin-5-yl)acrylate (152 mg, 0.48 mmol) and 5% palladium on carbon in a solvent mixture of ethanol and tetrahydrofuran was hydrogenated under pressure. The catalyst was filtered off and the filtrate concentrated. The residue was purified by flash chromatography eluting with 2:1 ethyl acetate:hexane to give 72 mg (47%) of 3-(4-ethylamino-2-phenylamino-pyrimidin-5-yl)propionic acid ethyl ester, mp 106–107° C.

Analysis calculated for $C_{17}H_{22}N_4O_2$: C, 64.95; H. 7.05; N, 17.82.

Found: C, 64.90; H, 7.06; N, 17.77.

Example 69

8-Ethyl-2-phenylamino-5,8-dihydro-6H-pyrido[2,3-d]pyrimidin-7-one

A mixture of 3-(4-ethylamino-2-phenylamino-pyrimidin-5-yl)propionic acid ethyl ester (254 mg, 0.81 mmol) and 141 mg (0.93 mmol) of 1,8-diazabicyclo[5.4.0]undec-7-ene in 5 mL of N,N-diisopropylethylamine was heated at reflux overnight. Additional 1,8-diazabicyclo[5.4.0]undec-7-ene (121 µL, 1.0 mmol) was added, and the reaction was heated at reflux for 24 hours. Upon cooling to room temperature, a solid formed that was collected by filtration and purified by flash chromatography eluting with ethyl acetate to give 110 mg (51%) of 3-(4-ethylamino-2-phenylamino-pyrimidin-5-yl)propionic acid ethyl ester, mp 146–147° C.

Analysis calculated for $C_{15}H_{16}N_4O$: C, 67.15; H, 6.01; N, 20.88.

Found: C, 67.06; H, 6.06; N, 20.59.

Example 70

3-(4-Methylamino-2-methanesulfanyl-pyrimidin-5-yl)-acrylonitrile

To a room temperature suspension of sodium hydride (240 mg of a 60% suspension of NaH in oil) in 10 mL of dimethylformamide was added diethyl cyanomethylphosphonate (1.0 mL, 6.17 mmol). The reaction mixture was stirred at room temperature for 15 minutes, then 4-methylamino-2-methanesulfanyl-pyrimidine-5-cabaldeyde (1.02 g, 5.57 mmol) in 10 mL of dimethylformamide was added, and the mixture was stirred at room temperature for 10 minutes. The reaction mixture was partitioned between brine and a 1:1 mixture of hexane and ethyl acetate. The organic layer was washed with water, dried over magnesium sulfate, and concentrated to provide 367 mg (32%) of 3-(4-methylamino-2-methanesulfanyl-pyrimidin-5-yl)acrylonitrile, mp 207–210° C. The residue was purified by flash chromatography eluting with 1:1 ethyl acetate:hexane to provide an additional 19 mg (13%) of product.

Analysis calculated for $C_9H_{10}N_4S$-0.5 $H_2O$: C, 50.20; H, 5.15; N, 26.02.

Found: C, 50.48; H, 4.80; N, 26.28.

Example 71

8-Methyl-2-methanesulfanyl-8H-pyrido[2,3-d] pyrimidin-7-ylideneamine

A mixture of 3-(4-methylamino-2-methanesulfanyl-pyrimidin-5-yl)acrylonitrile (805 mg, 3.91 mmol) and 3 mL (20.13 mmol) of 1,8-diazabicyclo[5.4.0]undec-7-ene in 15 mL of N,N-diisopropylethylamine was heated at reflux overnight. The liquid was decanted from the black oil and purified by flash chromatography eluting with a mixture of 1:3 methanol:ethyl acetate. The fractions containing product were concentrated and a 1:4 mixture of ethyl acetate:hexane was added to the residue. The resultant solid was collected by filtration to give 133 mg (16%) of 8-methyl-2-methanesulfanyl-8H-pyrido[2,3-d]pyrimidin-7-ylideneamine, mp 146–149° C. Concentration of the filtrate provided an additional 405 mg (56%) of product.

Analysis calculated for $C_9H_{10}N_4S$-0.65 $H_2O$: C, 49.59; H, 5.23; N, 25.70.

Found: C, 49.26; H, 4.83; N, 25.48.

Example 72

3-(4-Ethylamino-2-phenylamino-pyrimidin-5yl) acrylonitrile

To a room temperature suspension of sodium hydride (38 mg of a 60% suspension of NaH in oil) in 5 mL of dimethylformamide was added diethyl cyanomethylphosphonate (150 µL, 0.93 mmol). The reaction mixture was stirred at room temperature for 15 minutes, then 4-ethylamino-2-phenylamino-pyrimidine-5-carbaldeyde (200 mg, 0.83 mmol) in 2 mL of dimethylformamide was added, and the mixture was stirred at room temperature for 10 minutes. The reaction mixture was partitioned between brine and ethyl acetate. The organic layer was washed with water, dried over magnesium sulfate, and concentrated in vacuo The residue was purified by flash chromatography eluting with 1:1 ethyl acetate:hexane. The fractions containing product were concentrated, and hexane was added to the residue. The resultant solid was collected by filtration to give 91 mg (43%) of 3-(4-ethylamino-2-phenylamino-pyrimidin-5-yl)acrylonitrile, mp 244–246° C. Concentration of the filtrate provided an additional 68 mg (32%) of product.

Analysis calculated for $C_{15}H_{15}N_5$: C, 67.91; H, 5.70; N, 26.40.

Found: C, 67.80; H, 5.57; N, 26.39.

Example 73

3-(4-Ethylamino-2-phenylamino-pyrimidin-5-yl)-but-2-enoic acid ethyl ester

To a room temperature solution of 4-ethylamino-2-phenylamino-pyrimidine-5-carboxaldehyde (200 mg, 0.83 mmol) in 10 mL of tetrahydrofuran was added (carbethoxyethylidene)triphenylphosphorane (360 mg, 1.0 mmol). The reaction mixture was heated at reflux overnight, cooled, and concentrated in vacuo. The residue was purified by flash chromatography eluting with 1:1 ethyl acetate:hexane. The fractions containing product were concentrated, and 1:2 ethyl acetate:hexane was added to the residue. The resultant solid was collected by filtration to provide 176 mg (65%) of 3-(4-ethylamino-2-phenylamino-pyrimidin-5-yl)-but-2-enoic acid ethyl ester, mp 148–150° C.

Analysis calculated for $C_{18}H_{22}N_4O_2$: C, 66.24; H, 6.79; N, 17.16.

Found: C, 65.95; H, 6.68; N, 17.02.

Example 74

8(1-Ethylpropyl)-2-phenylamino-8H-pyrido[2,3-d]pyrimidin-7-one

To a suspension of NaH (33 mg of a 60% suspension of NaH in mineral oil) in 7 mL of dimethylformamide was added 2-phenylamino-8H-pyrido[2,3-d]pyrimidin-7-one (154 mg, 0.65 mmol). The reaction mixture was heated to 60° C. resulting in a clear solution. The solution was cooled slightly, and 3-bromopentane (125 µL, 1.01 mmol) was added. The reaction was heated at 60° C. for 30 minutes, then cooled to room temperature and partitioned between water and ethyl acetate. The organic layer was dried over magnesium sulfate, filtered, and concentrated in vacuo. The residue was purified by flash chromatography eluting with 1:1 ethyl acetate:hexane to provide 45 mg (23%) of 8-(1-ethylpropyl)-2-phenylamino-8H-pyrido[2,3-d]pyrimidin-7-one, mp 116–118° C.

Analysis calculated for $C_{18}H_{20}4_6O$-0.2 $H_2O$: C, 69.29; H, 6.59; N, 17.95.

Found: C, 69.59; H, 6.41; N, 18.03.

Example 75

8-Isopentyl-2-methanesulfanyl-8H-pyrido[2,3-d]pyrimidin-7-one

To a suspension of NaH (150 mg of a 60% suspension of NaH in mineral oil) in 10 mL of dimethylformamide was added 2-methanesulfanyl-8H-pyrido[2,3-d]pyrimidin-7-one (508 mg, 2.63 mmol). The reaction mixture was heated to 50° C. resulting in an orange solution. The solution was cooled slightly, and 3-bromopentane (500 µL, 3.97 mmol) was added. The reaction was heated at 50° C. for 1 hour, then cooled to room temperature and partitioned between water and ethyl acetate. The organic layer was dried over magnesium sulfate, filtered, and concentrated in vacuo. The residue was purified by flash chromatography eluting with a gradient of 1:3 ethyl acetate:hexane to all ethyl acetate to provide 348 mg (50%) of 8-isopentyl-2-methanesulfanyl-8H-pyrido[2,3-d]pyrimidin-7-one, as an oil.

Example 76

8-(1-Ethylpropyl)-2-methanesulfinyl-8H-pyrido[2,3-d]pyrimidin-7-one

To a room temperature solution of 8-(1-ethylpropyl)-2-methanesulfanyl-8H-pyrido[2,3-d]pyrimidin-7-one (260 mg, 0.99 mmol) in 10 mL of chloroform was added (±)-trans-2-(phenylsulfonyl)-3-phenyloxaziridine (260 mg, 1.11 mmol). The solution was stirred at room temperature overnight then concentrated in vacuo. The residue was purified by flash chromatography eluting with a gradient of ethyl acetate to 10% methanol in ethyl acetate to provide 227 mg (82%) of 8-(1-ethylpropyl)-2-methanesulfinyl-8H-pyrido[2,3-d]pyrimidin-7-one, mp 111–114° C.

Analysis calculated for $C_{13}H_{17}N_3O_2S$: C, 55.89; H, 6.13; N, 15.04.

Found: C, 55.70; H, 6.02; N, 14.95.

Example 77

8-(1-Ethylpropyl)-2-[4-(4-methylpiperazin-1-yl)-phenylamino]-8H-pyrido[2,3-d]pyrimidin-7-one To 8-(1-ethylpropyl)-2-methanesulfinyl-8H-pyrido[2,3-d]pyrimidin-7-one (190 mg, 0.68 mmol) was added 4-(4-methylpiperazin-1-yl)-aniline (260 mg, 1.36 mmol). The reaction mixture was heated at 175° C. for 10 minutes, then cooled to room temperature and partitioned between saturated sodium bicarbonate and chloroform. The organic layer was washed with saturated sodium bicarbonate and brine, dried over magnesium sulfate, filtered, and concentrated in vacuo. The residue was purified by flash chromatography eluting with 10% methanol in ethyl acetate. The fractions containing product were concentrated, the solid was dissolved in chloroform, and a large amount of hexane was added. The solution was cooled in the refrigerator overnight, and the resultant precipitate was collected by filtration to give 101 mg (37%) of product. An analytical sample was obtained by recrystallization from chloroform and hexane to give 41 mg of 8-(1-ethylpropyl)-2-[4-(4-methylpiperazin-1-yl)-phenylamino]-8H-pyrido[2,3-d]pyrimidin-7-one, mp 155–157° C.

Analysis calculated for $C_{23}H_{30}N_6O$-0.10 $H_2O$: C, 67.68; H, 7.41; N, 20.60.

Found: C, 67.31; H, 7.25; N, 20.40.

Example 78

2-(4-Diethylamino-phenylamino)-8-ethyl-8H-pyrido[2,3-d]pyrimidin-7-one

A mixture of 8-ethyl1-2-metlanesulfinyl-8H-pyrido[2,3-d]pyrimidin-7-one (129 mg, 0.54 mmol) and 1 mL of 4-diethylaminoaniline was heated at 175° C. for 10 minutes, then cooled to room temperature and partitioned between saturated sodium bicarbonate and ethyl acetate. The organic layer was washed with saturated sodium bicarbonate and brine, dried over magnesium sulfate, filtered, and concentrated in vacuo. The residue was purified by flash chromatography eluting with ethyl acetate. The fractions containing product were concentrated, and hexane was added to the residue. The resultant precipitate was collected by filtration to give 124 mg (68%) of 2-(4-diethylamino-phenylamino)-8-ethyl-8H-pyrido[2,3-d]pyrimidin-7-one, mp 108–109° C.

Analysis calculated for $C_{19}H_{23}N_5O$: C, 67.63; H, 6.87; N, 20.76.

Found: C, 67.49; H, 6.79; N, 20.78.

Example 79

8-Ethyl-2-(4-morpholin-4-yl-phenylamino)-8H-pyrido[2,3-d]pyrimidin-7-one

A mixture of 8-ethyl-2-methanesulfinyl-8H-pyrido[2,3-d]pyrimidin-7-one (136 mg, 0.57 mmol) and 4-morpholinoaniline (205 mg, 1.15 mmol) was heated at 175° C. for 10 minutes then cooled to room temperature, and ethyl acetate was added. The precipitate was collected by filtration and purified by flash chromatography eluting with ethyl acetate. The fractions containing product were concentrated, and ethyl acetate and hexane were added to the residue. The resultant precipitate was collected by filtration to give 114 mg (57%) yield of 8-ethyl-2-(4-morpholin-4-yl-phenylamino)-8H-pyrido[2,3-d]pyrimidin-7-one, mp 227–228° C.

Analysis calculated for $C_{19}H_{21}N_5O_2$-0.25 $H_2O$: C, 64.14; H, 6.05; N, 19.69.

Found: C, 64.37; H, 5.80; N, 19.78.

Example 80

6-Methyl-2-methylsulfanyl-8H-pyrido[2,3-d]pyrimidin-7-one

A solution of methyl 2-[bis(2,2,2-trifluoroethoxy)phosphinyl]propionate (*Tetrahedron Lett.*, 1983:4405) (526 mg, 1.59 mmol) and 18-crown-6 (1.611 g, 6.10 mmol) in 15 mL of tetrahydrofuran was cooled to −78° C. and potassium bis(trimethylsilyl)amide (3.17 mL of a 0.5 M solution in toluene) was added followed by 4-amino-2-methanesulfanyl-pyrimidine-5-carboxaldehyde (206 mg, 1.22 mmol). The reaction mixture was stirred at −78° C. for 30 minutes then allowed to warm to room temperature. After stirring at room temperature for 2.5 hours, the reaction was quenched with saturated ammonium chloride. The aqueous layer was extracted with ether several times, and the combined extracts were dried over magnesium sulfate, filtered, and concentrated. Hexane and ethyl acetate were added to the residue, and the resultant solid was collected to provide 122 mg (48%) of 6-methyl-2-methylsulfanyl 8H-pyrido[2,3-d]pyrimidin-7-one, mp 243–245° C.

Analysis calculated for $C_9H_9N_3OS$-0.10 $H_2O$: C, 51.72; H, 4.41; N, 20.11.

Found: C, 51.42; H, 4.36; N, 19.96.

Example 81

8-Ethyl-6-methyl-2-methylsulfanyl-8H-pyrido[2,3-d]pyrimidin-7-one

To a suspension of NaH (261 mg of a 60% suspension of NaH in mineral oil) in 40 mL of dimethylformamide was added 6-methyl-2-methylsulfanyl-8H-pyrido[2,3-d]pyrimidin-7-one (926 mg, 4.48 mmol). The reaction mixture was heated to 50° C. resulting in a clear solution. The solution was cooled slightly, and iodoethane (491 μL, 6.14 mmol) was added. The reaction was heated at 50° C. for 10 minutes, then cooled to room temperature and partitioned between ice water and ethyl acetate. The organic layer was dried over magnesium sulfate, filtered, and concentrated in vacuo. The residue was partitioned between hexane and water. The organic layer was dried over magnesium sulfate, filtered, and concentrated in vacuo. Hexane was added and the resultant solid collected by filtration to provide 824 mg (78%) of 8-ethyl-6-methyl-2-methylsulfanyl-8H-pyrido[2,3-d]pyrimidin-7-one, mp 84–86° C.

Analysis calculated for $C_{11}H_{13}N_3OS$-0.05 $H_2O$-0.05 ethyl acetate: C, 55.93; H, 5.62; N, 17.48.

Found: C, 56.11; H, 5.62; N, 17.21.

Example 82

8-Ethyl-2-methanesulfinyl-6-methyl-8H-pyrido[2,3-d]pyrimidin-7-one

To a room temperature solution of 8-ethyl-6-methyl-2-methylsulfanyl-8H-pyrido[2,3-d]pyrimidin-7-one (789 mg, 3.36 mmol) in 50 mL of chloroform was added (±)-trans-2-(phenylsulfonyl)-3-phenyloxaziridine (1.06 g, 4.06 mmol). The solution was stirred at room temperature overnight then concentrated in vacuo. The residue was purified by flash chromatography eluting with a gradient of ethyl acetate to 10% methanol in ethyl acetate to provide 743 mg (88%) of 8-ethyl-6-methyl-2-methylsulfinyl-8H-pyrido[2,3-d]pyrimidin-7-one, mp 148–150° C.

Analysis calculated for $C_{11}H_{13}N_3O_2S$-0.20 $H_2O$: C, 51.85; H, 5.26; N, 16.49.

Found: C, 52.22; H, 5.14; N, 16.09.

Example 83

8-Ethyl-6-methyl-2-phenylamino-8H-pyrido[2,3-d]pyrimidin-7-one

A mixture of 8-ethyl-6-methyl-2-methylsulfinyl-8H-pyrido[2,3-d]pyrimidin-7-one (123 mg, 0.49 mmol) and 1 mL of aniline was heated at 175° C. for 20 minutes. The reaction was cooled to room temperature and partitioned between ethyl acetate and saturated sodium bicarbonate. The organic layer was washed with brine, dried over magnesium sulfate, filtered, and concentrated. Hexane was added to the residue, and the resultant solid was collected by filtration and purified by flash chromatography eluting with ethyl acetate to provide 21 mg (15%) of 8-ethyl-6-methyl-2-phenylamino-8H-pyrido[2,3-d]pyrimidin-7-one, mp 178–180° C.

Analysis calculated for $C_{16}H_{16}N_4O$-0.10 $H_2O$-0.05 ethyl acetate: C, 67.92; H, 5.80; N, 19.57.

Found: C, 67.64; H, 5.50; N, 19.18.

Example 84

8-Ethyl-6-methyl-2-[4-(4-methyl-piperazin-1-yl)-phenylamino-8H-pyrido[2,3-d]pyrimidin-7-one A mixture of 8-ethyl-6-methyl-2-methylsulfinyl-8H-pyrido[2,3-]pyrimidin-7-one (154 mg, 0.61 mmol) and 234 mg (1.23 mmol) of 4-(4-methyl-piperazin-1-yl)-aniline was heated at 175° C. for 30 minutes. The reaction was cooled to 100° C., and water was added. The water was decanted off, and the gum was dissolved in chloroform and washed with saturated sodium bicarbonate followed by brine. The organic layer was dried over magnesium sulfate, filtered, and concentrated. The residue was purified by flash chromatography eluting with 10% methanol in chloroform. The fractions containing product were collected and concentrated. The residue was recrystallized from hexane and ethyl acetate and then recrystallized again from chloroform and hexane to provide 76 mg (33%) of 8-ethyl-6-methyl-2-[4-(4-methyl-piperazin-1-yl)-phenylamino-8H-pyrido[2,3-d] pyrimidin-7-one, mp 198–200° C.

Analysis calculated for $C_{21}H_{26}N_6O\cdot0.3\ H_2O$: C, 65.73; H, 6.94; N, 21.91.

Found: C, 65.35; H, 6.66; N, 21.84.

Example 85

8-sec-Butyl-2-phenylamino-8H-pyrido[2,3-d]
pyrimidin-7-one

To a suspension of NaH (47 mg of a 60% suspension of NaH in mineral oil) in 6 mL of dimethylformamide was added 2-phenylamino-8H-pyrido[2,3-d]pyrimidin-7-one (202 mg, 0.85 mmol). The reaction mixture was heated to 50° C. to 60° C. resulting in a yellow solution. The solution was cooled slightly, and 2-iodobutane (140 μL, 1.22 mmol) was added. The reaction was heated at 50° C. for 20 minutes, then cooled to room temperature and partitioned between water and ethyl acetate. The organic layer was dried over magnesium sulfate, filtered, and concentrated in vacuo. Purification by flash chromatography eluting with 2:1 ethyl acetate:hexane gave 29 mg (12%) of 8-sec-butyl-2-phenylamino-8H-pyrido[2,3-d]pyrimidin-7-one, mp 155–156° C.

Analysis calculated for $C_{17}H_{18}N_4O$: C, 69.37; H, 6.16; N, 19.03.

Found: C, 69.18; H, 5.92; N, 18.91.

Example 86

8-(2-Methoxyethyl)-2-phenylamino-8H-pyrido[2,3-d]pyrimidin-7-one

To a suspension of NaH (49 mg of a 60% suspension of NaH in mineral oil) in 6 mL of dimethylformamide was added 2-phenylamino-8H-pyrido[2,3-d]pyrimidin-7-one (200 mg, 0.84 mmol). The reaction mixture was heated to 50° C. resulting in a yellow solution. The solution was cooled slightly, and 2-bromoethylmethyl ether (140 μL, 1.49 mmol) was added. The reaction mixture was heated at 50° C. for 10 minutes, then cooled to room temperature and partitioned between water and ethyl acetate. The organic layer was dried over magnesium sulfate, filtered, and concentrated in vacuo. Purification by flash chromatography eluting with a gradient of 2:1 hexane:ethyl acetate to all ethyl acetate gave 140 mg (56%) of 8-(2-methoxyethyl)-2-phenylamino-8H-pyrido[2,3-d]pyrimidin-7-one, mp 179–180° C.

Analysis calculated for $C_{16}H_{16}N_4O_2\cdot0.2\ H_2O$: C, 64.07; H, 5.51; N, 18.68.

Found: C, 64.02; H, 5.36; N, 18.51.

Example 87

8-(3-Phenoxypropyl)-2-phenylamino-8H-pyrido[2,3-d]pyrimidin-7-one

To a suspension of NaH (51 mg of a 60% suspension of NaH in mineral oil) in 6 mL of dimethylformamide was added 2-phenylamino-8H-pyrido[2,3-d]pyrimidin-7-one (200 mg, 0.84 mmol). The reaction mixture was heated to 50° C. resulting in a yellow solution. The solution was cooled slightly, and 3-phenoxypropyl bromide (230 μL, 1.47 mmol) was added. The reaction mixture was heated at 50° C. for 10 minutes, then cooled to room temperature and partitioned between water and ethyl acetate. The organic layer was dried over magnesium sulfate, filtered, and concentrated in vacuo. Methanol and ethyl acetate were added to the residue, and 60 mg (19%) of 8-(3-phenoxypropyl)-2-phenylamino-8H-pyrido[2,3-d]pyrimidin-7-one was collected by filtration, mp 175–176° C.

Analysis calculated for $C_{22}H_{20}N_4O_2$: C, 70.95; H, 5.41; N, 15.04.

Found: C, 70.67; H, 5.42; N, 14.98.

Example 88

8-Ethyl-2-(4-fluorophenylamino)-8H-pyrido[2,3-d]
pyrimidin-7-one

A mixture of 8-ethyl-2-methylsulfinyl-8H-pyrido[2,3-d]pyrimidin-7-one (145 mg, 0.61 mmol) and 500 μL of 4-fluoroaniline was heated at 175° C. for 10 minutes. The reaction mixture was cooled to room temperature, and the resultant solid was washed with 1:1 hexane:ethyl acetate. The solid was purified by flash chromatography eluting with ethyl acetate to provide 85 mg (49%) of 8-ethyl-2-(4-fluorophenylamino)-8H-pyrido[2,3-d]pyrimidin-7-one, mp 215–217° C.

Analysis calculated for $C_{15}H_{13}N_4OF$: C, 63.37; H, 4.61; N, 19.71.

Found: C, 62.98; H, 4.37; N, 19.60.

Example 89

8-Ethyl-2-(3-fluorophenylamino)-8H-pyrido[2,3-d]
pyrimidin-7-one

A mixture of 8-ethyl-2-methylsulfinyl-8H-pyrido[2,3-d]pyrimidin-7-one (112 mg, 0.47 mmol) and 500 μL of 3-fluoroaniline was heated at 175° C. for 10 minutes. The reaction mixture was cooled to room temperature and partitioned between ethyl acetate and saturated sodium bicarbonate. The organic layer was washed with brine, dried over magnesium sulfate, filtered, and concentrated in vacuo. The residue was purified by flash chromatography eluting with ethyl acetate. Recrystallization from chloroform and hexane provided 33 mg (25%) of 8-ethyl-2-(3-fluorophenylamino)-8H-pyrido[2,3-d]pyrimidin-7-one, mp 210–212° C.

Analysis calculated for $C_{15}H_{13}N_4OF\cdot0.1\ H_2O\cdot0.1$ ethyl acetate: C, 62.73; H, 4.75; N, 19.01.

Found: C, 62.70; H, 4.64; N, 18.80.

Example 90

8-Ethyl-2-(3-fluoro-4-methoxyphenylamino)-8H-pyrido[2,3-d]pyrimidin-7-one

A mixture of 8-ethyl-2-methylsulfinyl-8H-pyrido[2,3-d]pyrimidin-7-one (124 mg, 0.52 mmol) and 148 mg (1.05 mmol) of 3-fluoro-4-methoxyaniline was heated at 175° C. for 10 minutes. The reaction mixture was cooled to room temperature and partitioned between ethyl acetate and saturated sodium bicarbonate. The organic layer was washed with brine, dried over magnesium sulfate, filtered, and concentrated in vacuo. The residue was purified by flash chromatography eluting with ethyl acetate. Recrystallization from ethyl acetate and hexane provided 67 mg (41 %) of 8-ethyl-2-(3-fluoro-4-methoxyphenylamino)-8H-pyrido[2,3-d]pyrimidin-7-one, mp 196–198° C.

Analysis calculated for $C_{16}H_{15}N_4O_2F\cdot0.3\ H_2O$: C, 60.11; H, 4.88; N, 17.53.

Found: C, 60.13; H, 4.78; N, 17.15.

Example 91

8-Ethyl-2-(3-fluoro-2-methoxyphenylamino)-8H-pyrido[2,3-d]pyrimidin-7-one

A mixture of 8-ethyl-2-methylsulfinyl-8H-pyrido[2,3-d] pyrimidin-7-one (133 mg, 0.56 mmol) and 500 μL of 3-fluoro-2-methoxyaniline was heated at 175° C. for 20 minutes. The reaction mixture was cooled to room temperature and partitioned between ethyl acetate and saturated sodium bicarbonate. The organic layer was washed with brine, dried over magnesium sulfate, filtered, and concentrated in vacuo. The residue was purified by flash chromatography eluting with ethyl acetate. Recrystallization from ethyl acetate and hexane provided 28 mg (16%) of 8-ethyl 2-(3-fluoro-2-methoxyphenylamino)-8H-pyrido[2,3-d] pyrimidin-7-one, mp 92–93° C.

Analysis calculated for $C_{16}H_{15}N_4O_2F\cdot 0.15\ H_2O$: C, 60.63; H, 4.83; N, 17.68.

Found: C, 60.31; H, 4.52; N, 17.42.

Example 92

8-Ethyl-2-(2-methoxyphenylamino)-8H-pyrido[2,3-d]pyrimidin-7-one

A mixture of 8-ethyl-2-methylsulfinyl-8H-pyrido[2,3-d] pyrimidin-7-one (140 mg, 0.59 mmol) and 500 μL of 2-methoxyaniline was heated at 175° C. for 20 minutes. The reaction mixture was cooled to room temperature and partitioned between chloroform and saturated sodium bicarbonate. The organic layer was washed with brine, dried over magnesium sulfate, filtered, and concentrated in vacuo. The residue was purified by flash chromatography eluting with ethyl acetate. Recrystallization from ethyl acetate and hexane provided 60 mg (34%) of 8-ethyl-2-(2-methoxyphenyl-amino)-8H-pyrido[2,3-d]pyrimidin-7-one, mp 126–128° C.

Analysis calculated for $C_{16}H_{16}N_4O_2\cdot 0.2\ H_2O$: C, 64.09; H, 5.47; N, 18.69.

Found: C, 64.10; H, 5.36; N, 18.44.

Example 93

2-(4-Dimethylamino-phenylamino)-8-ethyl-8H-pyrido[2,3-d]pyrimidin-7-one

A mixture of 8-ethyl-2-methanesulfinyl-8H-pyrido[2,3-d] pyrimidin-7-one (155 mg, 0.65 mmol) and 500 μL of 4-dimethylaminoaniline was heated at 175° C. for 10 minutes, then cooled to room temperature and partitioned between saturated sodium bicarbonate and ethyl acetate. The organic layer was washed with brine, dried over magnesium sulfate, filtered, and concentrated in vacuo. The resultant solid was washed with hexane and ethyl acetate then purified by flash chromatography eluting with ethyl acetate. The fractions containing product were concentrated and a 2:1 mixture of hexane and ethyl acetate was added to the residue. The resultant precipitate was collected by filtration to give 110 mg (50%) of 2-(4-dimethylamino-phenylamino)-8-ethyl-8H-pyrido[2,3-d]pyrimidin-7-one, mp 189–191° C.

Analysis calculated for $C_{17}H_{19}N_5O\cdot 0.2\ H_2O\cdot 0.25$ ethyl acetate: C, 64.55; H, 6.40; N, 20.92.

Found: C, 64.55; H, 6.32; N, 21.10.

Example 94

2-Methanesulfanyl-4-phenylamino-pyrimidine-5-carboxylic acid ethyl ester

To a room temperature solution of 4-chloro-2-methanesulfanyl-pyrimidine-5-carboxylic acid ethyl ester (9.25 g, 40.0 mmol) in 100 mL of tetrahydrofuran was added 16 mL of triethylamine followed by aniline (4.0 mL, 43.8 mmol). The solution was stirred at room temperature overnight. The white solid was removed by filtration washing with ethyl acetate. The filtrate was concentrated in vacuo and partitioned between chloroform and saturated aqueous sodium bicarbonate. The organic layer was dried over magnesium sulfate, filtered, and concentrated. A solution of 2:1 hexane:ethyl acetate was added to the residue, and the resultant white solid was collected to provide 7.07 g (60%) of product. An additional 2.18 g (18%) was obtained from the filtrate. Recrystallization from hexane and ethyl acetate provided an analytical sample of 2-methanesulfanyl-4-phenylamino-pyrimidine-5-carboxylic acid ethyl ester, mp 86–87.5° C.

Analysis calculated for $C_{14}H_{15}N_3O_2S$: C, 58.11; H, 5.23; N, 14.52.

Found: C, 57.93; H, 5.27; N, 14.46.

Example 95

(2-Methanesulfanyl-4-phenylamino-pyrimidin-5yl)-methanol

A solution of 2-methanesulfanyl-4-phenylamino-pyrimidine-5-carboxylic acid ethyl ester (7.25 g, 25.1 mmol) in 100 mL of tetrahydrofuran was added dropwise to a room temperature suspension of lithium aluminum hydride (1.55 g, 40.9 mmol) in 100 mL of tetrahydrofuran. After 10 minutes, an additional 1.00 g of lithium aluminum hydride was added to the reaction mixture, and stirring was continued for 1.5 hours. The reaction was carefully quenched with isopropanol followed by 6 mL of water, 10 mL of 15% NaOH, and 20 mL of water, and the mixture was stirred for 1.5 hours. The white precipitate was removed by filtration washing with ethyl acetate. The filtrate was washed with water, dried over magnesium sulfate, filtered, and concentrated in vacuo. Purification by flash chromatography eluting with ethyl acetate provided 2.22 g (36%) of (4 ethylamino-2-methanesulfanyl-pyrimidin-5-yl)-methanol, mp 127–128° C.

Analysis calculated for $C_{12}H_{13}N_3OS$: C, 58.28; H, 5.30; N, 16.99.

Found: C, 58.15; H, 5.09; N, 16.90.

Example 96

2-Methanesulfanyl-4-phenylamino-pyrimidine-5-carboxaldehyde

To (4-ethylamino-2-methanesulfanyl-pyrimidin-5-yl)-methanol (2.80 g, 11.4 mmol) in 400 mL of chloroform was added manganese oxide (3.95 g, 45.4 mmol). The suspension was stirred at room temperature overnight. The mixture was filtered through celite washing with chloroform. The filtrate was concentrated in vacuo to give 2.73 g (98%) of 2-methanesulfanyl-4-phenylamino-pyrimidine-5-carboxaldehyde, mp 89–90° C.

Analysis calculated for $C_{12}H_{11}N_3OS$: C, 58.76; H, 4.52; N, 17.13.

Found: C, 58.56; H, 4.69; N, 17.10.

Example 97

Ethyl 3-(2-Methanesulfanyl-4-phenylamino-pyrimidin-5-yl)acrylate

To a room temperature solution of 2-methanesulfanyl-4-phenylamino pyrimidine-5-carboxaldehyde (1.00 g, 4.08 mmol) in 20 mL of tetrahydrofuran was added (carbethoxymethylene)triphenylphosphorane (1.82 g, 5.22 mmol). The reaction mixture was heated at reflux for 70 minutes, then concentrated in vacuo and partitioned between ethyl acetate and 1N hydrochloric acid. The organic layer was extracted with two additional portions of 1N hydrochloric acid, and the acid layers were combined and neutralized with saturated sodium bicarbonate. The product was extracted into ethyl acetate, dried over magnesium sulfate, filtered, and concentrated in vacuo. The residue was purified by flash chromatography eluting with ethyl acetate to provide 988 mg (77%) of ethyl 3-(2-methanesulfanyl-4-phenylamino-pyrimidin-5-yl)acrylate as a yellow oil.

Example 98

2-Methanesulfanyl-8-phenyl-8H-pyrido[2,3-d]pyrimidin-7-one

To a room temperature solution of ethyl 3-(2-methanesulfanyl-4-phenylamino pyrimidin-5-yl)acrylate (358 mg, 1.14 mmol) in 5 mL of N,N-diisopropylethylamine was added 191 µL of 1,8-diazabicyclo[5.4.0]undec-7-ene. The reaction mixture was heated at reflux overnight then cooled to room temperature. The resultant solid was collected by filtration and combined with the gum remaining in the flask. This combined material was purified by flash chromatography eluting with ethyl acetate to provide 176 mg (57%) of 2-methanesulfanyl-8-phenyl-8H-pyrido[2,3-d]pyrimidin-7 one, mp 176–178° C.

Analysis calculated for $C_{14}H_{11}N_3OS$-0.05 $H_2O$: C, 60.43; H, 4.32; N, 15.11.

Found: C, 60.43; H, 3.97; N, 14.82.

Example 99

2-Methanesulfinyl-8-phenyl-8H-pyrido[2,3-d]pyrimidin-7-one

To a room temperature solution of 2-methanesulfanyl-8-phenyl-8H-pyrido[2,3 d]pyrimidin-7-one (457 mg, 1.70 mmol) in 30 mL of chloroform was added (±)-trans-2-(phenylsulfonyl)-3-phenyloxaziridine (536 mg, 2.06 mmol). The solution was stirred at room temperature overnight then concentrated in vacuo. The residue was purified by flash chromatography eluting with a gradient of ethyl acetate to 10% methanol in ethyl acetate to provide 397 mg (82%) of 2-methanesulfinyl-8-phenyl-8H-pyrido[2,3-d]pyrimidin-7-one, mp 248–250° C.

Analysis calculated for $C_{14}H_{11}N_3O_2S$-0.02 $H_2O$: C, 58.21; H, 3.95; N, 14.55.

Found: C, 58.04; H, 3.91; N, 14.36.

Example 100

2-Ethylamino-8-phenyl-8H-pyrido[2,3-d]pyrimidin-7-one

A mixture of 2-methanesulfinyl-8-phenyl-8H-pyrido[2,3-d]pyrimidin-7-one (81 mg, 0.28 mmol) and 1.5 mL of aqueous ethyl amine was stirred at room temperature for 10 minutes then partitioned between water and ethyl acetate. The organic layer was washed with saturated sodium bicarbonate and brine, dried over magnesium sulfate, filtered, and concentrated in vacuo to give 54 mg (72%) of 2-ethylamino-8-phenyl-8H-pyrido[2,3-d]pyrimidin-7-one, mp 193–195° C.

Analysis calculated for $C_{15}H_{14}N_4O$: C, 67.65; H, 5.30; N, 21.04.

Found: C, 67.48; H, 5.01; N, 20.68.

Example 101

2-Phenylamino-8-phenyl-8H-pyrido[2,3-]pyrimidin-7-one

A mixture of 2-methanesulfinyl-8-phenyl-8H-pyrido[2,3-d]pyrimidin-7-one (197 mg, 0.69 mmol) and 1 mL of aniline was heated at 175° C. for 10 minutes then cooled to room temperature. Hexane and ethyl acetate were added, and the solid was collected by filtration and purified by flash chromatography eluting with ethyl acetate. The fractions containing product were concentrated, and the residue was recrystallized first from hexane and ethyl acetate then from chloroform and ethyl acetate to provide 85 mg (39%) of 2-phenylamino-8-phenyl-8H-pyrido[2,3-d]pyrimidin-7-one, mp 300–302° C.

Analysis calculated for $C_{19}H_{14}N_4O$-0.25 $H_2O$: C, 71.59; H, 4.55; N, 17.58.

Found: C, 71.91; H, 4.39; N, 17.59.

Example 102

4-Cyclopentylamino-2-methanesulfanyl-pyrimidine-5-carboxylic acid ethyl ester

To a room temperature solution of 4-chloro-2-methanesulfanyl-pyrimidine-5-carboxylic acid ethyl ester (12.48 g, 53.8 mmol) in 150 mL of tetrahydrofuran was added 22 mL of triethylamine followed by cyclopentylamine (6.70 g, 77.0 mmol). The solution was stirred at room temperature for 1 hour. The white solid was removed by filtration washing with ethyl acetate. The filtrate was concentrated in vacuo and partitioned between ethyl acetate and saturated aqueous sodium bicarbonate. The organic layer was washed with brine, dried over magnesium sulfate, filtered, and concentrated. A solution of 2:1 hexane:ethyl acetate was added to the residue, and the resultant white solid was collected to provide 13.3 g (88%) of 4-cyclopentylamino-2-methanesulfanyl-pyrimidine-5-carboxylic acid ethyl ester as an oil.

Analysis calculated for $C_{13}H_{19}N_3O_2S$: C, 55.49; H, 6.81; N, 14.93.

Found: C, 55.59; H, 6.72; N, 14.85.

Example 103

(4-Cyclopentylamino-2-methanesulfanyl-pyrimidin-5-yl)-methanol

A solution of 4-cyclopentylamino-2-methanesulfanyl-pyrimidine-5-carboxylic acid ethyl ester (13.0 g, 46.3 mmol) in 50 mL of tetrahydrofuran was added dropwise to a room temperature suspension of lithium aluminum hydride (3.2 g, 84.2 mmol) in 150 mL of tetrahydrofuran. The reaction mixture was stirred at room temperature for 20 minutes, then carefully quenched with 6 mL of water, followed by 6 mL of 15% NaOH and 19 mL of water. After stirring for 1 hour, the white precipitate was removed by filtration washing with ethyl acetate. The filtrate was concentrated in vacuo, and hexane and ethyl acetate were added to the residue. Filtration of the white solid provided 8.39 g (76%) of (4-cyclopentylamino-2-methanesulfanyl-pyrimidin-5-yl)-methanol, mp 127–128° C.

Analysis calculated for $C_{11}H_{17}N_3OS$-0.1 $H_2O$: C, 54.79; H, 7.19; N, 17.43.

Found: C, 54.68; H, 7.12; N, 17.23.

Example 104

4-Cyclopentylamino-2-methanesulfanyl-pyrimidine-5-carboxaldehyde

To (4-cyclopentylamino-2-methanesulfanyl-pyrimidin-5-yl)-methanol (8.00 g, 33.5 mmol) in 400 mL of chloroform was added manganese oxide (18.5 g, 213 mmol). The suspension was stirred at room temperature overnight. An additional amount of manganese oxide (2.5 g, 29 mmol) was added, and stirring was continued for 2.5 h. The mixture was filtered through celite washing with chloroform. The filtrate was concentrated in vacuo to give 7.93 g (99%) of 4-cyclopentylamino-2-methanesulfanyl-pyrimidine-5-carboxaldehyde as an oil.

Analysis calculated for $C_{11}H_{15}N_3OS$: C, 55.67; H, 6.37; N, 17.71.

Found: C, 55.60; H, 6.24; N, 17.70.

Example 105

Ethyl 3-(4-Cyclopentylamino-2-methanesulfanyl-pyrimidin-5-yl)acrylate

To a room temperature solution of 4-cyclopentylamino-2-methanesulfanyl-pyrimidine-5-carboxaldehyde (7.74 g, 32.7 mmol) in 110 mL of tetrahydrofuran was added (carbethoxymethylene)triphenylphosphorane (15.0 g, 43.1 mmol). The reaction mixture was heated at reflux for 1.5 hours, then cooled to room temperature and partitioned between ethyl acetate and 1N hydrochloric acid. Concentrated aqueous sodium hydroxide was added to the acid layer followed by extraction of the product into ethyl acetate. The organic layer was dried over magnesium sulfate, filtered, and concentrated in vacuo. The residue was purified by flash chromatography eluting with 4:1 hexane:ethyl acetate to provide 6.58 g (66%) of ethyl 3-(4-cyclopentylamino-2-methanesulfanyl-pyrimidin-5-yl)acrylate, mp98–101° C.

Analysis calculated for $C_{15}H_{21}N_3O_2S$: C, 58.61; H, 6.89; N, 13.67.

Found: C, 58.57; H, 6.83; N, 13.52.

Example 106

8-Cyclopentyl-2-methanesulfanyl-8H-pyrido[2,3-d]pyrimidin-7-one

A mixture of ethyl 3-(4-cyclopentylamino-2-methanesulfanyl-pyrimidin-5-yl)acrylate (1.42 g, 4.62 mmol) and 5 mL of 1,8-diazabicyclo[5.4.0]undec-7-ene was heated at reflux for 30 minutes. The reaction mixture was directly purified by flash chromatography eluting with a gradient of 1:1 hexane:ethyl acetate to all ethyl acetate to provide 677 mg (56%) of 8-cyclopentyl-2-methanesulfanyl-8H-pyrido[2,3-d]pyrimidin-7-one, mp 100–102° C.

Analysis calculated for $C_{13}H_{15}N_3OS$: C, 59.75; H, 5.79; N, 16.08.

Found: C, 59.59; H, 5.71; N, 15.95.

Example 107

8-Cyclopentyl-2-methanesulfinyl-8H-pyrido[2,3-d]pyrimidin-7-one

To a room temperature solution of 8-cyclopentyl-2-methanesulfanyl-8H-pyrido[2,3-d]pyrimidin-7-one (215 mg, 0.82 mmol) in 10 mL of chloroform was added (±)-trans-2(phenylsulfonyl)-3-phenyloxaziridine (240 mg, 0.92 mmol). The solution was stirred at room temperature overnight then concentrated in vacuo. Ethyl acetate was added to the residue, and the resultant solid was collected by filtration to provide 134 mg (59%) of 8-cyclopentyl-2-methanesulfinyl-8H-pyrido[2,3-d]pyrimidin-7-one, mp 170–173° C.

Analysis calculated for $C_{13}H_{15}N_3O_2S$: C, 56.30; H, 5.45; N, 15.15.

Found: C, 56.11; H, 5.36; N, 14.91.

Example 108

8-Cyclopentyl-2-phenylamino-8H-pyrido[2,3-d]pyrimidin-7-one

A mixture of 8-cyclopentyl-2-methanesulfinyl-8H-pyrido[2,3-d]pyrimidin-7-one (257 mg, 0.93 mmol) and 2 mL of aniline was heated at reflux for 20 minutes then cooled to room temperature. Most of the aniline was removed under high vacuum. The residue was purified by flash chromatography eluting with a gradient of 3:2 hexane:ethyl acetate to all ethyl acetate to provide 124 mg of product. Recrystallization from hexane and ethyl acetate gave 72 mg (26%) of 8-cyclopentyl-2-phenylamino-8H-pyrido[2,3-d]pyrimidin-7-one, mp 188–192° C.

Analysis calculated for $C_{18}H_{18}N_4O \cdot 0.3\ H_2O$: C, 69.34; H, 6.01; N, 17.97.

Found: C, 69.06; H, 5.78; N, 17.95.

Examples 109–271

The following invention compounds were similarly prepared by following the general procedures of the foregoing examples.

Example 109

8-Ethyl-2-[3-(4-methyl-piperazin-1-yl)-propylamino-8H-pyrido[2,3-d]pyrimidin-7-one, mp 85–85° C.

Example 110

8-Ethyl-2-(4-pyrrol-1-yl-phenylamino)-8H-pyrido[2,3-d]pyrimidin-7-one, mp 220–222° C.

Example 111

8-Isopropyl-2-(4-methoxy-phenylamino)-8H-pyrido[2,3-d]pyrimidin-7-one, mp 153–155° C.

Example 112

2-(4-Hydroxy-phenylamino)-8-isopropyl-8H-pyrido[2,3-d]pyrimidin-7-one, mp 226–228° C.

Example 113

2-[4-(4-Methyl-piperazin-1-yl)-phenylamino]-8-phenyl-8H-pyrido[2,3-d]pyrimidin-7-one, mp 259–262° C.

Example 114

8-Cyclopentyl-2-[4-(4-methyl-piperazin-1-yl)-phenylamino]-8H-pyrido[2,3-d]pyrimidin-7-one, mp 175–177° C.

Example 115

8-(3-Benzyloxy-propyl)-2-[4-(4-methyl-piperazin-1-yl)-phenylamino]-8H-pyrido[2,3-d]pyrimidin-7-one, mp 148–150° C.

Example 116

8-(3-Benzyloxy-propyl)-2-[4-(2-diethylamino-ethoxy)-phenylamino]-8H-pyrido[2,3-d]pyrimidin-7-one, mp 70–72° C.

Example 117

8-Cyclopentyl-2[4-(2-diethylamino-ethoxy)-phenylamino]-8H-pyrido[2,3-d]pyrimidin-7-one, mp 105–107° C.

Example 118

2-[4-(2-Diethylamino-ethoxy)-phenylamino]-8-phenyl-8H-pyrido[2,3-d]pyrimidin-7-one, mp 165–167° C.

Example 119

4-Cyclohexylamino-2-methylsulfanyl-pyrimidine-5-carboxylic acid ethyl ester, oil.

Example 120

4-Cyclopropylamino-2-methylsulfanyl-pyrimidine-5-carboxylic acid ethyl ester, oil.

Example 121

(4-Cyclohexylamino-2-methylsulfanyl-pyrimidin-5-yl)-methanol, mp 127–129° C.

Example 122

4-Cyclohexylamino-2-methylsulfanyl-pyrimidine-5-carboxaldehyde, oil.

Example 123

3-(4-Cyclohexylamino-2-methysulfanyl-pyrimidin-5-yl)-acrylic acid ethyl ester

Example 124

(4-Cyclopropylamino-2-methylsulfanyl-pyrimidin-5-yl)-methanol, mp 134–135° C.

Example 125

4-Cyclopropylamino-2-methylsulfanyl-pyrimidine-5-carboxaldehyde, mp 63–64° C.

Example 126

8-Cyclohexyl-2-methylsulfanyl-8H-pyrido[2,3-d]pyrimidin-7-one, mp 131–132° C.

Example 127

8-Cyclohexyl-2-methanesulfinyl-8H-pyrido[2,3-d]pyrimidin-7-one, mp 187–190° C.

Example 128

3-(4-Cyclopropylamino-2-methylsulfanyl-pyrimidin-5-yl)-acrylic acid ethyl ester, oil.

Example 129

8-Cyclopropyl-2-methylsulfanyl-8H-pyrido[2,3-d]pyrimidin-7-one, mp 137–139° C.

Example 130

8-Cyclopropyl-2-methanesulfinyl-8H-pyrido[2,3d]pyrimidin-7-one, mp 210–212° C.

Example 131

8-Cyclohexyl-2-phenylamino-8H-pyrido[2,3-d]pyrimidin-7-one, mp 202–204° C.

Example 132

8-Cyclohexyl-2-[4-(2-diethylamino-ethoxy)-phenylamino]-8H-pyrido[2,3-d]pyrimidin-7-one, mp 135–137° C.

Example 133

8-Cyclohexyl-2[4-(4-methyl-piperazin-1-yl)-phenylamino]-8H-pyrido[2,3-d]pyrimidin-7-one, mp 205–207° C.

Example 134

8-Cyclopropyl-2-[4-(2-diethylamino-ethoxy)-phenylamino]-8H-pyrido[2,3-d]pyrimidin-7-one, mp 119–121° C.

Example 135

8-Cyclopropyl-2-phenylamino-8H-pyrido[2,3-d]pyrimidin-7-one, mp 191–193° C.

Example 136

8-Cyclopropyl-2-[4-(4-methyl-piperazin-1-yl)-phenylamino]-8H-pyrido[2,3-d]pyrimidin-7-one, mp 210–211° C.

Example 137

8-(2-Benzyloxy-ethyl)-2-methanesulfinyl-8H-pyrido[2,3-d]pyrimidin-7-one, mp 118–120° C.

Example 138

8-(3-Benzyloxy-propyl)-2-(4-dimethylamino-phenylamino)-8H-pyrido[2,3-d]pyrimidin-7-one, mp 144–146° C.

Example 139

8-(2-Benzyloxy-ethyl)-2-[4-(2-diethylamino-ethoxy)-phenylamino]-8H-pyrido[2,3-d]pyrimidin-7-one, mp 95–97° C.

Example 140

8-(2-Benzyloxy-ethyl)-2-[4-(4-methyl-piperazin-1-yl)-phenylamino]-8H-pyrido[2,3-d]pyrimidin-7-one, mp 183–185° C.

Example 141

8-Isopropyl-2-[4-(2-morpholin-4-yl-ethoxy)-phenylamino]-8H-pyrido[2,3-d]pyrimidin-7-one, mp 118–119° C.

Example 142

8-Cyclohexyl-2-(4-piperidin-1-yl-phenylamino)-8H-pyrido[2,3-d]pyrimidin-7-one, mp 198–200° C.

Example 143

8-Cyclohexyl-2-{4-[4-(2-hydroxy-ethyl)-3,5-dimethyl-piperazin-1-yl]-phenylamino}-8H-pyrido[2,3-d]pyrimidin-7-one, mp 175–177° C.

Example 144

8-Cyclohexyl-2-{4-[4-(3-dimethylamino-propyl)-piperazin-1-yl]-phenylamino}-8H-pyrido[2,3-d]pyrimidin-7-one, mp 169–170° C.

Example 145

8-Cyclohexyl-2-[4-(3,5-dimethyl-piperazin-1-yl)-phenylamino-8H-pyrido[2,3-d]pyrimidin-7-one, mp 237–239° C.

Example 146

4-Cycloheptylamino-2-methylsulfanyl-pyrimidine-5-carboxylic acid ethyl ester

Example 147

8-Cyclohexyl-2-(4-dimethylamino-phenylamino)-8H-pyrido[2,3-d]pyrimidin-7-one, mp 204–205° C.

Example 148

8-Cyclohexyl-2-(4-fluoro-phenylamino)-8H-pyrido[2,3-d]pyrimidin-7-one, mp 209–211° C.

Example 149

(4-Cycloheptylamino-2-methylsulfanyl-pyrimidin-5-yl)-methanol, mp 141–143° C.

Example 150

8-Cyclohexyl-2-[4-(2-diethylamino-ethoxy)-3-methyl-phenylamino]-8H-pyrido[2,3-d]pyrimidin-7-one, mp 119–121° C.

Example 151

8-Cycloheptyl-2-methylsulfanyl-8H-pyrido[2,3-d]pyrimidin-7-one, mp 135–136° C.

Example 152

8-Cycloheptyl-2-methanesulfinyl-8H-pyrido[2,3-d]pyrimidin-7-one, mp 183–184° C.

Example 153

8-Cyclohexyl-2-cyclohexylamino-8H-pyrido[2,3-d]pyrimidin-7-one, mp 169–170° C.

Example 154

2-[4-(2-Diethylamino-ethoxy)-phenylamino]-8-[3-(tetrahydro-pyran-2-yloxy)-propyl-]-8H-pyrido[2,3-d]pyrimidin-7-one, mp 102–104° C.

Example 155

8-Cycloheptyl-2-phenylamino-8H-pyrido[2,3-d]pyrimidin-7-one, mp 156–158° C.

Example 156

8-Cycloheptyl-2-[4-(2-diethylamino-ethoxy)-phenylamino]-8H-pyrido[2,3-d]pyrimidin-7-one, mp 121–122° C.

Example 157

8-Cyclopentyl-2-(4-piperidin-1-yl-phenylamino)-8H-pyrido[2,3-d]pyrimidin-7-one, mp 198–199° C.

Example 158

2-(4-Piperidin-1-yl-phenylamino)-8-[3-(tetrahydro-pyran-2-yloxy)-propyl]-8H-pyrido[2,3-d]pyrimidin-7-one, mp 85–86° C.

Example 159

8-Cyclohexyl-2-[4-(4-methyl-piperidin-1-yl)-phenylamino]-8H-pyrido[2,3-d]pyrimidin-7-one, mp 208–209° C.

Example 160

8-Cyclohexyl-2-(4-pyrrolidin-1-yl-phenylamino)-8H-pyrido[2,3-d]pyrimidin-7-one, mp 199–200° C.

Example 161

8-Cyclohexyl-2-(4-pyrrole-1-yl-phenylamino)-8H-pyrido[2,3-d]pyrimidin-7-one, mp 183–184° C.

Example 162

8-Cyclohexyl-2-(4-pyrazol-1-yl-phenylamino)-8H-pyrido[2,3-d]pyrimidin-7-one, mp 241–242° C.

Example 163

8-Cycloheptyl-2-(4-piperidin-1-yl-phenylamino)-8H-pyrido[2,3-d]pyrimidin-7-one, mp 201–202° C.

Example 164

1-[4-(8-Cyclohexyl-7-oxo-7,8-dihydro-pyrido[2,3-d]pyrimidin-2-ylamino)-phenyl]-piperidine-4-carboxylic acid ethyl ester, mp 174–175° C.

Example 165

8-Cyclohexyl-2-(2-piperidin-1-yl-ethylamino)-8H-pyrido[2,3-d]pyrimidin-7-one, mp 156–157° C.

Example 166

8-Cyclohexyl-2-(3-piperidin-1-yl-propylamino)-8H-pyrido[2,3-d]pyrimidin-7-one, mp 111–112° C.

Example 167

8Cyclohexyl-2-[4-(3,5-dimethyl-piperidin-1-yl)-phenylamino]-8H-pyrido[2,3-d]pyrimidin-7-one, mp 238–240° C.

Example 168

1-(4-Nitro-phenyl)-pyrrolidine-2-carboxylic acid tert-butyl ester (S), mp 103–104° C.

Example 169

1-(4-Amino-phenyl)-pyrrolidine-2-carboxylic acid tert-butyl ester (S), mp 75–76° C.

Example 170

1-[4(8-Cyclohexyl-7-oxo-7,8-dihydro-pyrido[2,3-d]pyrimidin-2-ylamino)-phenyl]-pyrrolidine-2-carboxylic acid tert-butyl ester, mp 144–145° C.

Example 171

8-Cyclohexyl-2-[4-(3,4-dihydro-1H-isoquinolin-2-yl)-phenylamino]-8H-pyrido[2,3-d]pyrimidin-7-one, mp 185° C.

Example 172

[1-(4-Nitro-phenyl)-piperidin-3-yl]-methanol (racemic), mp 99–100° C.

Example 173

[1-(4-Amino-phenyl)-piperidin-3-yl]-methanol (racemic), mp 108–110° C.

Example 174

[4-(Bicyclo[2.2.1]hept-2-ylamino)-2-methylsulfanyl-pyrimidin-5-yl]-methanol (exo), mp 117–118° C.

Example 175

8-Cyclohexyl-2-[4-(3methyl-piperidin-1-yl)-phenylamino]-8H-pyrido[2,3-d]pyrimidin-7-one, mp 189–190° C.

Example 176

8-Bicyclo[2.2.1]hept-2-yl-2-methylsulfanyl-8H-pyrido[2,3-d]pyrimidin-7-one (exo), mp 102–103° C.

Example 177

8-Cyclohexyl-2-(4thiomorpholin-4-yl-phenylamino)-8H-pyrido[2,3-d]pyrimidin-7-one, mp 213–214° C.

Example 178

8-Bicyclo[2.2.1]hept-2-yl-2-methanesulfinyl-8H-pyrido[2,3-d]pyrimidin-7-one, mp 167–168° C.

Example 179

8-Cyclohexylmethyl-2-methanesulfinyl-8H-pyrido[2,3-d]pyrimidin-7-one, mp 164–165° C.

Example 180

8-Bicyclo[2.2.1]hept-2-yl-2-phenylamino-8H-pyrido[2,3-d]pyrimidin-7-one (exo), mp 225–226° C.

Example 181

8-Bicyclo[2.2.1]hept-2-yl-2-(4-piperidin-1-yl-phenylamino)-8H-pyrido[2,3-d]pyrimidin-7-one (exo), mp 243–244° C.

Example 182

8-Cyclohexylmethyl-2-phenylamino-8H-pyrido[2,3-d]pyrimidin-7-one, mp 230–231° C.

Example 183

8-Cyclohexylmethyl-2-(4-piperidin-1-yl-phenylamino)-8H-pyrido[2,3-d]pyrimidin-7-one, mp 212–213° C.

Example 184

8-Cycloheptyl-2-(4-fluoro-phenylamino)-8H-pyrido[2,3-d]pyrimidin-7-one, mp 198–199° C.

Example 185

8-Cyclohexyl-2-[4-(3-hydroxymethyl-piperidin-1-yl)-phenylamino]-8H-pyrido[2,3-d]pyrimidin-7-one, mp 194–195° C.

Example 186

2-[1-(4-Nitro-phenyl)-piperidin-4-yl]-ethanol, mp 60–61° C.

Example 187

3-[1-(4-Nitro-phenyl)-piperidin-4-yl]-propan-1-ol, mp 166–167° C.

Example 188

2-[1-(4-Amino-phenyl)-piperidin-4-yl]-ethanol, mp 121–122° C.

Example 189

3-[1-(4-Amino-phenyl)-piperidin-4-yl]-propan-1-ol, mp 98–99° C.

Example 190

8-Cyclopentyl-2-(4-pyrrol-1-yl-phenylamino)-8H-pyrido[2,3-d]pyrimidin-7-one, mp 189–190° C.

Example 191

8-Cyclopentyl-2-(4-pyrazol-1-yl-phenylamino)-8H-pyrido[2,3-d]pyrimidin-7-one, mp 197–198° C.

Example 192

[1-(4-Nitro-phenyl)-piperidin-2-yl]-methanol, mp 68–69° C.

Example 193

1-(4-Nitro-phenyl)-piperidin-4-ol, mp 99–100° C.

Example 194

1-(4-Amino-phenyl)-piperidin-4-ol, mp 168–169° C.

Example 195

8-Cyclopentyl-2-[4-(3,5-dimethyl-pyrazol-1-yl)-phenylamino]-8H-pyrido[2,3-d]pyrimidin-7-one, mp 169–171° C.

Example 196

8-Cyclopentyl-2-{4-[4-(2-hydroxy-ethyl)-piperidin-1-yl]-phenylamino}-8H-pyrido[2,3-d]pyrimidin-7-one, mp 199–200° C.

Example 197

8-Cyclopentyl-2-{4-[4-(3-hydroxy-propyl)-piperidin-1-yl]-phenylamino}-8H-pyrido[2,3-d]pyrimidin-7-one, mp 208–209° C.

Example 198

8Cyclopentyl-2-[4-(4-hydroxy-piperidin-1-yl)phenylamino]-8H-pyrido[2,3-d]pyrimidin-7-one, mp 216–217° C.

Example 199

[1-(4-Amino-phenyl)-piperidin-2-yl]-methanol, mp 91–92° C.

Example 200

2-(4-Piperidin-1-yl-phenylamino)-8-(tetrohydro-furan-3-yl)-8H-pyrido[2,3-d]pyrimidin-7-one (racemic), mp 181–182° C.

Example 201

8-Cycloheptyl-2-(3-piperidin-1-yl-phenylamino)-8H-pyrido[2,3-d]pyrimidin-7-one, mp 123–124° C.

Example 202

8-Cyclopentyl-2-(3-piperidin-1-yl-phenylamino)-8H-pyrido[2,3-d]pyrimidin-7-one, mp 90–91° C.

Example 203

8-Cyclohexyl-2-(3-piperidin-1-yl-phenylamino)-8H-pyrido[2,3-d]pyrimidin-7-one, mp 164–165° C.

Example 204

1-(4-Nitro-phenyl)-piperidin-3-ol, mp 112–113 C.

Example 205

1-(4-Amino-phenyl)-piperidin-3-ol, mp 101–102 C.

Example 206

8-Cyclopentyl-2-[4-(3-hydroxy-piperidin-1-yl)-phenylamino]-8H-pyrido[2,3-d]pyrimidin-7-one, mp 178–179° C.

Example 207

8-Cyclopentyl-2-[4-(2-hydroxymethyl-piperidin-1-yl)-phenylamino]-8H-pyrido[2,3-d]pyrimidin-7-one, mp 135–136° C.

Example 208

Dimethyl-[1-(4-nitro-phenyl)-piperidin-4-yl]-amine, mp 102–103° C.

Example 209

1'-(4-Nitro-phenyl)-[1,4']bipiperidinyl, mp 90–91° C.

Example 210

[1-(4-Amino-phenyl)-piperidin-4-yl]-dimethyl-amine, mp 126–127° C.

Example 211

2-(4-Piperidin-1-yl-phenylamino)-8-(tetrahydro-pyran-4-yl)-8H-pyrido[2,3-d]pyrimidin-7-one, mp 254–255° C.

Example 212

8-Bicyclo[2.2.1]hept-2-yl-2-(4-fluoro-phenylamino)-8H-pyrido[2,3-d]pyrimidin-7-one (exo), mp 219–220° C.

Example 213

8-Bicyclo[2.2.1]hept-2-yl-2-[3-(1,1,2,2-tetrafluoro-ethoxy)-phenylamino]-8H-pyrido[2,3-d]pyrimidin-7-one (exo), mp 192° C.

Example 214

8-Bicyclo[2.2.1]hept-2-yl-2-{4-[4-(3-hydroxy-propyl)-piperidin-1-yl]-phenylamino}-8H-pyrido[2,3-d]pyrimidin-7-one (exo), mp 223° C.

Example 215

8-Cyclohexyl-2-[4-(4-hydroxy-piperidin-1-yl)-phenylamino]-8H-pyrido[2,3-d]pyrimidin-7-one, mp 224–225° C.

Example 216

8-Cyclohexyl-2-{4-[4-(2-hydroxy-ethyl)-piperidin-1-yl]-phenylamino}-8H-pyrido[2,3-d]pyrimidin-7-one, mp 236–237° C.

Example 217

8-Bicyclo[2.2.1]hept-2-yl-2-[4-[4-(3-morpholin-4yl-propyl)-piperidin-1-yl]-phenylamino]-8H-pyrido[2,3-d]pyrimidin-7-one (exo), mp 185–186° C.

Example 218

8-Bicyclo[2.2.1]hept-2-yl-2-[4-pyrazol-1-yl-phenylamino)-8H-pyrido[2,3-d]pyrimidin-7-one (exo), mp 234–235° C.

Example 219

8-Bicyclo[2.2.1]hept-2-yl-2-[4-(1,1,2,2-tetrafluoro-ethoxy)-phenylamino]-8H-pyrido[2,3-d]pyrimidin-7-one (exo), mp 214–215° C.

Example 220

8-Bicyclo[2.2.1]hept-2-yl-2-(3,4-difluoro-phenylamino)-8H-pyrido[2,3-d]pyrimidin-7-one (exo), mp 227–228° C.

Example 221

8-Bicyclo[2.2.1]hept-2-yl-2-(4-trifluoromethylsulfanyl-phenylamino)-8H-pyrido[2,3-d]pyrimidin-7-one (exo), mp 205–206° C.

Example 222

2-Benzylamino-8-cyclohexyl-8H-pyrido[2,3-d]pyrimidin-7-one, mp 183–184° C.

Example 223

8-Bicyclo[2.2.1]hept-2-yl-2-(biphenyl-4-ylamino)-8H-pyrido[2,3-d]pyrimidin-7-one (exo), mp 255–257° C.

Example 224

8-Bicyclo[2.2.1]hept-2-yl-2-[4-(2-diethylamino-ethoxy)phenylamino]-8H-pyrido[2,3-d]pyrimidin-7-one, mp 133–134° C.

Example 225

8-Cyclohexyl-2-(4-methoxy-benzylamino)-8H-pyrido[2,3-d]pyrimidin-7-one, mp 165° C.

Example 226

2-Amino-8-cyclohexyl-8H-pyrido[2,3-d]pyrimidin-7-one, mp 155° C.

Example 227

8-Bicyclo[2.2.1]hept-2-yl-2-[4-(4-hydroxy-piperidin-1-yl)-phenylamino]-8H-pyrido[2,3-d]pyrimidin-7-one (exo), mp 206° C.

Example 228

8-Bicyclo[2.2.1]hept-2-yl-2-{4-[4-(2-hydroxy-ethyl)-piperidin-1-yl]-phenylamino}-8H-pyrido[2,3-d]pyrimidin-7-one (exo), mp 202° C.

Example 229 184825 (57958×123)

8-Bicyclo[2.2.1]hept-2-yl-2-(4-piperidin-1-yl-phenylamino)-8H-pyrido[2,3-d]pyrimidin-7-one (endo), mp 209° C.

Example 230

8-Bicyclo[2.2.1]hept-2-yl-2-{4-[4-(3-dimethylamino-propyl)-piperazin-1-yl]-phenylamino}-8H-pyrido[2,3-d]pyrimidin-7-one (exo), mp 212–213° C.

Example 231

8-Bicyclo[2.2.1]hept-2-yl-2-[4-(3-hydroxymethyl-piperidin-1-yl)-phenylamino]-8H-pyrido[2,3-d]pyrimidin-7-one (exo), mp 152° C.

Example 232

2-Methylsulfonyl-8-[3-(tetrahydro-pyran-2-yloxy)propyl]-8H-pyrido[2,3-d]pyrimidin-7-one, mp 65–67° C.

Example 233

2-Methylsulfinyl-8-[3-(tetrahydro-pyran-2H-yloxy)-propyl]-8H-pyrido[2,3-d]pyrimidin-7-one, mp 121–122° C.

Example 234

8-(3-Benzyloxy-propyl)-2-(4-piperidin-1-yl)-phenylamino)-8H-pyrido[2,3-d]pyrimidin-7-one, mp 148–150° C.

Example 235

8-Bicyclo[2.2.1]hept-2-yl-2-{4-[4-(3-morpholin-4-yl-propyl)-piperidin-1-yl]-phenylamino}-8H-pyrido[2,3-d]pyrimidin-7-one, mp 197–198° C.

Example 236

8-Bicyclo[2.2.1]hept-2-yl-2-{4-[3-(3-hydroxy-propy)-piperidin-1-yl]-phenylamino}-8H-pyrido[2,3-d]pyrimidin-7-one, mp 150–151° C.

Example 237

8-Bicyclo[2.2.1]hept-2-yl-2-[4-(3-diethylamino-2-hydroxy-propoxy)-phenylamino]-8H-pyrido[2,3-d]pyrimidin-7-one, oil.

Example 238

3-{4-[2-(tert-Butyl-dimethyl-silanyloxy)-cyclopentylamino]-2-methylsulfanyl-pyrimidin-5-yl}-acrylic acid ethyl ester, MS (CI) m/z 438 (M$^+$).

Example 239

8-[2-(tert-Butyl-dimethyl-silanyloxy)-cyclopentyl]-2-methylsulfanyl-8H-pyrido[2,3-d]pyrimidin-7-one, MS (CI) m/z 392 (M+1).

Example 240

8-[2-(tert-Butyl-dimethyl-silanyloxy)-cyclopentyl]-2-methylsulfinyl-8H-pyrido[2,3-d]pyrimidin-7-one, mp 119–122° C.

Example 241

8-[2-(tert-Butyl-dimethyl-silanyloxy)-cyclopentyl]-2-(4-piperidin-1-yl-phenylamino)-8H-pyrido[2,3-d]pyrimidin-7-one, MS (CI) m/z 520 (M+1).

Example 242

8-(2-Hydroxy-cyclopentyl)-2-(4-piperidin-1-yl-phenylamino)-8H-pyrido[2,3-d]pyrimidin-7-one, mp 230–232° C.

Example 243

4-[5-(2-Ethoxycarbonyl-vinyl)-2-methylsulfanyl-pyrimidin 4 yl amino]-piperidine-1-carboxylic acid ethyl ester, oil. MS (CI) m/z 395 (M+1).

Example 244

4-(2-Methanesulfanyl-7-oxo-7H-pyrido[2,3-d]pyrimidin-8-yl)-piperidine-1-carboxylic acid ethyl ester, mp 165–167° C.

Example 245

4-(2-Methanesulfinyl-7-oxo-7H-pyrido[2,3-d]pyrimidin-8-yl)-piperidine-1-carboxylic acid ethyl ester, mp 151–154° C. MS (CI) m/z 365 (M+1).

Example 246

4-[7-Oxo-2-(4-piperidin-1-yl-phenylamino)-7H-pyrido[2,3-d]pyrimidin-8-yl]-piperidine-1-carboxylic acid ethyl ester, mp 231–233° C.

Example 247

8-(3-Hydroxy-propyl)-2-(4-piperidin-1-yl-phenylamino)-8H-pyrido[2,3-d]pyrimidin-7-one hydrochloride salt, mp discolors at 90° C., >250° C.

Example 248

2-(3-Bromo-2,2-dimethyl-propoxy)-tetrahydro-pyran, oil.

Example 249

2-Methylsulfanyl-8-[2,2-dimethyl-3-(tetrahydro-pyran-2-yloxy)propyl]-8H-pyrido[2,3-d]pyrimidin-7-one, oil. MS (CI) m/z 364 (M+1).

Example 250

2-Methylsulfinyl-8-[2,2-dimethyl-3-(tetrahydro-pyran-2-yloxy)propyl]-8H-pyrido[2,3-d]pyrimidin-7-one, oil.

Example 251

8-(2,2-Dimethyl-2-(tetrahydro-pyran-2-yloxy)propyl]-2-(4-piperidin-1-yl-phenylamino)-8H-pyrido[2,3-d]pyrimidin-7-one, oil.

Example 252

8-(Bicyclo[2.2.1]hept-2-yl-2-[4-(4-methyl-piperazin-1-yl)-phenylamino]-8H-pyrido[2,3-d]pyrimidin-7-one (exo), mp 233–234° C.

Example 253

8-(Bicyclo[2.2.1]hept-2-yl-2-[4-(2-hydroxymethyl-piperidin-1-yl)-phenylamino]-8H-pyrido[2,3-d]pyrimidin-7-one (exo), mp 160–161° C.

Example 254

8-(Bicyclo[2.2.1]hept-2-yl-2-[4-(3-hydroxy-piperidin-1-yl)-phenylamino]-8H-pyrido[2,3-d]pyrimidin-7-one, mp 218° C.

Example 255

8-(Bicyclo[2.2.1]hept-2-yl-2-[4-(3,5-dimethyl-piperazin-1-yl)-phenylamino]-8H-pyrido[2,3-d]pyrimidin-7-one, mp 245–246° C.

Example 256

2-(3,4-Dimethoxy-benzylamino)-8-isopropyl-8H-pyrido[2,3-d]pyrimidin-7-one, mp 128° C.

Example 257

2-Amino-8-isopropyl-8H-pyrido[2,3-d]pyrimidin-7-one, mp 153° C.

Example 258

8-Cyclohexyl-2-{4-[4-(2-morpholin-4yl-ethyl)-piperidin-1-yl]-phenylamino}-8H-pyrido[2,3-d]pyrimidin-7-one, mp 245–246° C.

Example 259

8-Bicyclo[2.2.1]hept-2-yl-2-[4-[4-(2-morpholin-4yl-ethyl)-piperidin-1-yl]-phenylamino]-8H-pyrido[2,3-d]pyrimidin-7-one (exo), mp 223–224° C.

Example 260

8-Isopropyl-2-{4-[4-(3-morpholin-4-yl-propyl)-piperidin-1-yl]-phenylamino}-8H-pyrido[2,3-d]pyrimidin-7-one, mp 195–196° C.

Example 261

8-Bicyclo[2.2.1]hept-2-yl-2-[4-(2-hydroxy-3-morpholin-4-yl-propoxy)-phenylamino]-8H-pyrido[2,3-d]pyrimidin-7-one, oil.

Example 262

8-Bicyclo[2.2.1]hept-2-yl-2-{4-[3-(3-morpholin-4-yl-propyl)-piperidin-1-yl]-phenylamino}-8H-pyrido[2,3-d]pyrimidin-7-one, mp 156–157° C.

Example 263

8-Bicyclo[2.2.1]hept-2-yl-2-[4-(3-morpholin-4-ylmethyl-piperidin-1-yl)-phenylamino]-8H-pyrido[2,3-d]pyrimidin-7-one, mp 155–157° C.

Example 264

8-Ethyl-6-methyl-2-{4-[4-(3-morpholin-4-yl-propyl)-piperidin-1-yl]-phenylamino}-8H-pyrido[2,3-d]pyrimidin-7-one, mp 199–200° C.

Example 265

8-Bicyclo[2.2.1]hept-2-yl-2-(4-piperidin-1-yl-phenylamino)-8H-pyrido[2,3-]pyrimidin-7-one, oil.

Example 266

8-Cyclohexyl-6-methyl-2-{4-[4-(3-morpholin-4-yl-propyl)-piperidin-1-yl]-phenylamino}-8H-pyrido[2,3-d]pyrimidin-7-one

Example 267

6-Amino-8-cyclohexyl-2-{4-[4-(3-morpholin-4-yl-propyl)-piperidin-1-yl]-phenylamino}-8H-pyrido[2,3-d]pyrimidin-7-one

Example 268

4-Amino-8-cyclohexyl-2-{4-[4-(3-morpholin-4-yl-propyl)-piperidin-1-yl]-phenylamino}-8H-pyrido[2,3-d]pyrimidin-7-one

Example 269

5-Amino-8-cyclohexyl-2-{4-[4-(3-morpholin-4-yl-propyl)-piperidin-1-yl]-phenylamino}-8H-pyrido[2,3-d]pyrimidin-7-one

Example 270

8-Cyclohexyl-4-hydroxy-2-{4-[4-(3-morpholin-4-yl-propyl)-piperidin-1-yl]-phenylamino}-8H-pyrido[2,3-d]pyrimidin-7-one

Example 271

8-Cyclohexyl-6-fluoro-2-{4-[4-(3-morpholin-4-yl-propyl)-piperidin-1-yl]-phenylamino}-8H-pyrido[2,3-d]pyrimidin-7-one As noted above, the compounds of this invention are potent inhibitors of cyclin-dependent kinases, and accordingly, are useful in treating and preventing atherosclerosis, and other cell proliferative disorders like cancer. The compounds have exhibited excellent inhibitory activity against a wide variety of cyclin-dependent kinases, all in assay systems routinely utilized to measure such activity. A typical assay, for instance, measures inhibitory activity against the cyclin D dependent kinase 4 enzyme (cdk4/D). The invention compounds of Formulas I and II exhibited $IC_{50}$ values ranging generally from 0.0045 $\mu$M to 10 $\mu$M. The cdk 4 assay was carried out as follows.

Cyclin-Dependent Kinase 4 (cdk4) Assay

Enzyme assays for $IC_{50}$ determinations (Tables 1 and 2) and kinetic evaluation were performed in 96 well filter plates (Millipore MADVN6550). The total volume was 0.1 mL containing a final concentration of 20 mM TRIS (tris[hydroxymethyl]aminomethane), at pH 7.4, 50 mM NaCl, 1 mM dithiothreitol, 10 mM $MgCl_2$, 25 $\mu$M ATP containing 0.25 $\mu$Ci of [$^{32}$P]ATP, 20 ng of cdk4, 1 $\mu$g of retinoblastoma, and appropriate dilutions of a compound of the present invention. All components except the ATP were added to the wells, and the plate was placed on a plate mixer for 2 minutes. The reaction was started by adding [$^{32}$P]ATP and the plate was incubated at 25° C. for 15 minutes. The reaction was terminated by addition of 0.1 mL of 20% trichloroacetic acid (TCA). The plate was kept at 4° C. for at least 1 hour to allow the substrate to precipitate. The wells were then washed five times with 0.2 mL of 10% TCA and $^{32}$P incorporation was determined with a beta plate counter (Wallac Inc., Gaithersburg, Md.).

Cyclin-Dependent Kinase Assays (cdk2/cyclinE, cdk2/cyclinA, cdc2/cyclinB)

Enzyme assays for $IC_{50}$ determinations and kinetic evaluation were performed in a 96-well filter plate (Millipore MADVN6550) in a total volume of 0.1 mL of 20 mM TRIS (tris[hydroxymethyl]aminomethane), at pH 7.4, 50 mM NaCl, 1 mM dithiothreitol, 10 mM $MgCl_2$, 12 mM ATP containing 0.25 $\mu$Ci of [$^{32}$P]ATP, 20 ng of enzyme (either cdk2/cyclinE, cdk2/A, or cdc2/cyclinB), 1 $\mu$g retinoblastoma, and appropriate dilutions of the particular invention compound. All components except the ATP were added to the wells, and the plate was placed on a plate mixer for 2 minutes. The reaction was begun by addition of [$^{32}$P]ATP, and the plate was incubated at 25° C. for 15 minutes. The reaction was terminated by addition of 0.1 mL of 20% TCA. The plate was kept at 4° C. for at least 1 hour to allow the substrate to precipitate. The wells were then washed five times with 0.2 mL of 10% TCA and $^{32}$P incorporation determined with a beta plate counter (Wallac Inc., Gaithersburg, Md.).

When measured against cdk2/E, the invention compounds exhibited $IC_{50}$ values ranging generally from about 0.02 to about 25 $\mu$M. Against cdk2/A, the compounds exhibited $IC_{50}$ values ranging from about 0.01 to about 14 $\mu$M, and against cdk2/B, generally from about 0.06 to about 40 $\mu$M. The assays were carried out as described above, and specific data is given in Table 1.

TABLE 1

[Structure: 2-(R¹NH)-8-(R²)-pyrido[2,3-d]pyrimidin-7(8H)-one]

| Example | R¹ | R² | cdk4/D | cdk2/E | cdk2/A IC$_{50}$μM | cdk1/B |
|---|---|---|---|---|---|---|
| 18 | Ph | Et | 0.752 | 0.41 | 0.129 | 1.015 |
| 32 | Ph | H | — | 12.83 | 4.66 | 32.6 |
| 36 | Ph | CH$_2$COOMe | 31 | | | |
| 37 | Ph | CH$_2$OMe | 4.2 | | | |
| 38 | Ph | (CH$_2$)$_3$—OCH$_2$Ph | 2.695 | 1.75 | 13.54 | 29.8 |
| 39 | Ph | CH$_2$-epoxide | 5.0 | | | |
| 40 | Ph | n-Bu | 1.495 | 0.058 | 0.037 | 0.205 |
| 41 | Ph | n-Pr | 0.55 | 0.112 | 0.05 | 0.299 |
| 42 | Ph | CH$_2$CHMe$_2$ | 0.40 | | | |
| 43 | Ph | CHMe$_2$ | 0.15 | 0.126 | 0.031 | 0.44 |
| 44 | CH$_2$Ph | Et | | | 6.46 | 16.65 |
| 45 | Et | Et | 12 | 3.93 | 2.46 | 9.23 |
| 46 | t-Bu | Et | 5.3 | | | 3.41 |
| 47 | i-Pr | Et | 3.7 | | | 3.55 |
| 48 | cyclohex | Et | 3.3 | 0.592 | 0.23 | 2.61 |
| 49 | Ph-4-Ph | Et | 2.0 | | | |
| 50 | 4-pyr | Et | 2.0 | | | |
| 51 | Ph-4-OMe | Et | 0.60 | 0.422 | 0.134 | 0.665 |
| 52 | Ph-4-O(CH$_2$)$_2$NEt$_2$ | Et | 0.16 | 2.34 | 0.75 | 2.66 |
| 53 | Ph-4-pip-4-Me | Et | 0.085 | 1.19 | 0.339 | 1.88 |
| 54 | Ph-3-OCF$_2$CF$_2$H | Et | 7.83 | 1.2 | 0.238 | 0.091 |
| 55 | Ph-4-OH | Et | 0.6 | | | |
| 56 | Ph-4-OCH$_2$Ph | Et | 25 | | | |
| 57 | Ph-4-O(CH$_2$)$_2$OMe | Et | 0.8 | | | |
| 58 | Ph | CH$_2$Ph-4-OMe | 10 | | | |
| 59 | Ph-4-O(CH$_2$)$_2$NEt$_2$ | CHMe$_2$ | 0.045 | 0.8 | 0.08 | 1.24 |
| 60 | Ph-4-pip-4-Me | CHMe$_2$ | 0.032 | 0.27 | 0.058 | 0.675 |
| 61 | Ph | Me | 6.9 | 0.86 | 0.49 | 1.76 |
| 63 | CH$_2$Ph | Me | | | 38.12 | 21.6 |
| 64 | n-Bu | Me | 40 | | | |
| 66 | (CH$_2$)$_2$-2-pyridine | Me | 45 | | | |
| 67 | i-Pr | Me | 25 | | | |
| 69[a] | Ph | Et | 4.3 | | | |
| 74 | Ph | CHEt$_2$ | 0.141 | | | |
| 77 | Ph-4-pip-4-Me | CHEt$_2$ | 0.014 | 0.068 | 0.028 | 0.141 |
| 78 | Ph-4-Net$_2$ | Et | 1.3 | 2.94 | 2.24 | 0.74 |
| 79 | Ph-4-morpholine | Et | 0.3 | | | |
| 83 | NHPh | Et(6-Me) | 1.8 | | | |
| 84 | Ph-4-pip-4-Me | Et(6-Me) | 0.18 | | | |
| 85 | Ph | CHMeEt | 0.2 | | | |
| 86 | Ph | CH$_2$CH$_2$O—Me | 2.4 | | | |
| 87 | Ph | (CH$_2$)$_3$OCH$_2$—Ph | | | 5.9 | 1.08 |
| 88 | Ph-4-F | Et | 1.3 | 0.28 | 0.44 | 2.07 |
| 89 | Ph-3-F | Et | 1.4 | | | |
| 90 | Ph-3-F-4-OMe | Et | 1.0 | | | |
| 91 | Ph-3-F-2-OMe | Et | 9.0 | | | |
| 93 | Ph-4-NMe$_2$ | Et | 0.38 | 1.77 | 0.28 | 0.78 |
| 100 | Et | Ph | 19.05 | | | |
| 101 | Ph | Ph | 1.7 | | | |
| 108 | Ph | cyclopentyl | 0.21 | 0.11 | 0.012 | 0.19 |
| 131 | Ph | cyclohexyl | 0.047 | 0.125 | 0.079 | 0.749 |
| 147 | Ph-4-NMe$_2$ | cyclohexyl | 0.48 | 0.081 | 0.012 | 0.089 |
| 155 | Ph | cycloheptyl | 0.182 | 0.024 | 0.009 | 0.065 |
| 180 | Ph | norbornane | 0.038 | 0.173 | 0.075 | 0.503 |
| 200 | Ph-4-(piperidin-1-yl) | tetrahydrofuryl | 0.219 | 1.9 | 0.285 | 4.34 |

[a] Single bond between C$^5$ and C$^6$

TABLE 2

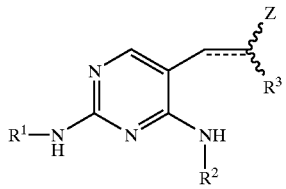

| Example | $R_1$ | $R_2$ | $R_3$ | Bond | Z | cdk4/$IC_{50}$ $IC_{50}$ μM | cdk4/D % inhibition at 40 μM |
|---|---|---|---|---|---|---|---|
| 17 | Ph | Et | H | trans double | COOEt | 2 | |
| 68 | Ph | Et | H | single | COOEt | 90 | 37% |
| 28 | Ph | H | H | trans double | COOEt | 65 | |
| 73 | Ph | Et | Me | trans double | COOEt | | 58% |
| 72 | Ph | Et | H | trans double | CN | | 18% |

Several of the invention compounds have also shown good inhibitory activity against cdk6/$D_2$ and cdk6/$D_3$ enzymes. These assays are carried out in a manner similar to that described above for cdk4, by simply employing the appropriate cdk6 kinase enzyme. Invention compounds have shown $IC_{50}$ values rangeing from about 0.009 μM to about 0.2 μM. The compound of Example 214, for instance, had an $IC_{50}$ of 0.0071 μM against cdk6/$D_2$, and an $IC_{50}$ of 0.013 μM against cdk6/$D_3$.

The compounds of Formulas I and II also have shown good inhibitory activity against certain growth factor receptor tyrosine kinase enzymes, including fibroblast growth factor (FGF) and platelet derived growth factor (PDGF). The compounds exhibit only marginal activity against epidermal growth factor (EGF) receptor tyrosine kinase. The invention compounds range in $IC_{50}$ inhibition against FGF tyrosine kinase generally from about 0.004 to about 40 μM. Against PDGF tyrosine kinase, the invention compounds exhibit $IC_{50}$ from about 0.05 to about 40 μM. The assays used to determine these activities were carried out as follows:

Purification of Epidermal Growth Factor Receptor Tyrosine Kinase

Human EGF receptor tyrosine kinase was isolated from A431 epidermoid carcinoma cells by the following method. Cells were grown in roller bottles in 50% Dulbecco's Modified Eagle medium and 50% HAM F-12 nutrient media (Gibco) containing 10% fetal calf serum. Approximately $10^9$ cells were lysed in two volumes of buffer containing 20 mM 2-(4N-[2-hydroxymethyl]-piperazin-1-yl)ethanesulfonic acid, pH 7.4, 5 mM ethylene glycol bis(2-aminoethyl ether) N,N,N',N'-tetraacetic acid, 1% Triton X-100, 10% glycerol, 0.1 mM sodium orthovanadate, 5 mM sodium fluoride, 4 mM pyrophosphate, 4 mM benzamide, 1 mM dithiothrietol, 80 μg/mL aprotinin, 40 μg/mL leupeptin, and 1 mM phenylmethylsulfonylfluoride (PMSF). After centrifugation at 25,000×g for 10 minutes, the supernatant was equilibrated for 2 hours at 4 μC with 10 mL of wheat germ agglutinin sepharose that was previously equilibrated with 50 mM Hepes, 10% glycerol, 0.1% Triton x-100 and 150 mM NaCl, pH 7.5 (equilibration buffer). Contaminating proteins were washed from the resin with 1 M NaCl in equilibration buffer, and the enzyme was eluted with 0.5 M N-acetyl-1-D-glucosamine in equilibration buffer.

PDGF and EGF Receptor Tyrosine Kinase Assays

Full-length cDNAs for the mouse PDGF-β and human FGF-1 (flg) receptor tyrosine kinases were obtained from J. Escobedo and prepared as described in *J. Biol. Chem.*, 1991;262:1482–1487. PCR primers were designed to amplify a fragment of DNA that codes for the intracellular tyrosine kinase domain. The fragment was inserted into a baculovirus vector, cotransfected with AcMNPV DNA, and the recombinant virus isolated. SF9 insect cells were infected with the virus to overexpress the protein, and the cell lysate was used for the assay. Assays were performed in 96-well plates (100 μL/incubation/well), and conditions were optimized to measure the incorporation of $^{32}P$ from $\gamma^{32}P$-ATP into a glutamate-tyrosine co-polymer substrate. Briefly, to each well was added 82.5 μL of incubation buffer containing 25 mM Hepes (pH 7.0), 150 mM NaCl, 0.1% Triton X-100, 0.2 mM PMSF, 0.2 mM $Na_3VO_4$, 10 mM $MnCl_2$, and 750 μg/mL of Poly (4:1) glutamate-tyrosine followed by 2.5 μL of inhibitor and 5 μL of enzyme lysate (7.5 μg/μL FGF-TK or 6.0 μg/μL PDGF-TK) to initiate the reaction. Following a 10 minute incubation at 25° C., 10 mL of $\gamma^{32}P$-ATP (0.4 μCi plus 50 μM ATP) was added to each well, and samples were incubated for an additional 10 minutes at 25° C. The reaction was terminated by the addition of 100 μL of 30% trichloroacetic acid (TCA) containing 20 mM sodium pyrophosphate and precipitation of material onto glass fiber mats (Wallac). Filters were washed three times with 15% TCA containing 100 mM sodium pyrophosphate, and the radioactivity retained on the filters counted in a Wallac 1250 Betaplate reader. Nonspecific activity was defined as radioactivity retained on the filters following incubation of samples with buffer alone (no enzyme). Specific enzymatic activity (enzyme plus buffer) was defined as total activity minus nonspecific activity. The concentration of a compound that inhibited specific activity by 50% ($IC_{50}$) was determined based on the inhibition curve, and typical results are reported in Tables 3 and 4.

TABLE 3

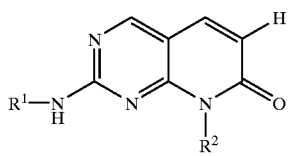

| Example | $R^1$ | $R^2$ | PDGF $IC_{50}$ μM | FGF $IC_{50}$ μM |
|---|---|---|---|---|
| 18 | Ph | Et | 1.78 | 3.3 |
| 41 | Ph | n-Pr | 4.96 | 6.6 |
| 42 | Ph | i-Bu | 3.69 | 4.06 |

TABLE 3-continued

| Example | R¹ | R² | PDGF IC$_{50}$ μM | FGF IC$_{50}$ μM |
|---|---|---|---|---|
| 108 | Ph | cyclopentyl | 4.18 | 2.98 |
| 131 | Ph | cyclohexyl | 16.1 | 12.4 |
| 150 | Ph-3-Me-4(O—CH$_2$CH$_2$NEt$_2$) | cyclohexyl | 0.099 | 0.099 |
| 162 | Ph-4-(pyrazol-1-yl) | cyclohexyl | 17.1 | 19.7 |
| 167 | Ph-4-(3,5-diMe-piperidin-1-yl) | cyclohexyl | 33.1 | 20.6 |
| 180 | Ph | norbornane | 27.8 | 12 |
| 196 | Ph-4-[4-(HOCH$_2$CH$_2$-)-piperidin-1-yl] | cyclopentyl | 1.06 | 1.45 |

TABLE 4

| Example | R¹ | R² | R³ | Z | Bond | PDGF | FGF IC$_{50}$ μM |
|---|---|---|---|---|---|---|---|
| 17 | Ph | Et | H | COOEt | trans double | 3.7 | 4.5 |

The Src family of protein kinases, which all contain a SH2 domain, are involved in a number of cellular signaling pathways. For example, Src is involved in growth factor receptor signaling; integrin-mediated signaling; T- and B-cell activation and osteoclast activation. It is known that the Src SH2 domain binds to several key receptor and nonreceptor tyrosine kinases such as tyrosine kinases containing receptors for PDGF, EGF, HER2/Neu (an oncogene form of EGF), FGF, focal adhesion kinase, p130 protein, and p68 protein. In addition, pp60c-Src has been shown to be involved in the regulation of DNA synthesis, mitosis, and other cellular activities.

Thus, it would be useful to have compounds that inhibit the binding of proteins containing an SH2 domain to cognate phosphorylated proteins, as the inhibition of binding of proteins containing an SH2 domain to cognate phosphorylated proteins can be used to treat proliferative diseases such as cancer, osteoporosis, inflammation, allergy, restenosis, and cardiovascular disease, which all rely on signal transduction involving proteins that contain an SH2 domain that binds to phosphorylated proteins during the cellular signaling process.

Several of the invention compounds have been evaluated in a standard assay to measure their ability to inhibit cellular Src protein kinase (c-Src). The invention compounds exhibited IC$_{50}$ values ranging generally from about 0.1 to about 50 μM. The assay was carried out as follows:

C-Src kinase was purified from baculovirus infected insect cell lysates using an antipeptide monoclonal antibody directed against the N-terminal amino acids (amino acids 2–17) of c-Src. The antibody, covalently linked to 0.65 μm latex beads, was added to a suspension of insect cell lysis buffer comprised of 150 mM NaCl, 50 mM Tris pH 7.5, 1 mM DTT, 1% NP-40, 2 mM EGTA, 1 mM sodium vanadate, 1 mM PMSF, 1 μg/mL each of leupeptin, pepstatin, and aprotinin. Insect cell lysate containing c-Src protein was incubated with these beads for 3 to 4 hours at 4° C. with rotation. At the end of the lysate incubation, the beads were rinsed three times in lysis buffer, resuspended in lysis buffer containing 10% glycerol, and frozen. These latex beads were thawed, rinsed three times in assay buffer (40 mM Tris, pH 7.5, 5 mM μgCl$_2$) and suspended in the same buffer. In a Millipore 96-well plate with a 0.65 μm polyvinylidine membrane bottom were added the reaction components: 10 μL c-Src beads, 10 μL of 2.5 mg/mL poly GluTyr substrate, 5 μM ATP containing 0.2 μCi labeled $^{32}$P-ATP, 5 μL DMSO containing inhibitors or as a solvent control, and buffer to make final volume 125 μL. The reaction was started at room temperature by addition of the ATP and quenched 10 minutes later by the addition of 125 μL of 30% TCA, 0.1 M sodium pyrophosphate for 5 minutes on ice. The plate was then filtered and the wells washed with two 250 mL aliquots of 15% TCA, 0.1 M pyrophosphate. The filters were then punched, counted in a liquid scintillation counter, and the data examined for inhibitory activity in comparison to a known inhibitor such as erbstatin. The method is also described in *J. Med. Chem.*, 1994;37:598–609. Table 5 lists c-Src inhibitory concentrations (IC$_{50}$) for representative invention compounds.

TABLE 5

| Example | R¹ | R² | C-Src IC$_{50}$ μM |
|---|---|---|---|
| 40 | Ph | n-Pr | 19.5 |
| 52 | Ph-4-(2-diEtN-EtO) | Et | 1.03 |
| 59 | Ph-4-(2-diEtN-EtO) | i-Pr | 4.43 |
| 50 | pyridin-4-yl | Et | 15 |
| 60 | Ph-4-(4-Me-piperazin-1-yl) | i-Pr | 0.89 |
| 101 | Ph | Ph | 21.25 |
| 115 | Ph-4-(4-Me-piperazin-1-yl) | 3-PhCH$_2$O—Pr | 0.545 |
| 143 | Ph-4-[3,5-diMe-4-(2-OHEt)-piperazin-1-yl] | cyclohexyl | 1.85 |
| 198 | Ph-4-(4-OH-piperidin-1-yl) | cyclopentyl | 1.095 |

The invention compounds additionally have been shown to be bioavailable in animals, reaching peak plasma levels in nude mice in the range of about 10 nM to about 200 nM within 30 minutes following oral dosing at levels of about 4 to 5 mg/kg as suspensions in lactate buffer solutions having pH of 4.0. For example, the compound of Example 60 was administered orally at 5 mg/kg to mice, and plasma levels of about 200 nM were measured at 30 minutes following dosing. The compound was also administered intraperitoneally at 12 mg/kg and produced a peak plasma concentration of 10,000 nM at 30 minutes following dosing. When evaluated in female nude mice bearing subcutaneous MCF-7 human mammary tumor xenografts, the compound of Example 60 showed statistically insignificant tumor growth inhibitions at doses of 5 to 20 mg/kg when dosed on a schedule of q12 h×2; days 1–14.

The invention compounds can be formulated in conventional manners to provide convenient dosage forms for delivery to mammals by various routes, including oral, parenteral (i.e., subcutaneous, intravenous, and intramuscular), transdermal, e.g. slow release skin patch or cream, as well as by slow release delivery devices such as osmotic pumps, suppositories, and buccal seals. The following examples further illustrate how the compounds are readily formulated.

Example 272

| 50 mg Tablet Formulation | | | |
|---|---|---|---|
| Per Tablet | | | Per 10,000 Tablets |
| 0.050 g | 2-benzylamino-8-cyclopropyl-8H-pyrido[2,3-d]pyrimidin-7-one | | 500 g |
| 0.080 g | lactose | | 800 g |
| 0.010 g | corn starch (for mix) | | 100 g |
| 0.008 g | corn starch (for paste) | | 80 g |
| 0.148 g | | | 1480 g |
| 0.002 g | magnesium stearate (1%) | | 20 g |
| 0.150 g | | | 1500 g |

The pyrido pyrimidine, lactose, and corn starch (for mix) are blended to uniformity. The corn starch (for paste) is suspended in 600 mL of water and heated with stirring to form a paste. This paste is used to granulate the mixed powders. The wet granules are passed through a No. 8 hand screen and dried at 80° C. The dry granules are then passed through a No. 16 screen. The mixture is lubricated with 1% magnesium stearate and compressed into tablets in a conventional tableting machine. The tablets are useful for treating cancers such as breast, prostate, lung, ovarian, colon, pancreatic, melanoma, esophageal, brain, Kaposi's sarcoma, and lymphomas.

Example 273

| Preparation of Oral Suspension | |
|---|---|
| Ingredient | Amount |
| 8-Ethyl-2-(4-pyrrol-1-yl-phenylamino)-8H-pyrido[2,3-d]pyrimidin-7-one | 500 mg |
| Sorbitol solution (70% N.F.) | 40 mL |
| Sodium benzoate | 150 mg |

| -continued | |
|---|---|
| Preparation of Oral Suspension | |
| Ingredient | Amount |
| Saccharin | 10 mg |
| Cherry flavor | 50 mg |
| Distilled water qs | 100 mL |

The sorbitol solution is added to 40 mL of distilled water, and the pyrido pyrimidine is suspended therein. The saccharin, sodium benzoate, and flavoring are added and dissolved. The volume is adjusted to 100 mL with distilled water. Each milliliter of syrup contains 5 mg of invention compound.

Example 274

Preparation of Parenteral Solution

In a solution of 700 mL of propylene glycol and 200 mL of water for injection is suspended 20.0 g of 8-bicyclo[2.2.1]hept-2-yl-2-phenylamino-8H-pyrido[2,3-d]pyrimidin-7-one with stirring. After suspension is complete, the pH is adjusted to 5.5 with hydrochloric acid, and the volume is made up to 1000 mL with water for injection. The formulation is sterilized, filled into 5.0 mL ampoules, each containing 2.0 mL (representing 40 mg of invention compound) and sealed under nitrogen.

Example 275

Suppositories

A mixture of 400 mg of 8-(2-hydroxy-cyclopentyl)-2-(4-piperidin-1-yl-phenylamino)-8H-pyrido[2,3-d]pyrimidin-7-one, and 600 mg of theobroma oil is stirred at 60° C. to uniformity. The mixture is cooled and allowed to harden in a tapered mold to provide a 1 g suppository.

Example 276

Slow Release Formulation

Five hundred milligrams of 8-(3-hydroxypropyl)-2-(4-piperidin-1-yl-phenylamino)-8H-pyrido[2,3-d]pyrimidin-7-one is converted to a hydrochloride salt and placed into an Oros osmotic pump for controlled release for treatment of atherosclerosis.

Example 277

Skin Patch Formulation

Fifty milligrams of (8-Bicyclo[2.2.1]hept-2-yl-2-[4-[4-(2-morpholin-4-yl-ethyl)-piperidin-1-yl]-phenylamino]-8H-pyrido[2,3-d]pyrimidin-7-one (exo)) is admixed with 50 mg of propylene glycol monolaurate in a polydimethylsiloxane adhesive. The mixture is layered onto an elastic film made with an adhesive formulation of polybutene, polyisobutylene, and propylene glycol monolaurate. The layers are placed between 2 layers of polyurethane film. A release liner is attached to the adhesive surface, and is removed prior to application to a skin surface. The propylene glycol monolaurate serves as a permeation-enhancing agent.

What is claimed is:
1. A compound of Formula I

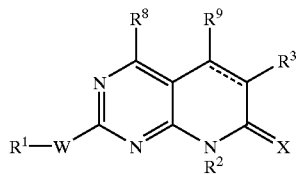

or a pharmaceutically acceptable salt thereof, wherein:
the dotted line represents an optional bond;
W is NH, S, SO, or $SO_2$;
X is O;
$R^1$ is selected from the group consisting of phenyl, $(CH_2)_n$ phenyl, naphthyl, $(CH_2)_n$naphthyl, $(CH_2)_n$ $C_2–C_8$ heteroaryl, $(CH_2)_n$ $C_2–C_6$ heterocyclyl, $C_1–C_{10}$ alkyl, and $C_3–C_{10}$ cycloalkyl, wherein n is 0 or 1 and the phenyl, $(CH_2)_n$heteroaryl, heterocyclyl, alkyl, and cycloalkyl groups are optionally substituted by up to 5 groups selected from $NR^4R^5$, $N(O)R^4R^5$, phenyl, substituted phenyl, hydroxy, $C_1–C_6$ alkyl, $C_1–C_6$ alkoxy, phenoxy, thiol, $C_1–C_6$ thioalkyl, halo, $COR^4$, $CO_2R^4$, $CONR^4R^5$, $SO_2NR^4R^5$, $SO_3R^4$, aldehyde, nitrile, nitro, $C_2–C_6$ heteroaryloxy, $T(CH_2)_mQR^4$, $C(O)T(CH_2)_mQR^4$, $NHC(O)T(CH_2)_mQR^4$, or $T(CH_2)_mCO_2R^4$ wherein m is 1–6, T is O, S, $NR^4$, $N(O)R^4$, or $CR^4R^5$, and Q is O, S, $NR^5$, or $N(O)R^5$;
$R^2$ is selected from the group consisting of $C_1–C_{10}$ alkyl, $C_3–C_{10}$ cycloalkyl, $(CH_2)_n$phenyl, $(CH_2)_n$ $C_2–C_6$ heteroaryl, $(CH_2)_n$ $C_2–C_6$ heterocyclyl, wherein n is 0, 1, or 2 and the phenyl, $(CH_2)_n$heteroaryl, alkyl, and cycloalkyl groups are optionally substituted by up to 5 groups selected from $NR^4R^5$, $C_1–C_6$ alkyl, hydroxy, nitrile, $C_1–C_6$ alkoxy, halo, $CO_2R^4$, and $CONR^4R^5$;
$R^3$ is H, $C_1–C_6$ alkyl, halo, nitro, cyano, $OR^4$, $CO_2R^4$, $CONR^4R^5$, or $NR^4R^5$;
$R^4$ and $R^5$ are independently selected from the group consisting of hydrogen, $C_1–C_6$ alkyl, substituted alkyl, $C_3–C_{10}$ cycloalkyl, $C_2–C_6$ heterocyclyl, and $C_2–C_6$ heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur; optionally substituted with alkyl, $T(CH_2)_mQR^{4'}$, $C(O)T(CH_2)_mQR^{4'}$, $T(CH_2)_mCO_2R^{4'}$, $(CH_2)_mQR^{4'}$, $T(CH_2)_mCONR^{4'}R^{5'}$ wherein m is 1–6, T is O, S, $NR^{4'}$, $N(O)R^{4'}$, or $CR^4R^{5'}$, and Q is O, S, $NR^{5'}$, or $N(O)R^{5'}$;
$R^{4'}$ and $R^{5'}$ are independently selected from the group consisting of hydrogen, $C_1–C_6$ alkyl, substituted alkyl, $C_3–C_{10}$ cycloalkyl, $C_2–C_6$ heterocyclyl, and $C_2–C_6$ heteroaryl;
$R^8$ is H, $C_1–C_3$ alkyl, and halo;
when the bond represented by the dotted line is present, $R^9$ is selected from the group consisting of H, $C_1–C_3$ alkyl, $NR^4R^5$, hydroxy, thiol, or halo; and
when the bond represented by the dotted line is absent, $R^9$ is H, $C_1–C_3$ alkyl, $NR^4R^5$, $N(O)R^4R^5$, hydroxy, $C_1–C_6$alkoxy, thiol, $C_1–C_6$thioalkyl, halo, $COR^4$, $CO_2R^4$, $CONR^4R^5$, $SO_2NR^4R^5$, $SO_3R^4$, CHO, CN, or $NO_2$.

2. A compound of claim 1 wherein W is NH and $R^8$ and $R^9$ both are hydrogen.

3. A compound of claim 2 wherein a double bond exists between $C_5$ and $C_6$.
4. A compound of claim 3 wherein $R^1$ is phenyl or substituted phenyl.
5. A compound of claim 4 wherein $R^2$ is an unsubstituted or substituted alkyl, or cycloalkyl.
6. A compound according to claim 5 selected from:
8-Ethyl-2-phenylamino-8H-pyrido[2,3-d]pyrimidin-7-one;
8-Benzyl-2-phenylamino-8H-pyrido[2,3-d]pyrimidin-7-one;
7-Oxo-2-phenylamino-7H-pyrido[2,3-d]pyrimidin-8-yl)-acetic acid methyl ester;
8-Methoxymethyl-2-phenylamino-8H-pyrido[2,3-d]pyrimidin-7-one;
8-(3-Benzyloxypropyl)-2-phenylamino-8H-pyrido[2,3-d]pyrimidin-7-one;
8-Oxiranylmethyl-2-phenylamino-8H-pyrido[2,3-d]pyrimidin-7-one;
8-Butyl-2-phenylamino-8H-pyrido[2,3-d]pyrimidin-7-one;
2-Phenylamino-8-propyl-8H-pyrido[2,3-d]pyrimidin-7-one;
8-Isobutyl-2-phenylamino-8H-pyrido[2,3-d]pyrimidin-7-one;,
8-Isopropyl-2-phenylamino-8H-pyrido[2,3-d]pyrimidin-7-one;
2-(Biphenyl-4-ylamino)-8-ethyl-8H-pyrido[2,3-d]pyrimidin-7-one;
8-Ethyl-2-(4-methoxyphenylamino)-8H-pyrido[2,3-d]pyrimidin-7-one;
2-[4-(2-Diethylaminoethoxy)-phenylamino]-8-ethyl-8H-pyrido[2,3-d]pyrimidin-7-one;
8-Ethyl-2-[4-(4-methylpiperazin-1-yl)-phenylamino]-8H-pyrido[2,3-d]pyrimidin-7-one;
8-Ethyl-2-[3-(1,1,2,2-tetrafluoroethoxy)-phenylamino]-8H-pyrido[2,3-d]pyrimidin-7-one;
8-Ethyl-2-(4-hydroxyphenylamino)-8H-pyrido[2,3-d]pyrimidin-7-one;
2-Benzyloxyphenylamino-8-ethyl-8H-pyrido[2,3-d]pyrimidin-7-one;
8-Ethyl-2-[4-(2-methoxyethoxy)phenylamino]-8H-pyrido[2,3-d]pyrimidin-7-one;
8-(4-Methoxybenzyl)-2-phenylamino-8H-pyrido[2,3-d]pyrimidin-7-one;
2-[4-(2-Diethylaminoethoxy)-phenylamino]-8-isopropyl-8H-pyrido[2,3-d]pyrimidin-7-one;
8-Isopropyl-2-[4-(4-methylpiperazin-1-yl)-phenylamino]-8H-pyrido[2,3-d]pyrimidin-7-one;
8-Methyl-2-phenylamino-8H-pyrido[2,3-d]pyrimidin-7-one;
8-(1-Ethylpropyl)-2-phenylamino-8H-pyrido[2,3-d]pyrimidin-7-one;
8-(1-Ethylpropyl)-2-[4-(4-methylpiperazin-1-yl)-phenylamino]-8H-pyrido[2,3-d]pyrimidin-7-one;
2-(4-Diethylamino-phenylamino)-8-ethyl-8H-pyrido[2,3-d]pyrimidin-7-one;
8-Ethyl-2-(4-morpholin-4-yl-phenylamino)-8H-pyrido[2,3-d]pyrimidin-7-one;
8-Ethyl-6-methyl-2-phenylamino-8H-pyrido[2,3-d]pyrimidin-7-one;
8-Ethyl-6-methyl-2-[4-(4-methyl-piperazin-1-yl)-phenylamino-8H-pyrido[2,3-d]pyrimidin-7-one;
8-Sec-butyl-2-phenylamino-8H-pyrido[2,3-d]pyrimidin-7-one;
8-(2-Methoxyethyl)-2-phenylamino-8H-pyrido[2,3-d]pyrimidin-7-one;
8-(3-Phenoxypropyl)-2-phenylamino-8H-pyrido[2,3-d]pyrimidin-7-one,
8-Ethyl-2-(4-fluorophenylamino)-8H-pyrido[2,3-d]pyrimidin-7-one;

8-Ethyl-2-(3-fluorophenylamino)-8H-pyrido[2,3-d]pyrimidin-7-one;
8-Ethyl-2-(3-fluoro-4-methoxyphenylamino)-8H-pyrido[2,3-d]pyrimidin-7-one;
8-Ethyl-2-(3-fluoro-2-methoxyphenylamino)-8H-pyrido[2,3-d]pyrimidin-7-one;
8-Ethyl-2-(2-methoxyphenylamino)-8H-pyrido[2,3-d]pyrimidin-7-one;
2-(4-Dimethylamino-phenylamino)-8-ethyl-8H-pyrido[2,3-d]pyrimidin-7-one;
2-(4-Hydroxy-phenylamino)-8-isopropyl-8H-pyrido[2,3-d]pyrimidin-7-one;
8-Isopropyl-2-(4-methoxy-phenylamino)-8H-pyrido[2,3-d]pyrimidin-7-one;
8-Ethyl-2-(4-pyrrol-1-yl-phenylamino)-8H-pyrido[2,3-d]pyrimidin-7-one;
8-(3-Benzyloxy-propyl)-2-[4-(4-methyl-piperazin-1-yl)-phenylamino]-8H-pyrido[2,3-d]pyrimidin-7-one;
8-(3-Benzyloxy-propyl)-2-[4-(2-diethylamino-ethoxy)-phenylamino]-8H-pyrido[2,3-d]pyrimidin-7-one;
8-(3-Benzyloxy-propyl)-2-(4-dimethylamino-phenylamino)-8H-pyrido[2,3-d]pyrimidin-7-one;
8-(2-Benzyloxy-ethyl)-2-[4-(2-diethylamino-ethoxy)-phenylamino]-8H-pyrido[2,3-d]pyrimidin-7-one;
8-Isopropyl-2-[4-(2-morpholin-4-yl-ethoxy)-phenylamino]-8H-pyrido[2,3-d]pyrimidin-7-one;
8-(2-Benzyloxy-ethyl)-2-[4-(4-methyl-piperazin-1-yl)-phenylamino]-8H-pyrido[2,3-d]pyrimidin-7-one;
2-[4-(2-Diethylamino-ethoxy)-phenylamino]-8-[3-(tetrahydro-pyran-2-yloxy)-propyl]-8H-pyrido[2,3-d]pyrimidin-7-one;
2-(4-Piperidin-1-yl-phenylamino)-8-[3-(tetrahydro-pyran-2-yloxy)-propyl]-8H-pyrido[2,3-d]pyrimidin-7-one;
8-Cyclohexylmethyl-2-phenylamino-8H-pyrido[2,3-d]pyrimidin-7-one;
8-Cyclohexylmethyl-2-(4-piperidin-1-yl-phenylamino)-8H-pyrido[2,3-d]pyrimidin-7-one;
8-(3-Benzyloxy-propyl)-2-(4-piperidin-1-yl-phenylamino)-8H-pyrido[2,3-d]pyrimidin-7-one;
8-(3-Hydroxy-propyl)-2-(4-piperidin-1-yl-phenylamino)-8H-pyrido[2,3-d]pyrimidin-7-one dihydrochloride;
8-(2,2-Dimethyl-2-(tetrahydro-pyran-2-yloxy)propyl]-2-(4-piperidin-1-yl-phenylamino)-8H-pyrido[2,3-d]pyrimidin-7-one;
8-Ethyl-2-[4-(pyridin-3-yloxy)-phenylamino]-8H-pyrido[2,3-d]pyrimidin-7-one;
2-[4-(1H-Benzoimidazol-2-yl)-phenylamino]-8-ethyl-8H-pyrido[2,3-d]pyrimidin-7-one;
2-[4-(Benzyloxy-phenylamino]-8-ethyl-8H-pyrido[2,3-d]pyrimidin-7-one;
8-Ethyl-2-[4-(4-methyl-piperidine-1-carbonyl)-phenylamino]-8H-pyrido[2,3-d]pyrimidin-7-one;
2-(3,4-Dimethoxy-phenylamino]-8-ethyl-8H-pyrido[2,3-d]pyrimidin-7-one;
8-Ethyl-2-(4-hydroxy-3-methoxy-phenylamino]-8H-pyrido[2,3-d]pyrimidin-7-one;
2-[4-(2,3-Dihydroxy-propoxy)-phenylamino]-8-ethyl-8H-pyrido[2,3-d]pyrimidin-7-one;
2-[4-(2-Diethylamino-ethylamino)-phenylamino]-8-ethyl-8H-pyrido[2,3-d]pyrimidin-7-one;
2-[3-(1H-Benzoimidazol-2-yl)-phenylamino]-8-ethyl-8H-pyrido[2,3-d]pyrimidin-7-one; and
8-Ethyl-6-methyl-2-{4-[4-(3-morpholin-4-yl-propyl)-piperidin-1-yl]-phenylamino}-8H-pyrido[2,3-d]pyrimidin-7-one.

7. A compound of claim 3 wherein $R^1$ is a substituted or unsubstituted, alkyl or branched alkyl, or cycloalkyl.

8. A compound according to claim 7 selected from:
2-Benzylamino-8-ethyl-8H-pyrido[2,3-d]pyrimidin-7-one;
8-Ethyl-2-ethylamino-8H-pyrido[2,3-d]pyrimidin-7-one;
2-tert-Butylamino-8-ethyl-8H-pyrido[2,3-d]pyrimidin-7-one;
8-Ethyl-2-isopropylamino-8H-pyrido[2,3-d]pyrimidin-7-one;
2-Cyclohexylamino-8-ethyl-8H-pyrido[2,3-d]pyrimidin-7-one;
2-Ethylamino-8-phenyl-8H-pyrido[2,3-d]pyrimidin-7-one;
8-Ethyl-2-[3-(4-methyl-piperazin-1-yl)-propylamino-8H-pyrido[2,3-d]pyrimidin-7-one;
8-Cyclohexyl-2-cyclohexylamino-8H-pyrido[2,3-d]pyrimidin-7-one;
8-Cyclohexyl-2-(2-piperidin-1-yl-ethylamino)-8H-pyrido[2,3-d]pyrimidin-7-one;
8-Cyclohexyl-2-(3-piperidin-1-yl-propylamino)-8H-pyrido[2,3-d]pyrimidin-7-one;
8-(3-Hydroxy-propyl)-2-(4-piperidin-1-yl-phenylamino)-8H-pyrido[2,3-d]pyrimidin-7-one;
2-Benzylamino-8-cyclohexyl-8H-pyrido[2,3-d]pyrimidin-7-one; and
8-Cyclohexyl-2-(4-methoxy-benzylamino)-8H-pyrido[2,3-d]pyrimidin-7-one.

9. A compound of claim 3 wherein $R^1$ is $(CH_2)_n$heteroaryl or $(CH_2)_n$heterocyclyl.

10. A compound according to claim 9 selected from:
8-Ethyl-2-(pyridin-4-ylamino)-8H-pyrido[2,3-d]pyrimidin-7-one;
8-Ethyl-2-(1H-indazol-6-ylamino)-8H-pyrido[2,3-d]pyrimidin-7-one;
8-Ethyl-2-(9H-fluoren-3-ylamino)-8H-pyrido[2,3-d]pyrimidin-7-one;
8-Ethyl-2-(1H-indol-6-ylamino)-8H-pyrido[2,3-d]pyrimidin-7-one;
2-(2,3-Dihydro-1H-indol-6-ylamino)-8-ethyl-8H-pyrido[2,3-d]pyrimidin-7-one; and
2-(2,3-Diphenyl-quinoxalin-6-ylamino)-8-ethyl-8H-pyrido[2,3-d]pyrimidin-7-one.

11. A compound of claim 4 wherein $R^2$ is cycloalkyl or heterocyclyl.

12. A compound according to claim 11 selected from:
8-Cyclopentyl-2-phenylamino-8H-pyrido[2,3-d]pyrimidin-7-one;
8-Cyclopentyl-2-[4-(4-methyl-piperazin-1-yl)-phenylamino]-8H-pyrido[2,3-d]pyrimidin-7-one;
8-Cyclopentyl-2-[4-(2-diethylamino-ethoxy)-phenylamino]-8H-pyrido[2,3-d]pyrimidin-7-one;
8-Cyclohexyl-2-phenylamino-8H-pyrido[2,3-d]pyrimidin-7-one;
8-Cyclohexyl-2-[4-(2-diethylamino-ethoxy)-phenylamino]-8H-pyrido[2,3-d]pyrimidin-7-one;
8-Cyclohexyl-2-[4-(4-methyl-piperazin-1-yl)-phenylamino]-8H-pyrido[2,3-d]pyrimidin-7-one;
8-Cyclopropyl-2-phenylamino-8H-pyrido[2,3-d]pyrimidin-7-one;
8-Cyclopropyl-2-[4-(2-diethylamino-ethoxy)-phenylamino]-8H-pyrido[2,3-d]pyrimidin-7-one;
8-Cyclopropyl-2-[4-(4-methyl-piperazin-1-yl)-phenylamino]-8H-pyrido[2,3-d]pyrimidin-7-one;
8-Cyclohexyl-2-(4-piperidin-1-yl-phenylamino)-8H-pyrido[2,3-d]pyrimidin-7-one;
8-Cyclohexyl-2-{4-[4-(2-hydroxy-ethyl)-3,5-dimethyl-piperazin-1-yl]-phenylamino}-8H-pyrido[2,3-d]pyrimidin-7-one;
8-Cyclohexyl-2-{4-[4-(3-dimethylamino-propyl)-piperazin-1-yl]-phenylamino}-8H-pyrido[2,3-d]pyrimidin-7-one;

8-Cyclohexyl-2-[4-(3,5-dimethyl-piperazin-1-yl)-phenylamino]-8H-pyrido[2,3-d]pyrimidin-7-one;
8-Cyclohexyl-2-(4-dimethylamino-phenylamino)-8H-pyrido[2,3-d]pyrimidin-7-one,
8-Cyclohexyl-2-(4-fluoro-phenylamino)-8H-pyrido[2,3-d]pyrimidin-7-one;
8-Cyclohexyl-2-[4-(2-diethylamino-ethoxy)-3-methyl-phenylamino]-8H-pyrido[2,3-d]pyrimidin-7-one;
8-Cycloheptyl-2-phenylamino-8H-pyrido[2,3-d]pyrimidin-7-one;
8-Cycloheptyl-2-[4-(2-diethylamino-ethoxy)-phenylamino]-8H-pyrido[2,3-d]pyrimidin-7-one;
8-Cyclopentyl-2-(4-piperidin-1-yl-phenylamino)-8H-pyrido[2,3-d]pyrimidin-7-one;
8-Cyclohexyl-2-[4-(4-methyl-piperidin-1-yl)-phenylamino]-8H-pyrido[2,3-d]pyrimidin-7-one;
8-Cyclohexyl-2-(4-pyrrolidin-1-yl-phenylamino)-8H-pyrido[2,3-d]pyrimidin-7-one;
8-Cyclohexyl-2-(4-pyrrol-1-yl-phenylamino)-8H-pyrido[2,3-d]pyrimidin-7-one;
8-Cyclohexyl-2-(4-pyrazol-1-yl-phenylamino)-8H-pyrido[2,3-d]pyrimidin-7-one;
8-Cycloheptyl-2-(4-piperidin-1-yl-phenylamino)-8H-pyrido[2,3-d]pyrimidin-7-one;
8-Cyclohexyl-2-[4-(3,5-dimethyl-piperidin-1-yl)-phenylamino]-8H-pyrido[2,3-d]pyrimidin-7-one;
8-Cyclohexyl-2-[4-(3,4-dihydro-1H-isoquinolin-2-yl)-phenylamino]-8H-pyrido[2,3-d]pyrimidin-7-one;
8-Cyclohexyl-2-[4-(3-methyl-piperidin-1-yl)-phenylamino]-8H-pyrido[2,3-d]pyrimidin-7-one;
8-Cyclohexyl-2-(4-thiomorpholin-4-yl-phenylamino)-8H-pyrido[2,3-d]pyrimidin-7-one;
8-Bicyclo[2.2.1]hept-2-yl-2-phenylamino-8H-pyrido[2,3-d]pyrimidin-7-one;
8-Bicyclo[2.2.1]hept-2-yl-2-(4-piperidin-1-yl-phenylamino)-8H-pyrido[2,3-d]pyrimidin-7-one;
8-Cycloheptyl-2-(4-fluoro-phenylamino)-8H-pyrido[2,3-d]pyrimidin-7-one;
8-Cyclohexyl-2-[4-(3-hydroxymethyl-piperidin-1-yl)-phenylamino]-8H-pyrido[2,3-d]pyrimidin-7-one;
8-Cyclopentyl-2-(4-pyrrol-1-yl-phenylamino)-8H-pyrido[2,3-d]pyrimidin-7-one;
8-Cyclopentyl-2-(4-pyrazol-1-yl-phenylamino)-8H-pyrido[2,3-d]pyrimidin-7-one;
8-Cyclopentyl-2-[4-(3,5-dimethyl-pyrazol-1-yl)-phenylamino]-8H-pyrido[2,3-d]pyrimidin-7-one;
8-Cyclopentyl-2-{4-[4-(2-hydroxy-ethyl)-piperidin-1-yl]-phenylamino}-8H-pyrido[2,3-d]pyrimidin-7-one;
8-Cyclopentyl-2-{4-[4-(3-hydroxy-propyl)-piperidin-1-yl]-phenylamino}-8H-pyrido[2,3-d]pyrimidin-7-one;
8-Cyclopentyl-2-[4-(4-hydroxy-piperidin-1-yl)-phenylamino]-8H-pyrido[2,3-d]pyrimidin-7-one;
2-(4-Piperidin-1-yl-phenylamino)-8-(tetrahydro-furan-3-yl)-8H-pyrido[2,3-d]pyrimidin-7-one;
8-Cycloheptyl-2-(3-piperidin-1-yl-phenylamino)-8H-pyrido[2',3-d]pyrimidin-7-one;
8-Cyclopentyl-2-(3-piperidin-1-yl-phenylamino)-8H-pyrido[2,3-d]pyrimidin-7-one;
8-Cyclohexyl-2-(3-piperidin-1-yl-phenylamino)-8H-pyrido[2,3-d]pyrimidin-7-one;
8-Cyclopentyl-2-[4-(3-hydroxy-piperidin-1-yl)-phenylamino]-8H-pyrido[2,3-d]pyrimidin-7-one;
8-Cyclopentyl-2-[4-(2-hydroxymethyl-piperidin-1-yl)-phenylamino]-8H-pyrido[2,3-d]pyrimidin-7-one;
2-(4-Piperidin-1-yl-phenylamino)-8-(tetrahydro-pyran-4-yl)-8H-pyrido[2,3-d]pyrimidin-7-one;
8-Bicyclo[2.2.1]hept-2-yl-2-(4-fluoro-phenylamino)-8H-pyrido[2,3-d]pyrimidin-7-one;
8-Bicyclo[2.2.1]hept-2-yl-2-[3-(1,1,2,2-tetrafluoro-ethoxy)-phenylamino]-8H-pyrido[2,3-d]pyrimidin-7-one;
8-Bicyclo[2.2.1]hept-2-yl-2-{4-[4-(3-hydroxy-propyl)-piperidin-1-yl]-phenylamino}-8H-pyrido[2,3-d]pyrimidin-7-one;
8-Cyclohexyl-2-[4-(4-hydroxy-piperidin-1-yl)-phenylamino]-8H-pyrido[2,3-d]pyrimidin-7-one;
8-Cyclohexyl-2-{4-[4-(2-hydroxy-ethyl)-piperidin-1-yl]-phenylamino}-8H-pyrido[2,3-d]pyrimidin-7-one;
8-Bicyclo[2.2.1]hept-2-yl-2-(4-pyrazol-1-yl-phenylamino)-8H-pyrido[2,3-d]pyrimidin-7-one;
8-Bicyclo[2.2.1]hept-2-yl-2-[4-(1,1,2,2-tetrafluoro-ethoxy)-phenylamino]-8H-pyrido[2,3-d]pyrimidin-7-one;
8-Bicyclo[2.2.1]hept-2-yl-2-(3,4-difluoro-phenylamino)-8H-pyrido[2,3-d]pyrimidin-7-one;
8-Bicyclo[2.2.1]hept-2-yl-2-(4-trifluoromethylsulfanyl-phenylamino)-8H-pyrido[2,3-d]pyrimidin-7-one;
8-Bicyclo[2.2.1]hept-2-yl-2-(biphenyl-4-ylamino)-8H-pyrido[2,3-d]pyrimidin-7-one;
8-Bicyclo[2.2.1]hept-2-yl-2-[4-(2-diethylamino-ethoxy)-phenylamino]-8H-pyrido[2,3-d]pyrimidin-7-one;
8-Bicyclo[2.2.1]hept-2-yl-2-[4-(4-hydroxy-piperidin-1-yl)-phenylamino]-8H-pyrido[2,3-d]pyrimidin-7-one;
8-Bicyclo[2.2.1]hept-2-yl-2-{4-[4-(2-hydroxy-ethyl)-piperidin-1-yl]-phenylamino}-8H-pyrido[2,3-d]pyrimidin-7-one;
8-Bicyclo[2.2.1]hept-2-yl-2-(4-piperidin-1-yl-phenylamino)-8H-pyrido[2,3-d]pyrimidin-7-one;
8-Bicyclo[2.2.1]hept-2-yl-2-{4-[4-(3-dimethylamino-propyl)-piperazin-1-yl]-phenylamino}-8H-pyrido[2,3-d]pyrimidin-7-one;
8-Bicyclo[2.2.1]hept-2-yl-2-[4-(3-hydroxymethyl-piperidin-1-yl)-phenylamino]-8H-pyrido[2,3-d]pyrimidin-7-one;
8-(2-Hydroxy-cyclopentyl)-2-(4-piperidin-1-yl-phenylamino)-8H-pyrido[2,3-d]pyrimidin-7-one;
4-[7-Oxo-2-(4-piperidin-1-yl-phenylamino)-7H-pyrido[2,3-d]pyrimidin-8-yl]-piperidine-1-carboxylic acid ethyl ester;
8-Bicyclo[2.2.1]hept-2-yl-2-{4-[4-(3-morpholin-4-yl-propyl)-piperidin-1-yl]-phenylamino}-8H-pyrido[2,3-d]pyrimidin-7-one;
8-Bicyclo[2.2.1]hept-2-yl-2-{4-[3-(3-hydroxy-propyl)-piperidin-1-yl]-phenylamino}-8H-pyrido[2,3-d]pyrimidin-7-one;
8-Bicyclo[2.2.1]hept-2-yl-2-[4-(3-diethylamino-2-hydroxy-propoxy)-phenylamino]-8H-pyrido[2,3-d]pyrimidin-7-one;
8-Bicyclo[2.2.1]hept-2-yl-2-[4-(2-hydroxy-3-morpholin-4-yl-propoxy)-phenylamino]-8H-pyrido[2,3-d]pyrimidin-7-one;
8-Bicyclo[2.2.1]hept-2-yl-2-{4-[3-(3-morpholin-4-yl-propyl)-piperidin-1-yl]-phenylamino}-8H-pyrido[2,3-d]pyrimidin-7-one;
8-Bicyclo[2.2.1]hept-2-yl-2-[4-(3-morpholin-4-ylmethyl-piperidin-1-yl)-phenylamino]-8H-pyrido[2,3-d]pyrimidin-7-one;
8-Ethyl-6-methyl-2-{4-[4-(3-morpholin-4-yl-propyl)-piperidin-1-yl]-phenylamino}-8H-pyrido[2,3-d]pyrimidin-7-one; and
8-Bicyclo[2.2.1]hept-2-yl-2-(4-piperidin-1-yl-phenylamino)-8H-pyrido[2,3-d]pyrimidin-7-one.

13. A compound of claim 1 wherein $R^1$ is phenyl substituted with hydroxy, alkoxy, $NR^4R^5$, or $T(CH_2)_mQR^4$.

14. A compound of claim 1 wherein W is S, SO, or $SO_2$.

15. A compound of claim 14 wherein $R^1$ is a substituted or unsubstituted, straight or branched alkyl.

16. A compound according to claim 15 which is:
2-Methanesulfanyl-8H-pyrido[2,3-d]pyrimidin-7-one;
8-Ethyl-2-methanesulfanyl-8H-pyrido[2,3-d]pyrimidin-7-one;
8-Ethyl-2-methanesulfinyl-8H-pyrido[2,3-d]pyrimidin-7-one;
8-Ethyl-2-methanesulfonyl-8H-pyrido[2,3-d]pyrimidin-7-one;
8-Methyl-2-methanesulfanyl-8H-pyrido[2,3-d]pyrimidin-7-one;
8-Methyl-2-methanesulfonyl-8H-pyrido[2,3-d]pyrimidin-7-one;
8-(4-Methoxybenzylamino)-2-methanesulfanyl-8H-pyrido[2,3-d]pyrimidin-7-one;
2-Methanesulfinyl-8H-pyrido[2,3-d]pyrimidin-7-one;
8-Isopropyl-2-methanesulfanyl-8H-pyrido[2,3-d]pyrimidin-7-one;
8-Isopropyl-2-methanesulfinyl-8H-pyrido[2,3-d]pyrimidin-7-one;
8-Methyl-2-methanesulfanyl-8H-pyrido[2,3-d]pyrimidin-7-ylideneamine;
8-Isopentyl-2-methanesulfanyl-8H-pyrido[2,3-d]pyrimidin-7-one;
8-(1-Ethylpropyl)-2-methanesulfinyl-8H-pyrido[2,3-d]pyrimidin-7-one;
6-Methyl-2-methylsulfanyl-8H-pyrido [2,3-d]pyrimidin-7-one;
8-Ethyl-6-methyl-2-methylsulfanyl-8H-pyrido[2,3-d]pyrimidin-7-one;
8-Ethyl-2-methanesulfinyl-6-methyl-8H-pyrido[2,3-d]pyrimidin-7-one;
2-Methanesulfinyl-8-phenyl-8H-pyrido[2,3-d]pyrimidin-7-one;
8-Cyclopentyl-2-methanesulfanyl-8H-pyrido[2,3-d]pyrimidin-7-one;
8-Cyclopentyl-2-methanesulfinyl-8H-pyrido[2,3-d]pyrimidin-7-one;
8-Cyclohexyl-2-methylsulfanyl-8H-pyrido[2,3-d]pyrimidin-7-one;
8-Cyclohexyl-2-methanesulfinyl-8H-pyrido[2,3-d]pyrimidin-7-one,
8-Cyclopropyl-2-methylsulfanyl-8H-pyrido[2,3-d]pyrimidin-7-one;
8-Cyclopropyl-2-methanesulfinyl-8H-pyrido[2,3-d]pyrimidin-7-one;
8-(2-Benzyloxy-ethyl)-2-methanesulfinyl-8H-pyrido[2,3-d]pyrimidin-7-one;
8-Cycloheptyl-2-methylsulfanyl-8H-pyrido[2,3-d]pyrimidin-7-one;
8-Cycloheptyl-2-methanesulfinyl-8H-pyrido[2,3-d]pyrimidin-7-one;
8-Bicyclo[2.2.1]hept-2-yl-2-methylsulfanyl-8H-pyrido[2,3-d]pyrimidin-7-one (exo);
8-Bicyclo[2.2.1]hept-2-yl-2-methanesulfinyl-8H-pyrido[2,3-d]pyrimidin-7-one;
8-Cyclohexylmethyl-2-methanesulfinyl-8H-pyrido[2,3-d]pyrimidin-7-one;
2-Methylsulfonyl-8-[3-(tetrahydro-pyran-2-yloxy)propyl]-8H-pyrido[2,3-d]pyrimidin-7-one;
2-Methanesulfinyl-8-[3-(tetrahydro-pyran-2H-yloxy)-propyl]-8H-pyrido[2,3-d]pyrimidin-7-one;
4-(2-methanesulfanyl-7-oxo-7H-pyrido[2,3-d]pyrimidin-8-yl)-piperidine-1-carboxylic acid ethyl ester;
4-(2-methanesulfinyl-7-oxo-7H-pyrido[2,3-d]pyrimidin-8-yl)-piperidine-1-carboxylic acid ethyl ester;
2-methylsulfanyl-8-[2,2-dimethyl-3-(tetrahydro-pyran-2-yloxy)propyl]-8H-pyrido[2,3-d]pyrimidin-7-one;
2-Methylsulfinyl-8-[2,2-dimethyl-3-(tetrahydro-pyran-2-yloxy)propyl]-8H-pyrido[2,3-d]pyrimidin-7-one;
6-Methyl-2-methylsulfanyl-8H-pyrido[2,3-d]pyrimidin-7-one;
8-Ethyl-6-methyl-2-methylsulfanyl-8H-pyrido[2,3-d]pyrimidin-7-one; and
8-Ethyl-2-methanesulfinyl-6-methyl-8H-pyrido[2,3-d]pyrimidin-7-one.

17. A compound of claim 15 wherein $R^2$ is cycloalkyl.

18. A compound selected from:
8-Bicyclo[2.2.1]hept-2-yl-2-[4-[4-(3-morpholin-4-yl-propyl)-piperidin-1-yl]-phenylamino]-8H-pyrido[2,3-d]pyrimidin-7-one (exo); and
8-Bicyclo[2.2.1]hept-2-yl-2-[4-[4-(2-morpholin-4-yl-ethyl)-piperidin-1-yl]-phenylamino]-8H-pyrido[2,3-d]pyrimidin-7-one (exo).

19. A compound having the general Formula II:

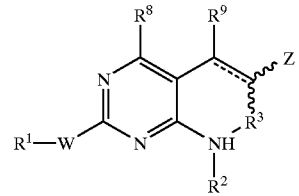

II wherein:
the dotted line represents an optional bond of either trans or cis-stereochemistry;
W is NH, S, SO, or $SO_2$;
Z is $COOR^7$, CN, CHO, $CH_2OR^7$, $CH_2NHR^7$, $CONHR^7$, or $COR^7$;
$R^1$ is selected from the group consisting of phenyl, $(CH_2)_n$phenyl, naphthyl, $(CH_2)_n$ $C_2$–$C_8$ heteroaryl, $(CH_2)_n$ $C_2$–$C_6$ heterocyclyl, $C_1$–$C_{10}$ alkyl, and $C_3$–$C_{10}$ cycloalkyl, wherein n is 0 or 1 and the phenyl, $(CH_2)_n$heteroaryl, alkyl, and cycloalkyl groups are optionally substituted by up to 5 groups selected from $NR^4R^5$, $N(O)R^4R^5$, phenyl, substituted phenyl, hydroxy, $C_1$–$C_6$ alkyl, $C_1$–$C_6$ alkoxy, phenoxy, thiol, $C_1$–$C_6$ thioalkyl, halo, $COR^4$, $CO_2R^4$, $CONR^4R^5$, $SO_2NR^4R^5$, $SO_3R^4$, aldehyde, nitrile, nitro, $C_2$–$C_6$ heteroaryloxy, $T(CH_2)_mQR^4$, $C(O)T(CH_2)_mQR^4$, $NHC(O)T(CH_2)_mQR^4$, or $T(CH_2)_mCO_2R^4$ wherein m is 1–6, T is O, S, $NR^4$, $N(O)R^4$ or $CR^4R^5$, and Q is O, S, $NR^5$, or $N(O)R^5$;
$R^2$ is selected from the group consisting of $C_1$–$C_{10}$ alkyl, $C_3$–$C_{10}$ cycloalkyl, $(CH_2)_n$phenyl, $(CH_2)_n$ $C_2$–$C_6$ heteroaryl, $(CH_2)_n$ $C_2$–$C_6$ heterocyclyl, wherein n is 0, 1, or 2 and the phenyl, $(CH_2)_n$heteroaryl, alkyl, and cycloalkyl groups are optionally substituted by up to 5 groups selected from $NR^4R^5$, $C_1$–$C_6$ alkyl, hydroxy, nitrile, $C_1$–$C_6$ alkoxy, halo, $CO_2R^4$, and $CONR^4R^5$;
$R^3$ is halo, nitro, cyano, $OR^4$, $CO_2R^4$, $CONR^4R^5$, or $NR^4R^5$;
$R^4$ and $R^5$ are independently selected from the group consisting of hydrogen, $C_1$–$C_6$ alkyl, substituted alkyl, $C_3$–$C_{10}$ cycloalkyl, $C_2$–$C_6$ heterocyclyl, and $C_2$–$C_6$ heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur; optionally substituted with alkyl, $T(CH_2)_mQR^{4'}$, $C(O)T(CH_2)_mQR^{4'}$, $T(CH_2)_mCO_2R^{4'}$, $(CH_2)_nQR^{4'}$, $T(CH_2)_mCON\ R^{4'}R^{5'}$ wherein m is 1–6, T is O, S, $NR^{4'}$, $N(O)R^{4'}$, or $CR^{4'}R^{5'}$, and Q is O, S, $NR^{5'}$, or $N(O)R^{5'}$;

$R^{4'}$ and $R^{5'}$ are independently selected from the group consisting of hydrogen, $C_1$–$C_6$ alkyl, substituted alkyl, $C_3$–$C_{10}$ cycloalkyl, $C_2$–$C_6$ heterocyclyl, and $C_2$–$C_6$ heteroaryl;

R7 is H, $C_1$–$C_6$ alkyl, or phenyl;

R8 is H, $C_1$–$C_3$ alkyl, and halo;

$R^9$ is H, $C_1$–$C_3$ alkyl, $NR^4R^5$, $N(O)R^4R^5$, hydroxy, $C_1$–$C_6$ alkoxy, thiol, $C_1$–$C_6$ thioalkyl, halo, $COR^4$, $CO_2R^4$, $CONR^4R^5$, $SO_2NR^4R^5$, $SO_3R^4$, CHO, CN, or $NO_2$;

and the pharmaceutically acceptable salts thereof.

20. A compound of claim 19 wherein W is NH, and $R^8$ and $R^9$ both are hydrogen.

21. A compound of claim 20 wherein $R^1$ is phenyl or substituted phenyl.

22. A compound according to claim 21 which is:

Ethyl 3-(4-Ethylamino-2-phenylamino-pyrimidin-5-yl)acrylate;

Ethyl 3-(4-Amino-2-phenylamino-pyrimidin-5-yl)acrylate;

3-(4-Ethylamino-2-phenylamino-pyrimidin-5-yl)propionic acid ethyl ester;

3-(4-Ethylamino-2-phenylamino-pyrimidin-5-yl) acrylonitrile; or 3-(4-Ethylamino-2-phenylamino-pyrimidin-5-yl)-but-2-enoic acid ethyl ester.

23. A compound of claim 19 wherein W is S, SO, or $SO_2$.

24. A compound according to claim 23 which is:

Ethyl 3-(4-Amino-2-methanesulfanyl-pyrimidin-5-yl)acrylate;

Ethyl 3-(4-Ethylamino-2-methanesulfanyl-pyrimidin-5-yl)acrylate;

Ethyl 3-(4-Methylamino-2-methanesulfanyl-pyrimidin-5-yl)acrylate;

3-(4-Methylamino-2-methanesulfanyl-pyrimidin-5-yl)-acrylonitrile;

Ethyl 3-(4-Cyclopentylamino-2-methanesulfanyl-pyrimidin-5-yl)acrylate;

3-(4-Cyclohexylamino-2-methysulfanyl-pyrimidin-5-yl)-acrylic acid ethyl ester;

3-(4-Cyclopropylamino-2-methylsulfanyl-pyrimidin-5-yl)-acrylic acid ethyl ester; and 4-[5-(2-Ethoxycarbonyl-vinyl)-2-methylsulfanyl-pyrimidin 4 yl amino]-piperidine-1-carboxylic acid ethyl ester.

25. A pharmaceutical formulation comprising a compound selected from claims 1–22 in combination with a pharmaceutically acceptable carrier, diluent, or excipient.

26. A method for controlling proliferative disorders selected from the group consisting of cancer, psoriasis, vascular smooth muscle proliferation associated with a disorder selected from the group consisting of atherosclerosis, postsurgical vascular stenosis, and restenosis in mammals comprising administration to said mammal a therapeutically effective pharmaceutical formulation according to any one of claims 1–24.

27. A method of inhibiting a cyclin-dependent kinase comprising contacting the cyclin-dependent kinase with a compound selected from any one of claims 1–24.

28. A method of claim 27 wherein said cyclin-dependent kinase is cdc2.

29. A method of claim 27 wherein said cyclin-dependent kinase is cdk2.

30. A method of claim 27 wherein said cyclin-dependent kinase is cdk4 or cdk6.

31. A method of inhibiting a growth factor-mediated receptor tyrosine kinase comprising contacting said growth factor-mediated kinase with a compound selected from one of claims 1–24.

32. A method of claim 31 wherein said growth factor-mediated receptor tyrosine kinase is platelet derived growth factor (PDGF).

33. A method of claim 31 wherein said growth factor-mediated receptor tyrosine kinase is fibroblast growth factor (FGF).

34. A method of treating a subject suffering from diseases caused by vascular smooth muscle cell proliferation comprising administration of a therapeutically effective amount of a compound selected from claims 1–24 to said subject.

35. A method of treating a subject suffering from cancer comprising administration to said subject of a therapeutically effective amount of a compound selected from claims 1–24.

36. A compound of claim 1, wherein $R^1$ is substituted by up to 5 groups selected from $NR^4R^5$, $C_1$–$C_6$ alkoxy, halo, $COOR^4$, $CONR^{45}$, $SO_2NR^{45}$, $SO_3R^4$, $C(O)T(CH_2)_mQR^4$, or $NHC(O)T(CH_2)_mQR^4$.

37. A compound of claim 1, wherein $R^1$ is $(CH_2)_n$phenyl, phenyl, $(CH_2)_n$ $C_2$–$C_6$ heteroaryl, $(CH_2)_n$ $C_2$–$C_6$ heterocyclyl, $C_1$–$C_{10}$ alkyl, or $C_3$–$C_{10}$ cycloalkyl.

38. A compound of claim 37, wherein $R^1$ is indolyl, pyridyl, piperazinyl, dimethylpiperazinyl, piperidinyl, substituted piperazinyl, pyrrolidyl, phenyl, benzyl or phenylethyl.

39. A compound of claim 1, wherein $R^2$ is $C_1$–$C_{10}$ alkyl, $C_3$–$C_{10}$ cycloalkyl, $(CH_2)_n$phenyl, $(CH_2)_n$ $C_2$–$C_6$ heteroaryl, or $(CH_2)_n$ $C_2$–$C_6$ heterocyclyl.

40. A compound of claim 39, wherein $R^2$ is cyclopentyl, cyclohexyl, cycloheptyl, ethyl, propyl, butyl, isopropyl, isobutyl, t-butyl, isopentyl, ethylpropyl, or ethylbutyl.

41. A compound according to claim 6 selected from:

2-[4-(2-Diethylaminoethoxy)-phenylamino]-8-ethyl-8H-pyrido[2,3-d]pyrimidin-7-one;

8-Ethyl-2-[4-(4-methylpiperazin-1-yl)-phenylamino]-8H-pyrido[2,3-d]pyrimidin-7-one;

2-[4-(2-Diethylaminoethoxy)-phenylamino]-8-isopropyl-8H-pyrido[2,3-d]pyrimidin-7-one;

8-Isopropyl-2-[4-(4-methylpiperazin-1-yl)-phenylamino]-8H-pyrido[2,3-d]pyrimidin-7-one;

8-(1-Ethylpropyl)-2-[4-(4-methylpiperazin-1-yl)-phenylamino]-8H-pyrido[2,3-d]pyrimidin-7-one; and 8-Ethyl-6-methyl-2-[4-(4-methyl-piperazin-1-yl)-phenylamino-8H-pyrido[2,3-d]pyrimidin-7-one.

42. A compound according to claim 8, having the formula:

8-Ethyl-2-[3-(4-methyl-piperazin-1-yl)-propylamino-8H-pyrido[2,3-d]pyrimidin-7-one.

43. A compound according to claim 12 selected from:

8-Cyclopentyl-2-[4-(4-methyl-piperazin-1-yl)-phenylamino]-8H-pyrido[2,3-d]pyrimidin-7-one;

8-Cyclopentyl-2[4-(2-diethylamino-ethoxy)-phenylamino]-8H-pyrido[2,3-d]pyrimidin-7-one;

8-Cyclohexyl-2-[4-(2-diethylamino-ethoxy)-phenylamino]-8H-pyrido[2,3-d]pyrimidin-7-one;

8-Cyclohexyl-2-[4-(4-methyl-piperazin-1-yl)-phenylamino]-8H-pyrido[2,3-d]pyrimidin-7-one;

8-Cyclohexyl-2-[4-(3,5-dimethyl-piperazin-1-yl)-phenylamino]-8H-pyrido[2,3-d]pyrimidin-7-one; and 8-Cycloheptyl-2-[4-(2-diethylamino-ethoxy)-phenylamino]-8H-pyrido[2,3-d]pyrimidin-7-one.

44. A compound according to claim 1 selected from:

8-Ethyl-2-(pyridin-4-ylamino)-8H-pyrido[2,3-d]pyrimidin-7-one;

2-Amino-8-methyl-8H-pyrido[2,3-d]pyrimidin-7-one;

2-Benzylamino-8-methyl-8H-pyrido[2,3-d]pyrimidin-7-one;

2-Butylamino-8-methyl-8H-pyrido[2,3-d]pyrimidin-7-one;

2-Ethylamino-8-methyl-8H-pyrido[2,3-d]pyrimidin-7-one;

8-Methyl-2-(2-pyridin-2-yl-ethylamino)-8H-pyrido[2,3-d]pyrimidin-7-one;

2-Isopropylamino-8-methyl-8H-pyrido[2,3-d]pyrimidin-7-one;

8-Isopentyl-2-methanesulfanyl-8H-pyrido[2,3-d]pyrimidin-7-one;

8-(1-Ethylpropyl)-2-methanesulfinyl-8H-pyrido[2,3-d]pyrimidin-7-one;

2-Phenylamino-8-phenyl-8H-pyrido[2,3-d]pyrimidin-7-one;

2-[4-(4-Methyl-piperazin-1-yl)-phenylamino]-8-phenyl-8H-pyrido[2,3-d]pyrimidin-7-one;

N-{2-[4-(8-Ethyl-7-oxo-7,8-dihydro-pyrido[2,3-d]pyrimidin-2-ylamino)-phenyl]-2-hydroxy-1-hydroxymethyl-ethyl}-acetamide;

3-(8-Ethyl-7-oxo-7,8-dihydro-pyrido[2,3-d]pyrimidin-2-ylamino)-benzamide;

N-[4-[2-[4-[(8-Ethyl-7,8-dihydro-7-oxopyrido[2,3-d]pyrimidin-2-yl)amino]phenoxy]ethoxy]phenyl]propanediimidamide; and 3-(8-Ethyl-7-oxo-7,8-dihydro-pyrido[2,3-d]pyrimidin-2-ylamino)-N,N-dimethyl-benzamide;

1-[4-(8-Cyclohexyl-7-oxo-7,8-dihydro-pyrido[2,3-d]pyrimidin-2-ylamino)-phenyl]-piperidine-4-carboxylic acid ethyl ester;

1-[4-(8-Cyclohexyl-7-oxo-7,8-dihydro-pyrido[2,3-d]pyrimidin-2-ylamino)-phenyl]-pyrrolidine-2-carboxylic acid tert-butyl ester;

2-Benzylamino-8-cyclohexyl-8H-pyrido[2,3-d]pyrimidin-7-one;

1-[4-(8-Cyclohexyl-7-oxo-7,8-dihydro-pyrido[2,3-d]pyrimidin-2-ylamino)-phenyl]-piperidine-4-carboxylic acid ethyl ester;

1-[4-(8-Cyclohexyl-7-oxo-7,8-dihydro-pyrido[2,3-d]pyrimidin-2-ylamino)-phenyl]-pyrrolidine-2-carboxylic acid tert-butyl ester; and 2-Benzylamino-8-cyclohexyl-8H-pyrido[2,3-d]pyrimidin-7-one.

* * * * *